(12) United States Patent
Wiles et al.

(10) Patent No.: US 9,708,629 B2
(45) Date of Patent: Jul. 18, 2017

(54) CORRECTION OF CRB1 MUTATIONS

(71) Applicant: The Jackson Laboratory, Bar Harbor, ME (US)

(72) Inventors: Michael V. Wiles, Mount Desert, ME (US); Benjamin E. Low, Brewer, ME (US)

(73) Assignee: The Jackson Laboratory, Bar Harbor, ME (US)

( * ) Notice: Subject to any disclaimer, the term of this patent is extended or adjusted under 35 U.S.C. 154(b) by 45 days.

(21) Appl. No.: 14/294,779

(22) Filed: Jun. 3, 2014

(65) Prior Publication Data

US 2014/0359798 A1   Dec. 4, 2014

Related U.S. Application Data

(60) Provisional application No. 61/875,230, filed on Sep. 9, 2013, provisional application No. 61/830,412, filed on Jun. 3, 2013.

(51) Int. Cl.
| | | |
|---|---|---|
| *C12N 15/90* | (2006.01) | |
| *C07K 14/705* | (2006.01) | |
| *C12N 9/22* | (2006.01) | |
| *A01K 67/027* | (2006.01) | |
| *C07K 14/47* | (2006.01) | |

(52) U.S. Cl.
CPC ........ *C12N 15/907* (2013.01); *A01K 67/0275* (2013.01); *C07K 14/47* (2013.01); *A01K 2217/072* (2013.01); *A01K 2227/105* (2013.01); *A01K 2267/02* (2013.01); *A01K 2267/0306* (2013.01)

(58) Field of Classification Search
CPC .......................... C12N 15/907; A01K 67/0275
See application file for complete search history.

(56) References Cited

U.S. PATENT DOCUMENTS

2012/0192298 A1*  7/2012  Weinstein .......... A01K 67/0276
                                                          800/14

OTHER PUBLICATIONS

Kazuki et al. (J Hum Genet. 2001; 46: 600-603).*
O'Doherty et al. (Science. Sep. 23, 2005; 309: 2033-2-37).*
Kim et al. (J Craniofac Surg. 2009; 20: 1316-1326).*
Anthony et al. (Alcohol. 2010; 44: 659-671).*
Wefers, B. et al., Direct production of mouse disease models by embryo microinjection of TALENs and oligodeoxynucleotides, *PNAS* 110: 3782-3787, 2013.
Wefers, B. et al., Generation of targeted mouse mutants by embryo microinjection of TALEN mRNA, *Nature Protocols*, 8: 2355-2379, 2013.

* cited by examiner

*Primary Examiner* — Scott Long
(74) *Attorney, Agent, or Firm* — Dinsmore & Shohl LLP

(57) ABSTRACT

Genetically engineered mice having a corrected $Crb1^{rd8}$ mutation and methods for correcting the $Crb1^{rd8}$ mutation to produce the genetically engineered mice are provided according to aspects of the present invention. Kits, expression vectors and fusion proteins according to aspects of the invention are provided for use to produce the genetically engineered mice characterized by a corrected $Crb1^{rd8}$ mutation.

8 Claims, 11 Drawing Sheets

*Crb1*$^{rd8}$ mutant sequence
SEQ ID NO: 42      SEQ ID NO: 43

```
MUT  N    C    E    D    S    Y    S    S    Y    G    V    P    V    C    R    D    G    Q    G    H    T
Rd8  AAC  TGT  GAA  GAC  AGC  TAC  AGT  TCT  TAT  -GGT GTG  CCT  GTC  TGT  CGG  GAT  GGT  CAC  GGA  CAC  ACT
                                                      rd8 deletion
OLIGO            .........T......     ..C AG.     ...C         .........G......
```

SEQ ID NO: 44

B

Corrected sequence including synonymous substitutions reconstituting WT condition

SEQ ID NO: 46     SEQ ID NO: 45

```
CRB1  N    C    E    D    S    Y    S    S    Y    R    C    A    C    L    S    G    W    S    G    T    H
WT    AAC  TGT  GAA  GAC  AGC  TAC  AGT  TCT  TAT  CGG  TGT  GCC  TGT  CTC  TCG  GGA  TGG  TCA  GGG  ACA  CAC  T

CRB1  N    C    E    D    S    Y    S    S    Y    R    C    A    C    L    S    G    W    S    G    T    H
COR   AAC  TGT  GAA  GAC  AGT  TAC  AGC  AGT  TAT  CGG  TGT  GCC  TGT  CTG  TCG  GGA  TGG  TCA  GGG  ACA  CAC  T
```

SEQ ID NO: 44

Figure 2
SEQ ID NO: 52 ...GAGAGACAGGCACACC-ATAAGAACTGTAGCTGTC...
changed to
SEQ ID NO: 53 ...GACAGACAGGCACACCGATAACTGCTGTAACTGTC...
SEQ ID NO: 52 GAGAGACAGGCACACC-ATAAGAACTGTAGCTGTC
Wild Type
C57BL/6N
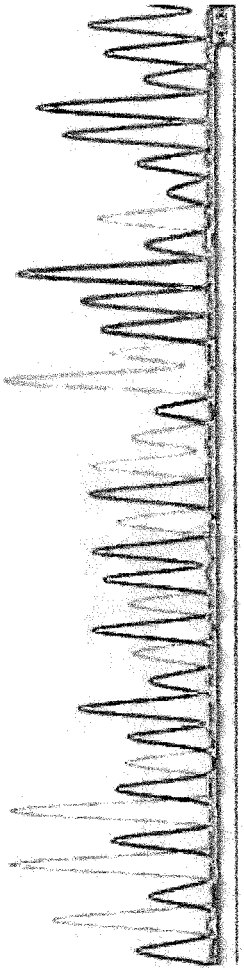
SEQ ID NO: 52 GAGAGACAGCCACACCC-ATAAGAACTGTAGCTGTC
SEQ ID NO: 53 GACAGACAGGCACACCGATAACTGCTGTAACTGTC
C57BL/6N "
rd8 repair"
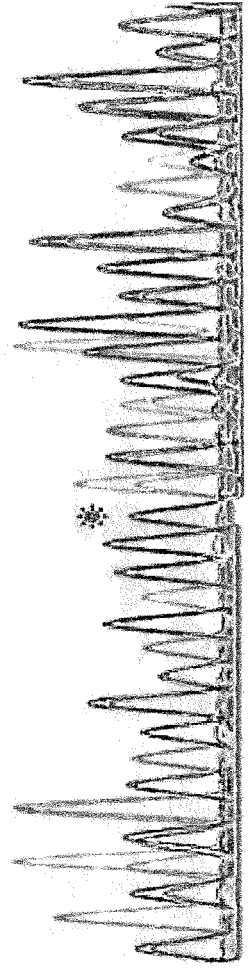
Sequence from founder #1508, a "perfect" homozygous rd8 repaired mouse REFERENCE: *This is a 1353/1368 PCR*

Figure 5

| Experiment | Live Born/Zygotes Injected ng/μl TALEN mRNA microinjected | | | | TALEN Induced Events/Live Born ng/μl TALEN mRNA microinjected | | | |
|---|---|---|---|---|---|---|---|---|
| | 10 | 25 | 50 | Total | 10 | 25 | 50 | Total |
| 200mer Sense | 14/84 17% | 30/116 26% | 32/99 32% | 76/299 25% | 6/14 43% | 24/30 80% | 30/32 94% | 60/76 79% |
| 200mer Anti-Sense | 22/95 23% | 36/112 32% | 28/90 31% | 86/297 29% | 12/22 55% | 24/36 67% | 20/28 71% | 56/86 65% |
| Combined: | 36/179 20% | 66/228 29% | 60/189 32% | 162/596 27% | 18/36 50% | 48/66 73% | 50/60 83% | 116/162 72% |

Figure 5 (Continued)

| Experiment | HDR/Live-Born ng/μl TALEN mRNA microinjected | | | | Illegitimate Recombination/Detectable ng/μl TALEN mRNA microinjected | | | |
|---|---|---|---|---|---|---|---|---|
| | 10 | 25 | 50 | Total | 10 | 25 | 50 | Total |
| 200mer Sense | 0/14 0% | 8/30 27% | 6/32 19% | 14/76 18% | 1/14 7% | 1/22 5% | 1/26 4% | 3/62 5% |
| 200mer Anti-Sense | 1/22 5% | 6/36 17% | 0/28 0% | 7/86 8% | 0/21 0% | 3/30 10% | 0/28 0% | 3/79 4% |
| Combined: | 1/36 3% | 14/66 21% | 6/60 10% | 21/162 13% | 1/35 3% | 4/52 8% | 1/54 2% | 6/141 4% |

Figure 6

| Experiment | Live Born/Zygotes Injected ng/μl ssODN DNA microinjected | | | | TALEN Induced Events/Live Born ng/μl ssODN DNA microinjected | | | |
|---|---|---|---|---|---|---|---|---|
| | 0.3 | 2 | 6 | Total | 0.3 | 2 | 6 | Total |
| 52mer Sense | 14/94 *15%* | 16/93 *17%* | 14/85 *16%* | 44/272 *16%* | 11/14 *79%* | 13/16 *81%* | 12/14 *86%* | 36/44 *82%* |
| 52mer Anti-Sense | 13/55 *24%* | 13/80 *16%* | 33/93 *35%* | 59/228 *26%* | 10/13 *77%* | 8/13 *62%* | 26/33 *79%* | 44/59 *75%* |
| Combined: | 27/149 *18%* | 29/173 *17%* | 47/178 *26%* | 103/500 *21%* | 21/27 *78%* | 21/29 *72%* | 38/47 *81%* | 80/103 *78%* |

Figure 6 (Continued)

| Experiment | HDR/Live Born ng/μl ssODN DNA microinjected | | | | Illegitimate Recombination/Detectable ng/μl ssODN DNA microinjected | | | |
|---|---|---|---|---|---|---|---|---|
| | 0.3 | 2 | 6 | Total | 0.3 | 2 | 6 | Total |
| 52mer Sense | 1/14 *7%* | 1/16 *6%* | 3/14 *21%* | 5/44 *11%* | *ND* | *ND* | *ND* | *ND* |
| 52mer Anti-Sense | 0/13 *0%* | 0/13 *0%* | 0/33 *0%* | 0/59 *0%* | *ND* | *ND* | *ND* | *ND* |
| Combined: | 1/27 *4%* | 1/29 *5%* | 3/47 *6%* | 5/103 *5%* | *ND* | *ND* | *ND* | *ND* |

US 9,708,629 B2

SEQUENCE LISTING

<160> NUMBER OF SEQ ID NOS: 62

<210> SEQ ID NO 1
<211> LENGTH: 200
<212> TYPE: DNA
<213> ORGANISM: Artificial Sequence
<220> FEATURE:
<223> OTHER INFORMATION: Single stranded 200mer sense strand donor
      oligonucleotide sequence for Crb1rd8 repair

<400> SEQUENCE: 1
ttctacaaat atggtactta ctggctgttt gccatcaaat gcctgccact ccagccctg      60 tttgcatgga ggaaactgtg aagacagtta cagcagttat cggtgtgcct gtctgtcggg    120
atggtcaggg acacactgtg aaatcaacat tgatgagtgc ttttctagcc cctgtatcca   180
tggcaactgc tctgatggag                                                200

<210> SEQ ID NO 2
<211> LENGTH: 200
<212> TYPE: DNA
<213> ORGANISM: Artificial Sequence
<220> FEATURE:
<223> OTHER INFORMATION: Single stranded 200mer antisense strand donor
      oligonucleotide sequence for Crb1rd8 repair

<400> SEQUENCE: 2
ctccatcaga gcagttgcca tggatacagg ggctagaaaa gcactcatca atgttgattt     60
cacagtgtgt ccctgaccat cccgacagac aggcacaccg ataactgctg taactgtctt    120
cacagtttcc tccatgcaaa caggggctgg agtggcaggc atttgatggc aaacagccag    180
taagtaccat atttgtagaa                                                200

<210> SEQ ID NO 3
<211> LENGTH: 52
<212> TYPE: DNA
<213> ORGANISM: Artificial Sequence
<220> FEATURE:
<223> OTHER INFORMATION: Single stranded 52mer sense strand donor
      oligonucleotide sequence for Crb1rd8 repair

<400> SEQUENCE: 3
tgaagacagt tacagcagtt atcggtgtgc ctgtctgtcg ggatggtcag gg             52

<210> SEQ ID NO 4
<211> LENGTH: 52
<212> TYPE: DNA
<213> ORGANISM: Artificial Sequence
<220> FEATURE:
<223> OTHER INFORMATION: Single stranded 52mer antisense strand donor
      oligonucleotide sequence for Crb1rd8 repair

<400> SEQUENCE: 4
ccctgaccat cccgacagac aggcacaccg ataactgctg taactgtctt ca             52

<210> SEQ ID NO 5
<211> LENGTH: 51
<212> TYPE: DNA
<213> ORGANISM: Artificial Sequence
<220> FEATURE:
<223> OTHER INFORMATION: SNP rs219888696 including rd8 mutation in Crb1
      which distinguishes C57BL/6N from C57BL/6J

<400> SEQUENCE: 5
tgaccatccc gagagacagg cacaccataa gaactgtagc tgtcttcaca g              51

-continued

<210> SEQ ID NO 6
<211> LENGTH: 52
<212> TYPE: DNA
<213> ORGANISM: Artificial Sequence
<220> FEATURE:
<223> OTHER INFORMATION: SNP rs219888696 in C57BL/6J, not mutated in
      Crb1 which distinguishes C57BL/6N from C57BL/6J

<400> SEQUENCE: 6
tgaccatccc gagagacagg cacaccgata agaactgtag ctgtcttcac ag         52

<210> SEQ ID NO 7
<211> LENGTH: 21
<212> TYPE: DNA
<213> ORGANISM: Artificial Sequence
<220> FEATURE:
<223> OTHER INFORMATION: SNP rs3709624 in C57BL/6NJ, which distinguishes
      C57BL/6NJ from C57BL/6J

<400> SEQUENCE: 7
aacgagaagc ccagagtcac c                                           21

<210> SEQ ID NO 8
<211> LENGTH: 21
<212> TYPE: DNA
<213> ORGANISM: Artificial Sequence
<220> FEATURE:
<223> OTHER INFORMATION: SNP rs3659787 in C57BL/6NJ, which distinguishes
      C57BL/6NJ from C57BL/6J

<400> SEQUENCE: 8
aacttactaa acaaacccac t                                           21

<210> SEQ ID NO 9
<211> LENGTH: 21
<212> TYPE: DNA
<213> ORGANISM: Artificial Sequence
<220> FEATURE:
<223> OTHER INFORMATION: SNP rs3722313 in C57BL/6NJ, which distinguishes
      C57BL/6NJ from C57BL/6J

<400> SEQUENCE: 9
agctccttcc cagcctgatc t                                           21

<210> SEQ ID NO 10
<211> LENGTH: 21
<212> TYPE: DNA
<213> ORGANISM: Artificial Sequence
<220> FEATURE:
<223> OTHER INFORMATION: SNP rs3702158 in C57BL/6NJ, which distinguishes
      C57BL/6NJ from C57BL/6J

<400> SEQUENCE: 10
ggcccagtgt gaacaaagga a                                           21

<210> SEQ ID NO 11
<211> LENGTH: 21
<212> TYPE: DNA
<213> ORGANISM: Artificial Sequence
<220> FEATURE:
<223> OTHER INFORMATION: SNP rs3724876 in C57BL/6NJ, which distinguishes
      C57BL/6NJ from C57BL/6J

<400> SEQUENCE: 11
tcaccagagc tgccctgagg c                                           21

-continued

```
<210> SEQ ID NO 12
<211> LENGTH: 51
<212> TYPE: DNA
<213> ORGANISM: Artificial Sequence
<220> FEATURE:
<223> OTHER INFORMATION: rs219888696 in C57BL/6NJ, including rd8
      mutation in Crb1 which distinguishes C57BL/6NJ from C57BL/6J

<400> SEQUENCE: 12
tgaccatccc gagagacagg cacaccataa gaactgtagc tgtcttcaca g          51

<210> SEQ ID NO 13
<211> LENGTH: 21
<212> TYPE: DNA
<213> ORGANISM: Artificial Sequence
<220> FEATURE:
<223> OTHER INFORMATION: SNP rs3709624 in C57BL/6J, which distinguishes
      C57BL/6NJ from C57BL/6J

<400> SEQUENCE: 13
aacgagaagc tcagagtcac c                                           21

<210> SEQ ID NO 14
<211> LENGTH: 21
<212> TYPE: DNA
<213> ORGANISM: Artificial Sequence
<220> FEATURE:
<223> OTHER INFORMATION: SNP rs3659787 in C57BL/6J, which distinguishes
      C57BL/6NJ from C57BL/6J

<400> SEQUENCE: 14
aacttactaa gcaaacccac t                                           21

<210> SEQ ID NO 15
<211> LENGTH: 21
<212> TYPE: DNA
<213> ORGANISM: Artificial Sequence
<220> FEATURE:
<223> OTHER INFORMATION: SNP rs3722313 in C57BL/6J, which distinguishes
      C57BL/6NJ from C57BL/6J

<400> SEQUENCE: 15
agctccttcc tagcctgatc t                                           21

<210> SEQ ID NO 16
<211> LENGTH: 21
<212> TYPE: DNA
<213> ORGANISM: Artificial Sequence
<220> FEATURE:
<223> OTHER INFORMATION: SNP rs3702158 in C57BL/6J, which distinguishes
      C57BL/6NJ from C57BL/6J

<400> SEQUENCE: 16
ggcccagtgt aaacaaagga a                                           21

<210> SEQ ID NO 17
<211> LENGTH: 21
<212> TYPE: DNA
<213> ORGANISM: Artificial Sequence
<220> FEATURE:
<223> OTHER INFORMATION: SNP rs3724876 in C57BL/6J, which distinguishes
      C57BL/6NJ from C57BL/6J

<400> SEQUENCE: 17
tcaccagagc ggccctgagg c                                           21

<210> SEQ ID NO 18
```

```
<211> LENGTH: 7
<212> TYPE: PRT
<213> ORGANISM: Artificial Sequence
<220> FEATURE:
<223> OTHER INFORMATION: Nuclear localization signal from SV40 Large
      T-antigen

<400> SEQUENCE: 18

Pro Lys Lys Lys Arg Lys Val
1               5

<210> SEQ ID NO 19
<211> LENGTH: 14
<212> TYPE: PRT
<213> ORGANISM: Artificial Sequence
<220> FEATURE:
<223> OTHER INFORMATION: Nuclear localization signal from nucleoplasmin

<400> SEQUENCE: 19

Arg Pro Ala Ala Thr Lys Lys Ala Gly Gln Ala Lys Lys Lys
1               5                   10

<210> SEQ ID NO 20
<211> LENGTH: 35
<212> TYPE: DNA
<213> ORGANISM: Artificial Sequence
<220> FEATURE:
<223> OTHER INFORMATION: Sequence present in genetically engineered
      mouse with corrected Crb1rd8

<400> SEQUENCE: 20
gacagttaca gcagttatcg gtgtgcctgt ctgtc                              35

<210> SEQ ID NO 21
<211> LENGTH: 35
<212> TYPE: DNA
<213> ORGANISM: Artificial Sequence
<220> FEATURE:
<223> OTHER INFORMATION: Sequence present in genetically engineered
      mouse with corrected Crb1rd8

<400> SEQUENCE: 21
gacagttaca gcagttatag gtgtgcctgt ctgtc                              35

<210> SEQ ID NO 22
<211> LENGTH: 35
<212> TYPE: DNA
<213> ORGANISM: Artificial Sequence
<220> FEATURE:
<223> OTHER INFORMATION: Sequence present in genetically engineered
      mouse with corrected Crb1rd8

<400> SEQUENCE: 22
gacagctaca gttcttatcg gtgtgcctgt ctgtc                              35

<210> SEQ ID NO 23
<211> LENGTH: 35
<212> TYPE: DNA
<213> ORGANISM: Artificial Sequence
<220> FEATURE:
<223> OTHER INFORMATION: Sequence present in genetically engineered
      mouse with corrected Crb1rd8

<400> SEQUENCE: 23
gacagttaca gcagttatcg gtgtgcctgt ctctc                              35

<210> SEQ ID NO 24
```

```
<211> LENGTH: 35
<212> TYPE: DNA
<213> ORGANISM: Artificial Sequence
<220> FEATURE:
<223> OTHER INFORMATION: Sequence present in genetically engineered
      mouse with corrected Crb1rd8

<400> SEQUENCE: 24
gacagttaca gcagttatcg gtgtgcctgt ctctc                              35

<210> SEQ ID NO 25
<211> LENGTH: 35
<212> TYPE: DNA
<213> ORGANISM: Artificial Sequence
<220> FEATURE:
<223> OTHER INFORMATION: Sequence present in genetically engineered
      mouse with corrected Crb1rd8

<400> SEQUENCE: 25
gacagctaca gcagttatcg gtgtgcctgt ctctc                              35

<210> SEQ ID NO 26
<211> LENGTH: 35
<212> TYPE: DNA
<213> ORGANISM: Artificial Sequence
<220> FEATURE:
<223> OTHER INFORMATION: Sequence present in genetically engineered
      mouse with corrected Crb1rd8

<400> SEQUENCE: 26
gacagctaca gttcttatag gtgtgcctgt ctgtc                              35

<210> SEQ ID NO 27
<211> LENGTH: 35
<212> TYPE: DNA
<213> ORGANISM: Artificial Sequence
<220> FEATURE:
<223> OTHER INFORMATION: Sequence present in genetically engineered
      mouse with corrected Crb1rd8

<400> SEQUENCE: 27
gacagctaca gttcttatcg gtgtgcctgt ctctc                              35

<210> SEQ ID NO 28
<211> LENGTH: 35
<212> TYPE: DNA
<213> ORGANISM: Artificial Sequence
<220> FEATURE:
<223> OTHER INFORMATION: Sequence present in genetically engineered
      mouse with corrected Crb1rd8

<400> SEQUENCE: 28
gacagttaca gttcttatcg gtgtgcctgt ctgtc                              35

<210> SEQ ID NO 29
<211> LENGTH: 35
<212> TYPE: DNA
<213> ORGANISM: Artificial Sequence
<220> FEATURE:
<223> OTHER INFORMATION: Sequence present in genetically engineered
      mouse with corrected Crb1rd8

<400> SEQUENCE: 29
gacagttaca gtagttatcg gtgtgcctgt ctgtc                              35

<210> SEQ ID NO 30
<211> LENGTH: 1693
```

<212> TYPE: DNA
<213> ORGANISM: Artificial Sequence
<220> FEATURE:
<223> OTHER INFORMATION: TAL left arm sequence, T7 RNA binding site, start codon and nuclear localization signal

<400> SEQUENCE: 30

```
atgcatctag agaagacaag aacctgaccc cagaccaggt agtcgcaatc gcgaacaata      60
atgggggaaa gcaagccctg gaaaccgtgc aaaggttgtt gccggtcctt tgtcaagacc     120
acggccttac accggagcaa gtcgtggcca ttgcaagcaa catcggtggc aaacaggctc     180
ttgagacggt tcagagactt ctcccagttc tctgtcaagc ccacgggctg actcccgatc     240
aagttgtagc gattgcgtcg aacattggag ggaaacaagc attggagact gtccaacggc     300
tccttcccgt gttgtgtcaa gcccacggtt tgacgcctgc acaagtggtc gccatcgcca     360
acaacaacgg cggtaagcag gcgctggaaa cagtacagcg cctgctgcct gtactgtgcc     420
aggatcatgg actgaccccca gaccaggtag tcgcaatcgc gtcgaacatt ggggaaagc     480
aagccctgga aaccgtgcaa aggttgttgc cggtcctttg tcaagaccac ggccttacac     540
cggagcaagt cgtggccatt gcatcccacg acggtggcaa acaggctctt gagacggttc     600
agagacttct cccagttctc tgtcaagccc acgggctgac tcccgatcaa gttgtagcga     660
ttgcgtcgaa cattggaggg aaacaagcat ggagactgt ccaacggctc cttcccgtgt     720
tgtgtcaagc ccacggtttg acgcctgcac aagtggtcgc catcgccaac aacaacggcg     780
gtaagcaggc gctggaaaca gtacagcgcc tgctgcctgt actgtgccag gatcatggac     840
tgaccccaga ccaggtagtc gcaatcgcgt cacatgacgg gggaaagcaa gccctggaaa     900
ccgtgcaaag gttgttgccg gtcctttgtc aagaccacgg ccttacaccg gagcaagtcg     960
tggccattgc aagcaatggg ggtggcaaac aggctcttga cggttcag agacttctcc    1020
cagttctctg tcaagcccac gggctgactc ccgatcaagt tgtagcgatt gcgtcgaaca    1080
ttggagggaa acaagcattg gagactgtcc aacggctcct tcccgtgttg tgtcaagccc    1140
acggtttgac gcctgcacaa gtggtcgcca tcgccagcca tgatggcggt aagcaggcgc    1200
tggaaacagt acagcgcctg ctgcctgtac tgtgccagga tcatggactg accccagacc    1260
aggtagtcgc aatcgcgtcg aacattgggg aaagcaagc cctggaaacc gtgcaaaggt    1320
tgttgccggt cctttgtcaa gaccacggcc ttacaccgga gcaagtcgtg ccattgcaa    1380
ataataacgg tggcaaacag gctcttgaga cggttcagag acttctccca gttctctgtc    1440
aagcccacgg gctgactccc gatcaagttg tagcgattgc gtccaacggt ggagggaaac    1500
aagcattgga gactgtccaa cggctccttc ccgtgttgtg tcaagcccac ggtttgacgc    1560
ctgcacaagt ggtcgccatc gcctcgaatg gcggcggtaa gcaggcgctg gaaacagtac    1620
agcgcctgct gcctgtactg tgccaggatc atggactgaa gagaccggat cccgggcccg    1680
tcgactgcag agg                                                       1693
```

<210> SEQ ID NO 31
<211> LENGTH: 1693
<212> TYPE: DNA
<213> ORGANISM: Artificial Sequence
<220> FEATURE:
<223> OTHER INFORMATION: TAL right arm sequence,T7 RNA binding site, start codon and nuclear localization signal

<400> SEQUENCE: 31

```
atgcatctag agaagacaag aacctgaccc cagaccaggt agtcgcaatc gcgtcacatg      60
```

|  |  |  |  |  |
|---|---|---|---|---|
| acgggggaaa | gcaagccctg | gaaaccgtgc | aaaggttgtt | gccggtcctt | tgtcaagacc | 120 |
| acggccttac | accggagcaa | gtcgtggcca | ttgcatccca | cgacggtggc | aaacaggctc | 180 |
| ttgagacggt | tcagagactt | ctcccagttc | tctgtcaagc | ccacgggctg | actcccgatc | 240 |
| aagttgtagc | gattgcgtcg | catgacgagg | gaaacaagc | attggagact | gtccaacggc | 300 |
| tccttcccgt | gttgtgtcaa | gcccacggtt | tgacgcctgc | acaagtggtc | gccatcgcct | 360 |
| cgaatggcgg | cggtaagcag | gcgctggaaa | cagtacagcg | cctgctgcct | gtactgtgcc | 420 |
| aggatcatgg | actgacccca | gaccaggtag | tcgcaatcgc | gaacaataat | ggggaaagc | 480 |
| aagccctgga | aaccgtgcaa | aggttgttgc | cggtcctttg | tcaagaccac | ggccttacac | 540 |
| cggagcaagt | cgtggccatt | gcaagcaaca | tcggtggcaa | acaggctctt | gagacggttc | 600 |
| agagacttct | cccagttctc | tgtcaagccc | acgggctgac | tcccgatcaa | gttgtagcga | 660 |
| ttgcgtcgca | tgacggaggg | aaacaagcat | tggagactgt | ccaacggctc | cttcccgtgt | 720 |
| tgtgtcaagc | ccacggtttg | acgcctgcac | aagtggtcgc | catcgccagc | catgatggcg | 780 |
| gtaagcaggc | gctggaaaca | gtacagcgcc | tgctgcctgt | actgtgccag | gatcatggac | 840 |
| tgaccccaga | ccaggtagtc | gcaatcgcgt | cgaacattgg | gggaaagcaa | gccctggaaa | 900 |
| ccgtgcaaag | gttgttgccg | gtcctttgtc | aagaccacgg | ccttacaccg | gagcaagtcg | 960 |
| tggccattgc | aagcaatggg | ggtggcaaac | aggctcttga | gacggttcag | agacttctcc | 1020 |
| cagttctctg | tcaagcccac | gggctgactc | cgatcaagt | tgtagcgatt | gcgtcgcatg | 1080 |
| acggagggaa | acaagcattg | gagactgtcc | aacggctcct | tcccgtgttg | tgtcaagccc | 1140 |
| acggtttgac | gcctgcacaa | gtggtcgcca | tcgccagcca | tgatggcggt | aagcaggcgc | 1200 |
| tggaaacagt | acagcgcctg | ctgcctgtac | tgtgccagga | tcatggactg | accccagacc | 1260 |
| aggtagtcgc | aatcgcgtca | catgacgggg | aaagcaagc | cctggaaacc | gtgcaaaggt | 1320 |
| tgttgccggt | cctttgtcaa | gaccacggcc | ttacaccgga | gcaagtcgtg | gccattgcaa | 1380 |
| ataataacgg | tggcaaacag | gctcttgaga | cggttcagag | acttctccca | gttctctgtc | 1440 |
| aagcccacgg | gctgactccc | gatcaagttg | tagcgattgc | gtcgaacatt | ggagggaaac | 1500 |
| aagcattgga | gactgtccaa | cggctccttc | ccgtgttgtg | tcaagcccac | ggtttgacgc | 1560 |
| ctgcacaagt | ggtcgccatc | gccaacaaca | acggcggtaa | gcaggcgctg | aaacagtac | 1620 |
| agcgcctgct | gcctgtactg | tgccaggatc | atggactgaa | gagaccggat | cccgggcccg | 1680 |
| tcgactgcag | agg |  |  |  |  | 1693 |

<210> SEQ ID NO 32
<211> LENGTH: 1698
<212> TYPE: DNA
<213> ORGANISM: Artificial Sequence
<220> FEATURE:
<223> OTHER INFORMATION: Sequence encoding full-length TAL Left Arm

<400> SEQUENCE: 32

|  |  |  |  |  |
|---|---|---|---|---|
| aacctgaccc | cagaccaggt | agtcgcaatc | gcgaacaata | tgggggaaa | gcaagccctg | 60 |
| gaaaccgtgc | aaaggttgtt | gccggtcctt | tgtcaagacc | acggccttac | accggagcaa | 120 |
| gtcgtggcca | ttgcaagcaa | catcggtggc | aaacaggctc | ttgagacggt | tcagagactt | 180 |
| ctcccagttc | tctgtcaagc | ccacgggctg | actcccgatc | aagttgtagc | gattgcgtcg | 240 |
| aacattggag | ggaaacaagc | attggagact | gtccaacggc | tccttcccgt | gttgtgtcaa | 300 |
| gcccacggtt | tgacgcctgc | acaagtggtc | gccatcgcca | caacaacgg | cggtaagcag | 360 |
| gcgctggaaa | cagtacagcg | cctgctgcct | gtactgtgcc | aggatcatgg | actgacccca | 420 |

```
gaccaggtag tcgcaatcgc gtcgaacatt gggggaaagc aagccctgga aaccgtgcaa    480
aggttgttgc cggtcctttg tcaagaccac ggccttacac cggagcaagt cgtggccatt    540
gcatcccacg acggtggcaa acaggctctt gagacggttc agagacttct cccagttctc    600
tgtcaagccc acgggctgac tcccgatcaa gttgtagcga ttgcgtcgaa cattggaggg    660
aaacaagcat ggagactgt ccaacggctc cttcccgtgt tgtgtcaagc ccacggtttg    720
acgcctgcac aagtggtcgc catcgccaac aacaacggcg taagcaggc gctggaaaca    780 gtacagcgcc tgctgcctgt actgtgccag gatcatggac tgaccccaga ccaggtagtc    840
gcaatcgcgt cacatgacgg gggaaagcaa gccctggaaa ccgtgcaaag gttgttgccg    900
gtcctttgtc aagaccacgg ccttacaccg gagcaagtcg tggccattgc aagcaatggg    960
ggtggcaaac aggctcttga cggttcag agacttctcc cagttctctg tcaagcccac    1020
gggctgactc ccgatcaagt tgtagcgatt gcgtcgaaca ttggagggaa caagcattg    1080 gagactgtcc aacggctcct tcccgtgttg tgtcaagccc acggtttgac gcctgcacaa    1140
gtggtcgcca tcgccagcca tgatggcggt aagcaggcgc tggaaacagt acagcgcctg    1200
ctgcctgtac tgtgccagga tcatggactg accccagacc aggtagtcgc aatcgcgtcg    1260
aacattgggg aaagcaagc cctggaaacc gtgcaaaggt tgttgccggt cctttgtcaa    1320
gaccacggcc ttacaccgga gcaagtcgtg gccattgcaa ataataacgg tggcaaacag    1380
gctcttgaga cggttcagag acttctccca gttctctgtc aagcccacgg gctgactccc    1440
gatcaagttg tagcgattgc gtccaacggt ggagggaaac aagcattgga gactgtccaa    1500
cggctccttc ccgtgttgtg tcaagcccac ggtttgacgc ctgcacaagt ggtcgccatc    1560
gcctcgaatg gcggcggtaa gcaggcgctg gaaacagtac agcgcctgct gcctgtactg    1620
tgccaggatc atggactgac cccgaacag gtggtcgcca ttgcttccca cgacggagga    1680
cggccagcct tggagtcc                                                   1698
```

<210> SEQ ID NO 33
<211> LENGTH: 566
<212> TYPE: PRT
<213> ORGANISM: Artificial Sequence
<220> FEATURE:
<223> OTHER INFORMATION: Full-length TAL Left Arm

<400> SEQUENCE: 33

```
Asn Leu Thr Pro Asp Gln Val Val Ala Ile Ala Asn Asn Gly Gly
1               5                   10                  15

Lys Gln Ala Leu Glu Thr Val Gln Arg Leu Leu Pro Val Leu Cys Gln
            20                  25                  30

Asp His Gly Leu Thr Pro Glu Gln Val Val Ala Ile Ala Ser Asn Ile
        35                  40                  45

Gly Gly Lys Gln Ala Leu Glu Thr Val Gln Arg Leu Leu Pro Val Leu
    50                  55                  60

Cys Gln Ala His Gly Leu Thr Pro Asp Gln Val Val Ala Ile Ala Ser
65                  70                  75                  80

Asn Ile Gly Gly Lys Gln Ala Leu Glu Thr Val Gln Arg Leu Leu Pro
                85                  90                  95

Val Leu Cys Gln Ala His Gly Leu Thr Pro Ala Gln Val Val Ala Ile
            100                 105                 110

Ala Asn Asn Asn Gly Gly Lys Gln Ala Leu Glu Thr Val Gln Arg Leu
        115                 120                 125
```

-continued

```
Leu Pro Val Leu Cys Gln Asp His Gly Leu Thr Pro Asp Gln Val Val
            130                 135                 140
Ala Ile Ala Ser Asn Ile Gly Gly Lys Gln Ala Leu Glu Thr Val Gln
145                 150                 155                 160
Arg Leu Leu Pro Val Leu Cys Gln Asp His Gly Leu Thr Pro Glu Gln
                165                 170                 175
Val Val Ala Ile Ala Ser His Asp Gly Gly Lys Gln Ala Leu Glu Thr
            180                 185                 190
Val Gln Arg Leu Leu Pro Val Leu Cys Gln Ala His Gly Leu Thr Pro
        195                 200                 205
Asp Gln Val Val Ala Ile Ala Ser Asn Ile Gly Gly Lys Gln Ala Leu
    210                 215                 220
Glu Thr Val Gln Arg Leu Leu Pro Val Leu Cys Gln Ala His Gly Leu
225                 230                 235                 240
Thr Pro Ala Gln Val Val Ala Ile Ala Asn Asn Gly Gly Lys Gln
                245                 250                 255
Ala Leu Glu Thr Val Gln Arg Leu Leu Pro Val Leu Cys Gln Asp His
            260                 265                 270
Gly Leu Thr Pro Asp Gln Val Val Ala Ile Ala Ser His Asp Gly Gly
        275                 280                 285
Lys Gln Ala Leu Glu Thr Val Gln Arg Leu Leu Pro Val Leu Cys Gln
    290                 295                 300
Asp His Gly Leu Thr Pro Glu Gln Val Val Ala Ile Ala Ser Asn Gly
305                 310                 315                 320
Gly Gly Lys Gln Ala Leu Glu Thr Val Gln Arg Leu Leu Pro Val Leu
                325                 330                 335
Cys Gln Ala His Gly Leu Thr Pro Asp Gln Val Val Ala Ile Ala Ser
            340                 345                 350
Asn Ile Gly Gly Lys Gln Ala Leu Glu Thr Val Gln Arg Leu Leu Pro
        355                 360                 365
Val Leu Cys Gln Ala His Gly Leu Thr Pro Ala Gln Val Val Ala Ile
    370                 375                 380
Ala Ser His Asp Gly Gly Lys Gln Ala Leu Glu Thr Val Gln Arg Leu
385                 390                 395                 400
Leu Pro Val Leu Cys Gln Asp His Gly Leu Thr Pro Asp Gln Val Val
                405                 410                 415
Ala Ile Ala Ser Asn Ile Gly Gly Lys Gln Ala Leu Glu Thr Val Gln
            420                 425                 430
Arg Leu Leu Pro Val Leu Cys Gln Asp His Gly Leu Thr Pro Glu Gln
        435                 440                 445
Val Val Ala Ile Ala Asn Asn Asn Gly Gly Lys Gln Ala Leu Glu Thr
    450                 455                 460
Val Gln Arg Leu Leu Pro Val Leu Cys Gln Ala His Gly Leu Thr Pro
465                 470                 475                 480
Asp Gln Val Val Ala Ile Ala Ser Asn Gly Gly Lys Gln Ala Leu
                485                 490                 495
Glu Thr Val Gln Arg Leu Leu Pro Val Leu Cys Gln Ala His Gly Leu
            500                 505                 510
Thr Pro Ala Gln Val Val Ala Ile Ala Ser Asn Gly Gly Gly Lys Gln
        515                 520                 525
Ala Leu Glu Thr Val Gln Arg Leu Leu Pro Val Leu Cys Gln Asp His
    530                 535                 540
Gly Leu Thr Pro Glu Gln Val Val Ala Ile Ala Ser His Asp Gly Gly
```

```
545                 550                 555                 560

Arg Pro Ala Leu Glu Ser
                565

<210> SEQ ID NO 34
<211> LENGTH: 18
<212> TYPE: DNA
<213> ORGANISM: Artificial Sequence
<220> FEATURE:
<223> OTHER INFORMATION: Mouse chr locus 1, TAL1 target

<400> SEQUENCE: 34
tccctgacca tcccgaga                                                   18

<210> SEQ ID NO 35
<211> LENGTH: 18
<212> TYPE: DNA
<213> ORGANISM: Artificial Sequence
<220> FEATURE:
<223> OTHER INFORMATION: Mouse chr locus 2, TAL1 target

<400> SEQUENCE: 35
tccctgccca ccccgaga                                                   18

<210> SEQ ID NO 36
<211> LENGTH: 18
<212> TYPE: DNA
<213> ORGANISM: Artificial Sequence
<220> FEATURE:
<223> OTHER INFORMATION: Mouse chr locus 1, TAL1 target

<400> SEQUENCE: 36
tccctcccca gcccaaaa                                                   18

<210> SEQ ID NO 37
<211> LENGTH: 18
<212> TYPE: DNA
<213> ORGANISM: Artificial Sequence
<220> FEATURE:
<223> OTHER INFORMATION: Mouse chr locus 10, TAL1 target

<400> SEQUENCE: 37
ttaaaacaac tacagttt                                                   18

<210> SEQ ID NO 38
<211> LENGTH: 18
<212> TYPE: DNA
<213> ORGANISM: Artificial Sequence
<220> FEATURE:
<223> OTHER INFORMATION: Mouse chr locus 1, TAL2 target

<400> SEQUENCE: 38
tgaagacagc tacagttc                                                   18

<210> SEQ ID NO 39
<211> LENGTH: 18
<212> TYPE: DNA
<213> ORGANISM: Artificial Sequence
<220> FEATURE:
<223> OTHER INFORMATION: Mouse chr locus 2, TAL2 target

<400> SEQUENCE: 39
tacaaacagc tcctaatc                                                   18

<210> SEQ ID NO 40
```

```
<211> LENGTH: 18
<212> TYPE: DNA
<213> ORGANISM: Artificial Sequence
<220> FEATURE:
<223> OTHER INFORMATION: Mouse chr locus 1, TAL2 target

<400> SEQUENCE: 40
taaaaacagc aacagcaa                                                    18

<210> SEQ ID NO 41
<211> LENGTH: 18
<212> TYPE: DNA
<213> ORGANISM: Artificial Sequence
<220> FEATURE:
<223> OTHER INFORMATION: Mouse chr locus 10, TAL2 target

<400> SEQUENCE: 41
tgccaacacc cacatctc                                                    18

<210> SEQ ID NO 42
<211> LENGTH: 20
<212> TYPE: PRT
<213> ORGANISM: Artificial Sequence
<220> FEATURE:
<223> OTHER INFORMATION: portion of Crb mutant protein sequence showing
      region of the rd8 mutation

<400> SEQUENCE: 42

Cys Glu Asp Ser Tyr Ser Ser Tyr Gly Val Pro Val Cys Arg Asp Gly
1               5                   10                  15

Gln Gly His Thr
            20

<210> SEQ ID NO 43
<211> LENGTH: 63
<212> TYPE: DNA
<213> ORGANISM: Artificial Sequence
<220> FEATURE:
<223> OTHER INFORMATION: nucleic acid sequence encoding portion of Crb
      mutant protein sequence showing region of the rd8 mutation in
      SEQ ID NO:42

<400> SEQUENCE: 43
aactgtgaag acagctacag ttcttatggt gtgcctgtct ctcgggatgg tcagggacac      60
act                                                                    63

<210> SEQ ID NO 44
<211> LENGTH: 64
<212> TYPE: DNA
<213> ORGANISM: Artificial Sequence
<220> FEATURE:
<223> OTHER INFORMATION: portion of donor oligonucleotides SEQ ID NOs:
      1 and 3 and sequence present in genetically engineered mice with
      corrected Crb1rd8

<400> SEQUENCE: 44
aactgtgaag acagttacag cagttatcgg tgtgcctgtc tgtcgggatg gtcagggaca      60
cact                                                                   64

<210> SEQ ID NO 45
<211> LENGTH: 21
<212> TYPE: PRT
<213> ORGANISM: Artificial Sequence
<220> FEATURE:
<223> OTHER INFORMATION: Portion of Crb1 amino acid sequence in wild-
      type and corrected animals
```

<400> SEQUENCE: 45

Asn Cys Glu Asp Ser Tyr Ser Ser Tyr Arg Cys Ala Cys Leu Ser Gly
1               5                   10                  15

Trp Ser Gly Thr His
            20

<210> SEQ ID NO 46
<211> LENGTH: 64
<212> TYPE: DNA
<213> ORGANISM: Artificial Sequence
<220> FEATURE:
<223> OTHER INFORMATION: DNA sequence encoding a portion of wild-type
      Crb1

<400> SEQUENCE: 46
aactgtgaag acagctacag ttcttatcgg tgtgcctgtc tctcgggatg gtcagggaca    60
cact                                                                64

<210> SEQ ID NO 47
<211> LENGTH: 16
<212> TYPE: DNA
<213> ORGANISM: Artificial Sequence
<220> FEATURE:
<223> OTHER INFORMATION: Intervening sequence

<400> SEQUENCE: 47
ttatggtgtg cctgtc                                                   16

<210> SEQ ID NO 48
<211> LENGTH: 18
<212> TYPE: DNA
<213> ORGANISM: Artificial Sequence
<220> FEATURE:
<223> OTHER INFORMATION: Binds to right side TAL

<400> SEQUENCE: 48
tctcgggatg gtcaggga                                                 18

<210> SEQ ID NO 49
<211> LENGTH: 24
<212> TYPE: DNA
<213> ORGANISM: Artificial Sequence
<220> FEATURE:
<223> OTHER INFORMATION: forward PCR primer

<400> SEQUENCE: 49
gggaaagctt cccagactga caat                                          24

<210> SEQ ID NO 50
<211> LENGTH: 24
<212> TYPE: DNA
<213> ORGANISM: Artificial Sequence
<220> FEATURE:
<223> OTHER INFORMATION: reverse PCR primer

<400> SEQUENCE: 50
cgaccagaca ccctttgtga taag                                          24

<210> SEQ ID NO 51
<211> LENGTH: 22
<212> TYPE: DNA
<213> ORGANISM: Artificial Sequence
<220> FEATURE:
<223> OTHER INFORMATION: forward PCR primer

<400> SEQUENCE: 51
cagacaggca caccgataac tg                                              22

<210> SEQ ID NO 52
<211> LENGTH: 34
<212> TYPE: DNA
<213> ORGANISM: Artificial Sequence
<220> FEATURE:
<223> OTHER INFORMATION: reverse complement of a portion of SEQ ID NO:43

<400> SEQUENCE: 52
gagagacagg cacaccataa gaactgtagc tgtc                                 34

<210> SEQ ID NO 53
<211> LENGTH: 35
<212> TYPE: DNA
<213> ORGANISM: Artificial Sequence
<220> FEATURE:
<223> OTHER INFORMATION: reverse complement of a portion of SEQ ID NO:44

<400> SEQUENCE: 53
gacagacagg cacacggata actgctgtaa ctgtc                                35

<210> SEQ ID NO 54
<211> LENGTH: 3006
<212> TYPE: DNA
<213> ORGANISM: Artificial Sequence
<220> FEATURE:
<223> OTHER INFORMATION: Sequence encoding TAL Left Arm + FokI monomer

<400> SEQUENCE: 54

| atggactaca aagaccatga cggtgattat aaagatcatg acatcgatta caaggatgac | 60 |
| gatgacaaga tggcccccaa gaagaagagg aaggtgggca ttcaccgcgg ggtacctatg | 120 |
| gtggacttga ggacactcgg ttattcgcaa cagcaacagg agaaaatcaa gcctaaggtc | 180 |
| aggagcaccg tcgcgcaaca ccacgaggcg cttgtggggc atggcttcac tcatgcgcat | 240 |
| attgtcgcgc tttcacagca ccctgcggcg cttgggacgg tggctgtcaa ataccaagat | 300 |
| atgattgcgg ccctgcccga agccacgcac gaggcaattg taggggtcgg taaacagtgg | 360 |
| tcgggagcgc gagcacttga ggcgctgctg actgtggcgg gtgagcttag ggggcctccg | 420 |
| ctccagctcg acaccgggca gctgctgaag atcgcgaaga gaggggagt aacagcggta | 480 |
| gaggcagtgc acgcctggcg caatgcgctc accggggccc ccttgaacct gaccccagac | 540 |
| caggtagtcg caatcgcgaa caataatggg ggaaagcaag ccctggaaac cgtgcaaagg | 600 |
| ttgttgccgg tcctttgtca agaccacggc cttaccggg agcaagtcgt ggccattgca | 660 |
| agcaacatcg gtggcaaaca ggctcttgag acgttcaga gacttctccc agttctctgt | 720 |
| caagcccacg ggctgactcc cgatcaagtt gtagcgattg cgtcgaacat tggagggaaa | 780 |
| caagcattgg agactgtcca acggctcctt cccgtgttgt gtcaagccca cggttttacg | 840 |
| cctgcacaag tggtcgccat cgccaacaac aacggcggta agcaggcgct ggaaacagta | 900 |
| cagcgcctgc tgcctgtact gtgccaggat catggactga ccccagacca ggtagtcgca | 960 |
| atcgcgtcga acattggggg aaagcaagcc ctggaaaccg tgcaaggtt gttgccggtc | 1020 |
| ctttgtcaag accacggcct tacaccggag caagtcgtgg ccattgcatc ccacgacggt | 1080 |
| ggcaaacagg ctcttgagac ggttcagaga cttctcccag ttctctgtca gcccacgggg | 1140 |
| ctgactcccg atcaagttgt agcgattgcg tcgaacattg gagggaaaca agcattggag | 1200 |

```
actgtccaac ggctccttcc cgtgttgtgt caagcccacg gtttgacgcc tgcacaagtg    1260
gtcgccatcg ccaacaacaa cggcggtaag caggcgctgg aaacagtaca gcgcctgctg    1320
cctgtactgt gccaggatca tggactgacc ccagaccagg tagtcgcaat cgcgtcacat    1380
gacgggggaa agcaagccct ggaaaccgtg caaaggttgt tgccggtcct ttgtcaagac    1440
cacggcctta caccggagca agtcgtggcc attgcaagca atggggtgg caaacaggct     1500 cttgagacgg ttcagagact tctcccagtt ctctgtcaag cccacgggct gactcccgat    1560
caagttgtag cgattgcgtc gaacattgga gggaaacaag cattggagac tgtccaacgg    1620
ctccttcccg tgttgtgtca agcccacggt ttgacgcctg cacaagtggt cgccatcgcc    1680
agccatgatg gcggtaagca ggcgctggaa acagtacagc gcctgctgcc tgtactgtgc    1740
caggatcatg gactgacccc agaccaggta gtcgcaatcg cgtcgaacat gggggaaag    1800 caagccctgg aaaccgtgca aaggttgttg ccggtccttt gtcaagacca cggccttaca    1860
ccggagcaag tcgtggccat tgcaaataat aacggtggca acaggctct tgagacggtt    1920 cagagacttc tcccagttct ctgtcaagcc cacgggctga ctcccgatca agttgtagcg    1980
attgcgtcca acggtggagg gaaacaagca ttggagactg tccaacggct ccttcccgtg    2040
ttgtgtcaag cccacggttt gacgcctgca caagtggtcg ccatcgcctc gaatggcggc    2100
ggtaagcagg cgctggaaac agtacagcgc ctgctgcctg tactgtgcca ggatcatgga    2160
ctgacacccg aacaggtggt cgccattgct tcccacgacg gaggacgcc agccttggag     2220 tccatcgtag cccaattgtc caggcccgat cccgcgttgg ctgcgttaac gaatgaccat    2280
ctggtggcgt tggcatgtct tggtggacga cccgcgctcg atgcagtcaa aaagggtctg    2340
cctcatgctc ccgcattgat caaaagaacc aaccggcgga ttcccgagag aacttcccat    2400
cgagtcgcgg gatcccaact agtcaaaagt gaactggagg agaagaaatc tgaacttcgt    2460
cataaattga aatatgtgcc tcatgaatat attgaattaa ttgaaattgc cagaaattcc    2520
actcaggata gaattcttga aatgaaggta atggaatttt ttatgaaagt ttatggatat    2580
agaggtaaac atttgggtgg atcaaggaaa ccggacggag caatttatac tgtcggatct    2640
cctattgatt acggtgtgat cgtggatact aaagcttata gcggaggtta taatctgcca    2700
attggccaag cagatgaaat gcaacgatat gtcgaagaaa atcaaacacg aaacaaacat    2760
atcaacccta tgaatggtg gaaagtctat ccatcttctg taacggaatt taagttttta    2820
tttgtgagtg gtcactttaa aggaaactac aaagctcagc ttacacgatt aaatcatatc    2880
actaattgta atggagctgt tcttagtgta gaagagcttt taattggtgg agaaatgatt    2940
aaagccggca cattaacctt agaggaagtc agacggaaat ttaataacgg cgagataaac    3000
ttttaa                                                               3006
```

<210> SEQ ID NO 55
<211> LENGTH: 23
<212> TYPE: DNA
<213> ORGANISM: Artificial Sequence
<220> FEATURE:
<223> OTHER INFORMATION: Primer for SNP assay for illegitimate
      recombinations

<400> SEQUENCE: 55
cagcccctgt ttgcatggag gaa                                              23

<210> SEQ ID NO 56
<211> LENGTH: 20
<212> TYPE: DNA

<213> ORGANISM: Artificial Sequence
<220> FEATURE:
<223> OTHER INFORMATION: Crb1rb8 wt sequence
<220> FEATURE:
<221> NAME/KEY: misc_feature
<222> LOCATION: (6)..(6)
<223> OTHER INFORMATION: s is G or C

<400> SEQUENCE: 56
cccgasagac aggcacacca                                          20

<210> SEQ ID NO 57
<211> LENGTH: 19
<212> TYPE: DNA
<213> ORGANISM: Artificial Sequence
<220> FEATURE:
<223> OTHER INFORMATION: single stranded ODN modified sequence
<220> FEATURE:
<221> NAME/KEY: misc_feature
<222> LOCATION: (5)..(5)
<223> OTHER INFORMATION: s is G or C

<400> SEQUENCE: 57
ccgasagaca ggcacaccg                                           19

<210> SEQ ID NO 58
<211> LENGTH: 3006
<212> TYPE: DNA
<213> ORGANISM: Artificial Sequence
<220> FEATURE:
<223> OTHER INFORMATION: Sequence encoding TAL Right Arm + FokI monomer

<400> SEQUENCE: 58
atggactaca aagaccatga cggtgattat aaagatcatg acatcgatta caaggatgac      60
gatgacaaga tggccccccaa gaagaagagg aaggtgggca ttcaccgcgg ggtacctatg    120
gtggacttga ggacactcgg ttattcgcaa cagcaacagg agaaaatcaa gcctaaggtc    180
aggagcaccg tcgcgcaaca ccacgaggcg cttgtgggc atggcttcac tcatgcgcat     240
attgtcgcgc tttcacagca ccctgcggcg cttgggacgg tggctgtcaa ataccaagat    300
atgattgcgg ccctgcccga agccacgcac gaggcaattg taggggtcgg taaacagtgg    360
tcgggagcgc gagcacttga ggcgctgctg actgtggcgg gtgagcttag ggggcctcca    420
ctccagctcg acaccgggca gctgctgaag atcgcgaaga gaggggggagt aacagcggta    480 gaggcagtgc acgcctggcg caatgcgctc accggggccc ccttgaacct gaccccagac    540
caggtagtcg caatcgcgtc acatgacggg ggaaagcaag ccctggaaac cgtgcaaagg    600
ttgttgccgg tcctttgtca agaccacggc cttacaccgg agcaagtcgt ggccattgca    660
tcccacgacg gtggcaaaca ggctcttgag acgttcaga gacttctccc agttctctgt    720
caagcccacg ggctgactcc cgatcaagtt gtagcgattg cgtcgcatga cggagggaaa    780
caagcattgg agactgtcca acggctcctt cccgtgttgt gtcaagccca cggtttgacg    840
cctgcacaag tggtcgccat cgcctcgaat ggcggcggta agcaggcgct ggaaacagta    900
cagcgcctgc tgcctgtact gtgccaggat catggactga ccccagacca ggtagtcgca    960
atcgcgaaca ataatggggg aaagcaagcc tggaaaccg tgcaaaggtt gttgccggtc   1020
ctttgtcaag accacggcct tacaccggag caagtcgtgg ccattgcaag caacatcggt   1080
ggcaaacagg ctcttgagac ggttcagaga cttctcccag ttctctgtca gcccacggg   1140 ctgactcccg atcaagttgt agcgattgcg tcgcatgacg agggaaaca agcattggag    1200 actgtccaac ggctccttcc cgtgttgtgt caagcccacg gtttgacgcc tgcacaagtg   1260

```
gtcgccatcg ccagccatga tggcggtaag caggcgctgg aaacagtaca gcgcctgctg    1320
cctgtactgt gccaggatca tggactgacc ccagaccagg tagtcgcaat cgcgtcgaac    1380
attgggggaa agcaagccct ggaaaccgtg caaaggttgt tgccggtcct tgtcaagac     1440 cacggcctta caccggagca agtcgtggcc attgcaagca atgggggtgg caaacaggct    1500
cttgagacgg ttcagagact tctcccagtt ctctgtcaag cccacgggct gactcccgat    1560
caagttgtag cgattgcgtc gcatgacgga gggaaacaag cattggagac tgtccaacgg    1620
ctccttcccg tgttgtgtca agcccacggt tgacgcctg cacaagtggt cgccatcgcc     1680
agccatgatg gcgtaagca ggcgctggaa acagtacagc gcctgctgcc tgtactgtgc     1740
caggatcatg gactgacccc agaccaggta gtcgcaatcg cgtcacatga cggggaaag    1800 caagccctgg aaaccgtgca aaggttgttg ccggtccttt gtcaagacca cggccttaca    1860
ccggagcaag tcgtggccat tgcaataat aacggtggca acaggctct tgagacggtt      1920 cagagacttc tcccagttct ctgtcaagcc cacgggctga ctcccgatca agttgtagcg    1980
attgcgtcga acattggagg gaaacaagca ttggagactg ccaacggct ccttcccgtg     2040 ttgtgtcaag cccacggttt gacgcctgca caagtggtcg ccatcgccaa caacaacggc    2100
ggtaagcagg cgctggaaac agtacagcgc ctgctgcctg tactgtgcca ggatcatgga    2160
ctgacacccg aacaggtggt cgccattgct ctaacatcg gaggacggcc agccttggag     2220
tccatcgtag cccaattgtc caggcccgat cccgcgttgg ctgcgttaac gaatgaccat    2280
ctggtggcgt tggcatgtct tggtggacga cccgcgctcg atgcagtcaa aaagggtctg    2340
cctcatgctc ccgcattgat caaaagaacc aaccggcgga ttcccgagag aacttcccat    2400
cgagtcgcgg gatcccaact agtcaaaagt gaactggagg agaagaaatc tgaacttcgt    2460
cataaattga aatatgtgcc tcatgaatat attgaattaa ttgaaattgc cagaaattcc    2520
actcaggata gaattcttga atgaaggta atggaatttt ttatgaaagt ttatggatat     2580
agaggtaaac atttgggtgg atcaaggaaa ccggacggag caatttatac tgtcggatct    2640
cctattgatt acggtgtgat cgtggatact aaagcttata gcggaggtta taatctgcca    2700
attggccaag cagatgaaat gcaacgatat gtcgaagaaa atcaaacacg aaacaaacat    2760 atcaaccccta atgaatggtg gaaagtctat ccatcttctg taacggaatt taagttttta    2820
tttgtgagtg gtcactttaa aggaaactac aaagctcagc ttacacgatt aaatcatatc    2880
actaattgta atggagctgt tcttagtgta gaagagcttt taattggtgg agaaatgatt    2940
aaagccggca cattaacctt agaggaagtc agacggaaat ttaataacgg cgagataaac    3000
tttttaa                                                              3006
```

<210> SEQ ID NO 59
<211> LENGTH: 1001
<212> TYPE: PRT
<213> ORGANISM: Artificial Sequence
<220> FEATURE:
<223> OTHER INFORMATION: TAL Left Arm + FokI monomer amino acid sequence

<400> SEQUENCE: 59

```
Met Asp Tyr Lys Asp His Asp Gly Asp Tyr Lys Asp His Asp Ile Asp
 1               5                  10                  15

Tyr Lys Asp Asp Asp Asp Lys Met Ala Pro Lys Lys Lys Arg Lys Val
            20                  25                  30

Gly Ile His Arg Gly Val Pro Met Val Asp Leu Arg Thr Leu Gly Tyr
        35                  40                  45
```

```
Ser Gln Gln Gln Gln Glu Lys Ile Lys Pro Lys Val Arg Ser Thr Val
    50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Val Thr Val Ala Val
                    85                  90                  95

Lys Tyr Gln Asp Met Ile Ala Ala Leu Pro Glu Ala Thr His Glu Ala
                100                 105                 110

Ile Val Gly Val Gly Lys Gln Trp Ser Gly Ala Arg Ala Leu Glu Ala
                115                 120                 125

Leu Leu Thr Val Ala Gly Glu Leu Arg Gly Pro Pro Leu Gln Leu Asp
130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Asp Gln Val Ala Ile Ala Asn Asn Asn Gly Gly Lys
                180                 185                 190

Gln Ala Leu Glu Thr Val Gln Arg Leu Leu Pro Val Leu Cys Gln Asp
                195                 200                 205

His Gly Leu Thr Pro Glu Gln Val Val Ala Ile Ala Ser Asn Ile Gly
                210                 215                 220

Gly Lys Gln Ala Leu Glu Thr Val Gln Arg Leu Leu Pro Val Leu Cys
225                 230                 235                 240

Gln Ala His Gly Leu Thr Pro Asp Gln Val Val Ala Ile Ala Ser Asn
                245                 250                 255

Ile Gly Gly Lys Gln Ala Leu Glu Thr Val Gln Arg Leu Leu Pro Val
                260                 265                 270

Leu Cys Gln Ala His Gly Leu Thr Pro Ala Gln Val Val Ala Ile Ala
                275                 280                 285

Asn Asn Asn Gly Gly Lys Gln Ala Leu Glu Thr Val Gln Arg Leu Leu
290                 295                 300

Pro Val Leu Cys Gln Asp His Gly Leu Thr Pro Asp Gln Val Val Ala
305                 310                 315                 320

Ile Ala Ser Asn Ile Gly Gly Lys Gln Ala Leu Glu Thr Val Gln Arg
                325                 330                 335

Leu Leu Pro Val Leu Cys Gln Asp His Gly Leu Thr Pro Glu Gln Val
                340                 345                 350

Val Ala Ile Ala Ser His Asp Gly Gly Lys Gln Ala Leu Glu Thr Val
                355                 360                 365

Gln Arg Leu Leu Pro Val Leu Cys Gln Ala His Gly Leu Thr Pro Asp
                370                 375                 380

Gln Val Val Ala Ile Ala Ser Asn Ile Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Ala Gln Val Val Ala Ile Ala Asn Asn Asn Gly Gly Lys Gln Ala
                420                 425                 430

Leu Glu Thr Val Gln Arg Leu Leu Pro Val Leu Cys Gln Asp His Gly
                435                 440                 445

Leu Thr Pro Asp Gln Val Val Ala Ile Ala Ser His Asp Gly Gly Lys
450                 455                 460
```

-continued

Gln Ala Leu Glu Thr Val Gln Arg Leu Leu Pro Val Leu Cys Gln Asp
465                 470                 475                 480

His Gly Leu Thr Pro Glu Gln Val Val Ala Ile Ala Ser Asn Gly Gly
            485                 490                 495

Gly Lys Gln Ala Leu Glu Thr Val Gln Arg Leu Leu Pro Val Leu Cys
                500                 505                 510

Gln Ala His Gly Leu Thr Pro Asp Gln Val Val Ala Ile Ala Ser Asn
            515                 520                 525

Ile Gly Gly Lys Gln Ala Leu Glu Thr Val Gln Arg Leu Leu Pro Val
        530                 535                 540

Leu Cys Gln Ala His Gly Leu Thr Pro Ala Gln Val Val Ala Ile Ala
545                 550                 555                 560

Ser His Asp Gly Gly Lys Gln Ala Leu Glu Thr Val Gln Arg Leu Leu
            565                 570                 575

Pro Val Leu Cys Gln Asp His Gly Leu Thr Pro Asp Gln Val Val Ala
                580                 585                 590

Ile Ala Ser Asn Ile Gly Gly Lys Gln Ala Leu Glu Thr Val Gln Arg
        595                 600                 605

Leu Leu Pro Val Leu Cys Gln Asp His Gly Leu Thr Pro Glu Gln Val
610                 615                 620

Val Ala Ile Ala Asn Asn Asn Gly Gly Lys Gln Ala Leu Glu Thr Val
625                 630                 635                 640

Gln Arg Leu Leu Pro Val Leu Cys Gln Ala His Gly Leu Thr Pro Asp
            645                 650                 655

Gln Val Val Ala Ile Ala Ser Asn Gly Gly Gly Lys Gln Ala Leu Glu
                660                 665                 670

Thr Val Gln Arg Leu Leu Pro Val Leu Cys Gln Ala His Gly Leu Thr
        675                 680                 685

Pro Ala Gln Val Val Ala Ile Ala Ser Asn Gly Gly Gly Lys Gln Ala
690                 695                 700

Leu Glu Thr Val Gln Arg Leu Leu Pro Val Leu Cys Gln Asp His Gly
705                 710                 715                 720

Leu Thr Pro Glu Gln Val Val Ala Ile Ala Ser His Asp Gly Gly Arg
            725                 730                 735

Pro Ala Leu Glu Ser Ile Val Ala Gln Leu Ser Arg Pro Asp Pro Ala
                740                 745                 750

Leu Ala Ala Leu Thr Asn Asp His Leu Val Ala Leu Ala Cys Leu Gly
        755                 760                 765

Gly Arg Pro Ala Leu Asp Ala Val Lys Lys Gly Leu Pro His Ala Pro
770                 775                 780

Ala Leu Ile Lys Arg Thr Asn Arg Arg Ile Pro Glu Arg Thr Ser His
785                 790                 795                 800

Arg Val Ala Gly Ser Gln Leu Val Lys Ser Glu Leu Glu Glu Lys Lys
            805                 810                 815

Ser Glu Leu Arg His Lys Leu Lys Tyr Val Pro His Glu Tyr Ile Glu
                820                 825                 830

Leu Ile Glu Ile Ala Arg Asn Ser Thr Gln Asp Arg Ile Leu Glu Met
        835                 840                 845

Lys Val Met Glu Phe Phe Met Lys Val Tyr Gly Tyr Arg Gly Lys His
850                 855                 860

Leu Gly Gly Ser Arg Lys Pro Asp Gly Ala Ile Tyr Thr Val Gly Ser
865                 870                 875                 880

Pro Ile Asp Tyr Gly Val Ile Val Asp Thr Lys Ala Tyr Ser Gly Gly

```
                    885                 890                 895
Tyr Asn Leu Pro Ile Gly Gln Ala Asp Glu Met Gln Arg Tyr Val Glu
                900                 905                 910

Glu Asn Gln Thr Arg Asn Lys His Ile Asn Pro Asn Glu Trp Trp Lys
            915                 920                 925

Val Tyr Pro Ser Ser Val Thr Glu Phe Lys Phe Leu Phe Val Ser Gly
        930                 935                 940

His Phe Lys Gly Asn Tyr Lys Ala Gln Leu Thr Arg Leu Asn His Ile
945                 950                 955                 960

Thr Asn Cys Asn Gly Ala Val Leu Ser Val Glu Glu Leu Leu Ile Gly
                965                 970                 975

Gly Glu Met Ile Lys Ala Gly Thr Leu Thr Leu Glu Glu Val Arg Arg
                980                 985                 990

Lys Phe Asn Asn Gly Glu Ile Asn  Phe
                995                 1000

<210> SEQ ID NO 60
<211> LENGTH: 1001
<212> TYPE: PRT
<213> ORGANISM: Artificial Sequence
<220> FEATURE:
<223> OTHER INFORMATION: TAL Right Arm + FokI monomer amino acid
      sequence

<400> SEQUENCE: 60

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Lys Arg Lys Val
                20                  25                  30

Gly Ile His Arg Gly Val Pro Met Val Asp Leu Arg Thr Leu Gly Tyr
            35                  40                  45

Ser Gln Gln Gln Glu Lys Ile Lys Pro Lys Val Arg Ser Thr Val
50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
                100                 105                 110

Ile Val Gly Val Gly Lys Gln Trp Ser Gly Ala Arg Ala Leu Glu Ala
            115                 120                 125

Leu Leu Thr Val Ala Gly Glu Leu Arg Gly Pro Pro Leu Gln Leu Asp
        130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Asp Gln Val Val Ala Ile Ala Ser His Asp Gly Gly Lys
                180                 185                 190

Gln Ala Leu Glu Thr Val Gln Arg Leu Leu Pro Val Leu Cys Gln Asp
            195                 200                 205

His Gly Leu Thr Pro Glu Gln Val Val Ala Ile Ala Ser His Asp Gly
        210                 215                 220

Gly Lys Gln Ala Leu Glu Thr Val Gln Arg Leu Leu Pro Val Leu Cys
225                 230                 235                 240
```

```
Gln Ala His Gly Leu Thr Pro Asp Gln Val Val Ala Ile Ala Ser His
            245                 250                 255

Asp Gly Gly Lys Gln Ala Leu Glu Thr Val Gln Arg Leu Leu Pro Val
        260                 265                 270

Leu Cys Gln Ala His Gly Leu Thr Pro Ala Gln Val Val Ala Ile Ala
    275                 280                 285

Ser Asn Gly Gly Lys Gln Ala Leu Glu Thr Val Gln Arg Leu Leu
290                 295                 300

Pro Val Leu Cys Gln Asp His Gly Leu Thr Pro Asp Gln Val Val Ala
305                 310                 315                 320

Ile Ala Asn Asn Asn Gly Gly Lys Gln Ala Leu Glu Thr Val Gln Arg
                325                 330                 335

Leu Leu Pro Val Leu Cys Gln Asp His Gly Leu Thr Pro Glu Gln Val
            340                 345                 350

Val Ala Ile Ala Ser Asn Ile Gly Gly Lys Gln Ala Leu Glu Thr Val
            355                 360                 365

Gln Arg Leu Leu Pro Val Leu Cys Gln Ala His Gly Leu Thr Pro Asp
    370                 375                 380

Gln Val Val Ala Ile Ala Ser His Asp Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Ala Gln Val Val Ala Ile Ala Ser His Asp Gly Gly Lys Gln Ala
            420                 425                 430

Leu Glu Thr Val Gln Arg Leu Leu Pro Val Leu Cys Gln Asp His Gly
        435                 440                 445

Leu Thr Pro Asp Gln Val Val Ala Ile Ala Ser Asn Ile Gly Gly Lys
    450                 455                 460

Gln Ala Leu Glu Thr Val Gln Arg Leu Leu Pro Val Leu Cys Gln Asp
465                 470                 475                 480

His Gly Leu Thr Pro Glu Gln Val Val Ala Ile Ala Ser Asn Gly Gly
                485                 490                 495

Gly Lys Gln Ala Leu Glu Thr Val Gln Arg Leu Leu Pro Val Leu Cys
            500                 505                 510

Gln Ala His Gly Leu Thr Pro Asp Gln Val Val Ala Ile Ala Ser His
        515                 520                 525

Asp Gly Gly Lys Gln Ala Leu Glu Thr Val Gln Arg Leu Leu Pro Val
    530                 535                 540

Leu Cys Gln Ala His Gly Leu Thr Pro Ala Gln Val Val Ala Ile Ala
545                 550                 555                 560

Ser His Asp Gly Gly Lys Gln Ala Leu Glu Thr Val Gln Arg Leu Leu
                565                 570                 575

Pro Val Leu Cys Gln Asp His Gly Leu Thr Pro Asp Gln Val Val Ala
            580                 585                 590

Ile Ala Ser His Asp Gly Gly Lys Gln Ala Leu Glu Thr Val Gln Arg
        595                 600                 605

Leu Leu Pro Val Leu Cys Gln Asp His Gly Leu Thr Pro Glu Gln Val
    610                 615                 620

Val Ala Ile Ala Asn Asn Asn Gly Gly Lys Gln Ala Leu Glu Thr Val
625                 630                 635                 640

Gln Arg Leu Leu Pro Val Leu Cys Gln Ala His Gly Leu Thr Pro Asp
                645                 650                 655

Gln Val Val Ala Ile Ala Ser Asn Ile Gly Gly Lys Gln Ala Leu Glu
```

```
                   660                665                670
Thr Val Gln Arg Leu Leu Pro Val Leu Cys Gln Ala His Gly Leu Thr
                675                680                685
Pro Ala Gln Val Val Ala Ile Ala Asn Asn Asn Gly Gly Lys Gln Ala
            690                695                700
Leu Glu Thr Val Gln Arg Leu Leu Pro Val Leu Cys Gln Asp His Gly
705                710                715                720
Leu Thr Pro Glu Gln Val Val Ala Ile Ala Ser Asn Ile Gly Gly Arg
                725                730                735
Pro Ala Leu Glu Ser Ile Val Ala Gln Leu Ser Arg Pro Asp Pro Ala
            740                745                750
Leu Ala Ala Leu Thr Asn Asp His Leu Val Ala Leu Ala Cys Leu Gly
            755                760                765
Gly Arg Pro Ala Leu Asp Ala Val Lys Lys Gly Leu Pro His Ala Pro
        770                775                780
Ala Leu Ile Lys Arg Thr Asn Arg Arg Ile Pro Glu Arg Thr Ser His
785                790                795                800
Arg Val Ala Gly Ser Gln Leu Val Lys Ser Glu Leu Glu Glu Lys Lys
                805                810                815
Ser Glu Leu Arg His Lys Leu Lys Tyr Val Pro His Glu Tyr Ile Glu
                820                825                830
Leu Ile Glu Ile Ala Arg Asn Ser Thr Gln Asp Arg Ile Leu Glu Met
            835                840                845
Lys Val Met Glu Phe Phe Met Lys Val Tyr Gly Tyr Arg Gly Lys His
850                855                860
Leu Gly Gly Ser Arg Lys Pro Asp Gly Ala Ile Tyr Thr Val Gly Ser
865                870                875                880
Pro Ile Asp Tyr Gly Val Ile Val Asp Thr Lys Ala Tyr Ser Gly Gly
                885                890                895
Tyr Asn Leu Pro Ile Gly Gln Ala Asp Glu Met Gln Arg Tyr Val Glu
                900                905                910
Glu Asn Gln Thr Arg Asn Lys His Ile Asn Pro Asn Glu Trp Trp Lys
            915                920                925
Val Tyr Pro Ser Ser Val Thr Glu Phe Lys Phe Leu Phe Val Ser Gly
        930                935                940
His Phe Lys Gly Asn Tyr Lys Ala Gln Leu Thr Arg Leu Asn His Ile
945                950                955                960
Thr Asn Cys Asn Gly Ala Val Leu Ser Val Glu Glu Leu Leu Ile Gly
            965                970                975
Gly Glu Met Ile Lys Ala Gly Thr Leu Thr Leu Glu Glu Val Arg Arg
            980                985                990
Lys Phe Asn Asn Gly Glu Ile Asn Phe
        995                1000

<210> SEQ ID NO 61
<211> LENGTH: 1698
<212> TYPE: DNA
<213> ORGANISM: Artificial Sequence
<220> FEATURE:
<223> OTHER INFORMATION: Sequence encoding full-length TAL Right Arm

<400> SEQUENCE: 61
aacctgaccc cagaccaggt agtcgcaatc gcgaacaata tgggggaaa gcaagccctg      60 gaaaccgtgc aaaggttgtt gccggtcctt tgtcaagacc acggccttac accggagcaa     120
```

```
gtcgtggcca ttgcaagcaa catcggtggc aaacaggctc ttgagacggt tcagagactt    180
ctcccagttc tctgtcaagc ccacgggctg actcccgatc aagttgtagc gattgcgtcg    240
aacattggag ggaaacaagc attggagact gtccaacggc tccttcccgt gttgtgtcaa    300
gcccacggtt tgacgcctgc acaagtggtc gccatcgcca acaacaacgg cggtaagcag    360
gcgctggaaa cagtacagcg cctgctgcct gtactgtgcc aggatcatgg actgacccca    420
gaccaggtag tcgcaatcgc gtcgaacatt ggggggaaagc aagccctgga aaccgtgcaa    480
aggttgttgc cggtcctttg tcaagaccac ggccttacac cggagcaagt cgtggccatt    540
gcatcccacg acggtggcaa acaggctctt gagacggttc agagacttct cccagttctc    600
tgtcaagccc acgggctgac tcccgatcaa gttgtagcga ttgcgtcgaa cattggaggg    660
aaacaagcat ggagactgt ccaacggctc cttcccgtgt tgtgtcaagc ccacggtttg    720
acgcctgcac aagtggtcgc catcgccaac aacaacggcg gtaagcaggc gctggaaaca    780
gtacagcgcc tgctgcctgt actgtgccag gatcatggac tgaccccaga ccaggtagtc    840
gcaatcgcgt cacatgacgg ggaaagcaa gccctggaaa ccgtgcaaag gttgttgccg    900
gtcctttgtc aagaccacgg ccttacaccg gagcaagtcg tggccattgc aagcaatggg    960
ggtggcaaac aggctcttga cacggttcag agacttctcc cagttctctg tcaagcccac   1020
gggctgactc ccgatcaagt tgtagcgatt gcgtcgaaca ttggagggaa caagcattg   1080 gagactgtcc aacggctcct tcccgtgttg tgtcaagccc acggtttgac gcctgcacaa   1140
gtggtcgcca tcgccagcca tgatggcggt aagcaggcgc tggaaacagt acagcgcctg   1200
ctgcctgtac tgtgccagga tcatggactg accccagacc aggtagtcgc aatcgcgtcg   1260
aacattgggg gaaagcaagc cctggaaacc gtgcaaaggt tgttgccggt cctttgtcaa   1320
gaccacggcc ttacaccgga gcaagtcgtg gccattgcaa ataataacgg tgcaaacag   1380 gctcttgaga cggttcagag acttctccca gttctctgtc aagcccacgg gctgactccc   1440
gatcaagttg tagcgattgc gtccaacggt ggagggaaac aagcattgga gactgtccaa   1500
cggctccttc ccgtgttgtg tcaagcccac ggtttgacgc ctgcacaagt ggtcgccatc   1560
gcctcgaatg gcggcggtaa gcaggcgctg gaaacagtac agcgcctgct gcctgtactg   1620
tgccaggatc atggactgac cccgaacag gtggtcgcca ttgcttccca cgacggagga   1680
cggccagcct tggagtcc                                                  1698

<210> SEQ ID NO 62
<211> LENGTH: 566
<212> TYPE: PRT
<213> ORGANISM: Artificial Sequence
<220> FEATURE:
<223> OTHER INFORMATION: Full-length TAL Right Arm

<400> SEQUENCE: 62

Asn Leu Thr Pro Asp Gln Val Val Ala Ile Ala Ser His Asp Gly Gly
1               5                   10                  15

Lys Gln Ala Leu Glu Thr Val Gln Arg Leu Leu Pro Val Leu Cys Gln
            20                  25                  30

Asp His Gly Leu Thr Pro Glu Gln Val Val Ala Ile Ala Ser His Asp
        35                  40                  45

Gly Gly Lys Gln Ala Leu Glu Thr Val Gln Arg Leu Leu Pro Val Leu
    50                  55                  60

Cys Gln Ala His Gly Leu Thr Pro Asp Gln Val Val Ala Ile Ala Ser
65                  70                  75                  80
```

-continued

```
His Asp Gly Gly Lys Gln Ala Leu Glu Thr Val Gln Arg Leu Leu Pro
             85                  90                  95
Val Leu Cys Gln Ala His Gly Leu Thr Pro Ala Gln Val Val Ala Ile
            100                 105                 110
Ala Ser Asn Gly Gly Lys Gln Ala Leu Glu Thr Val Gln Arg Leu
        115                 120                 125
Leu Pro Val Leu Cys Gln Asp His Gly Leu Thr Pro Asp Gln Val Val
    130                 135                 140
Ala Ile Ala Asn Asn Asn Gly Gly Lys Gln Ala Leu Glu Thr Val Gln
145                 150                 155                 160
Arg Leu Leu Pro Val Leu Cys Gln Asp His Gly Leu Thr Pro Glu Gln
                165                 170                 175
Val Val Ala Ile Ala Ser Asn Ile Gly Gly Lys Gln Ala Leu Glu Thr
            180                 185                 190
Val Gln Arg Leu Leu Pro Val Leu Cys Gln Ala His Gly Leu Thr Pro
        195                 200                 205
Asp Gln Val Val Ala Ile Ala Ser His Asp Gly Gly Lys Gln Ala Leu
    210                 215                 220
Glu Thr Val Gln Arg Leu Leu Pro Val Leu Cys Gln Ala His Gly Leu
225                 230                 235                 240
Thr Pro Ala Gln Val Val Ala Ile Ala Ser His Asp Gly Gly Lys Gln
                245                 250                 255
Ala Leu Glu Thr Val Gln Arg Leu Leu Pro Val Leu Cys Gln Asp His
            260                 265                 270
Gly Leu Thr Pro Asp Gln Val Val Ala Ile Ala Ser Asn Ile Gly Gly
        275                 280                 285
Lys Gln Ala Leu Glu Thr Val Gln Arg Leu Leu Pro Val Leu Cys Gln
    290                 295                 300
Asp His Gly Leu Thr Pro Glu Gln Val Val Ala Ile Ala Ser Asn Gly
305                 310                 315                 320
Gly Gly Lys Gln Ala Leu Glu Thr Val Gln Arg Leu Leu Pro Val Leu
                325                 330                 335
Cys Gln Ala His Gly Leu Thr Pro Asp Gln Val Val Ala Ile Ala Ser
            340                 345                 350
His Asp Gly Gly Lys Gln Ala Leu Glu Thr Val Gln Arg Leu Leu Pro
        355                 360                 365
Val Leu Cys Gln Ala His Gly Leu Thr Pro Ala Gln Val Val Ala Ile
    370                 375                 380
Ala Ser His Asp Gly Gly Lys Gln Ala Leu Glu Thr Val Gln Arg Leu
385                 390                 395                 400
Leu Pro Val Leu Cys Gln Asp His Gly Leu Thr Pro Asp Gln Val Val
                405                 410                 415
Ala Ile Ala Ser His Asp Gly Gly Lys Gln Ala Leu Glu Thr Val Gln
            420                 425                 430
Arg Leu Leu Pro Val Leu Cys Gln Asp His Gly Leu Thr Pro Glu Gln
        435                 440                 445
Val Val Ala Ile Ala Asn Asn Asn Gly Gly Lys Gln Ala Leu Glu Thr
    450                 455                 460
Val Gln Arg Leu Leu Pro Val Leu Cys Gln Ala His Gly Leu Thr Pro
465                 470                 475                 480
Asp Gln Val Val Ala Ile Ala Ser Asn Ile Gly Gly Lys Gln Ala Leu
                485                 490                 495
Glu Thr Val Gln Arg Leu Leu Pro Val Leu Cys Gln Ala His Gly Leu
```

-continued

```
              500                 505                 510
Thr Pro Ala Gln Val Val Ala Ile Ala Asn Asn Asn Gly Gly Lys Gln
        515                 520                 525

Ala Leu Glu Thr Val Gln Arg Leu Leu Pro Val Leu Cys Gln Asp His
        530                 535                 540

Gly Leu Thr Pro Glu Gln Val Val Ala Ile Ala Ser Asn Ile Gly Gly
545                 550                 555                 560

Arg Pro Ala Leu Glu Ser
                565
```

CORRECTION OF CRB1 MUTATIONS

REFERENCE TO RELATED APPLICATIONS

This application claims priority from U.S. Provisional Patent Application Ser. Nos. 61/830,412, filed Jun. 3, 2013 and 61/875,230, filed Sep. 9, 2013, the entire content of both of which is incorporated herein by reference.

GRANT REFERENCE

This invention was made with government support under Grant No. U42 OD011185-02, awarded by the National Institutes of Health. The Government has certain rights in the invention.

FIELD OF THE INVENTION

The present invention relates generally to correction of the mouse Crumbs homolog 1 (Crb1) gene in mice having a mutation in this gene that renders the Crb1 protein non-functional.

BACKGROUND OF THE INVENTION

Crb1 is found to be normally expressed in many tissues, including lymph node, cortex, cerebellum, olfactory bulb and the retina, and also during development. Crb1 is thought to be involved in maintaining the integrity of the external limiting membrane and mutations in Crb1 result in genetic retinal disorders such as retinitis pigmentosa and Leber congenital amaurosis in humans, den Hollander et al. 2001, Am J Hum Genet 69:198-203.

The retinal degeneration 8 (rd8) mutation of the Crb1 gene (Crb1$^{rd8}$; Crb1<rd8>) is a frequently found in inbred mice, being present in ~20-25% of background. This mutation is a loss of a single nucleotide in exon 9 leading to a frame shift and early termination of protein translation that truncates the transmembrane and cytoplasmic domain of the Crb1 protein. The frame shift introduces a new stop codon (TGA) 144 bp downstream from the rd8 nucleotide deletion, Mehalo et al. 2003, Hum Mol Genet, 12(17):2179-89. Mutations in Crb1 in mice lead to visual abnormalities (Bulgakova & Knust 2009, 122, 2587-2596). The Crb1$^{rd8}$ mutation results in irregular retinal lesions in the inferior nasal quadrant of the fundus and the Crb1 complex is also implicated in the regulation of renal epithelia polarity, Pieczynski & Margolis, 2011 (Am. J. Physiol. Renal Physiol, 300(3): F589-F601), and tumorigenesis, Laprise, 2011 (J Biomed Biotechnol, 2011; 2011:868217. doi: 10.1155/2011/868217).

One of the inbred mouse strains that carry the Crb1$^{rd8}$ mutation is the mouse strain C57BL/6N, lacking a C nucleotide in the Crb1 gene. This has implications for all ocular vision research models on C57BL/6N background. With the C57BL/6N embryonic stem (ES) cell line as a major workhorse for genetic engineering to create new mouse models, the mutation in Crb1 impacts the downstream phenotypic analysis. The issue of the rd8 mutation of the Crb1 gene and impact on the phenotypic analysis has been recently discussed in Mattapallil et al. 2012, Invest Ophthalmol Vis Sci 53:2921-7; Luhmann et al. 2012, PLoS One 7:e35551.

Outcrossing of this mutation by congenic backcross approaches would be cumbersome, time-consuming and expensive, and as with all backcrossing it would never be guaranteed that such approach would be successful, as backcrossing is limited by recombination, and may never be complete, as it has been reported that certain DNA stretches persist.

Methods and compositions are provided by the present invention for correcting a mutation in the Crb1 gene of mice characterized by non-functional Crb1 protein. The present invention provides genetically modified animals and cells including edited chromosomal sequences encoding a corrected Crb1$^{rd8}$ mutation. In particular aspects of the present invention, the genetically modified animals or cells including edited chromosomal sequences encoding a corrected Crb1$^{rd8}$ mutation are generated using a Transcription Activator-Like Effector Nuclease (TALEN).

SUMMARY OF THE INVENTION

Genetically engineered mice having a corrected Crb1$^{rd8}$ mutation are provided according to aspects of the present invention.

Genetically engineered C57BL/6N strain mice having a corrected Crb1$^{rd8}$ mutation are provided according to aspects of the present invention.

Genetically engineered C57BL/6NJ; C57BL/6NJcl; C57BL/6NTac; C57BL/6NCr; C57BL/6NCrl; C57BL/6NHsd; and C57BL/6NCrlCrlj strain mice having a corrected Crb1$^{rd8}$ mutation are provided according to aspects of the present invention.

Genetically engineered C57BL/6N strain mice having a corrected Crb1$^{rd8}$ mutation are provided according to aspects of the present invention, wherein the C57BL/6N strain is characterized by at least 5 single-nucleotide polymorphisms (SNPs), where: 08-015199792-M (rs3709624) is C; 11-004367508-M (rs3659787) is A; 13-041017317-M (rs3722313) is C; 15-057561875-M (rs3702158) is G; 19-049914266-M (rs3724876) is T.

Genetically engineered 5558/B6(129S4)-Crb1<rd8>/ Boc; B6.129P2-Prkcq$^{tm1Litt}$/J; STOCK Crb1$^{rd8}$/J; and B6/129-Crb1$^{rd8}$/J strain mice having a corrected Crb1$^{rd8}$ mutation are provided according to aspects of the present invention.

Genetically engineered mice having a corrected Crb1$^{rd8}$ mutation are provided according to aspects of the present invention wherein the genetically engineered mouse has a repaired genomic DNA sequence encoding a portion of mouse Crb1 including the repaired Crb1<rd8> locus and comprising one or more introduced nucleotide differences compared to mouse Crb1 gene of a reference mouse of the same strain, wherein the one or more introduced nucleotide differences do not result in a difference in the amino acid sequence of Crb1 encoded by the repaired genomic DNA sequence compared to the reference mouse of the same strain.

Genetically engineered mice having a corrected Crb1$^{rd8}$ mutation are provided according to aspects of the present invention wherein the genetically engineered mouse has a repaired genomic DNA sequence encoding a portion of mouse Crb1 including the repaired Crb1<rd8> locus and comprising one or more introduced nucleotide differences compared to mouse Crb1 gene of a reference mouse of the same strain, wherein the one or more introduced nucleotide differences do not result in a difference in the amino acid sequence of Crb1 encoded by the repaired genomic DNA sequence compared to the reference mouse of the same strain, wherein the genetically engineered mice include a genomic DNA sequence selected from:
GACAGTTACAGCAGTTATCGGTGTGCCTGTCTGTC
(SEQ ID NO: 20) and/or the reverse complement thereof;

GACAGTTACAGCAGTTATAGGTGTGCCTGTCT
GTC (SEQ ID NO: 21) and/or the reverse complement
thereof;
GACAGCTACAGTTCTTATCGGTGTGCCTGTCTGTC
(SEQ ID NO: 22) and/or the reverse complement thereof;
GACAGCTACAGTTCTTATCGGTGTGCCT-
GTCTCTC (SEQ ID NO: 23) and/or the reverse complement thereof;
GACAGTTACAGCAGTTATCGGTGTGCCTGTCTCTC
(SEQ ID NO: 24) and/or the reverse complement thereof;
GACAGCTACAG
CAGTTATCGGTGTGCCTGTCTCTC (SEQ ID NO: 25)
and/or the reverse complement thereof;
GACAGCTACAGTTCTTATAGGTGTGCCTGTCTGTC
(SEQ ID NO: 26) and/or the reverse complement thereof;
GACAGCTACAGTTCTTATCGGTGTGCCT-
GTCTCTC (SEQ ID NO: 27) and/or the reverse complement thereof;
GACAGTTACAGTTCTTATCGGTGTGCCTGTCTGTC
(SEQ ID NO: 28) and/or the reverse complement thereof;
and GACAGTTACAGTAGTTATCGGTGTGCCTGTCT
GTC (SEQ ID NO: 29) and/or the reverse complement
thereof.

Kits for correction of a mouse Crb1<rd8>mutation are provided according to aspects of the present invention which include: an expression vector including one or more nucleic acids encoding at least two TALs and an appropriate nuclease, together encoding a TALEN specific for mouse Crb1 and functional to specifically introduce a double stranded break at a target sequence in the chromosome so as to allow for introduction of at least one donor oligonucleotide including a nucleotide sequence to correct the mouse Crb1<rd8>mutation in the genomic DNA of a fertilized oocyte, an embryo or a cell.

Non-limiting examples of appropriate nucleases encoded by a nucleic acid in an expression vector according to aspects of the present invention are Type us restriction endonucleases.

Non-limiting examples of appropriate nucleases encoded by a nucleic acid in an expression vector according to aspects of the present invention are FokI, HhaI, HindIII, NotI, BbvCI, EcoRI, Bg/I, and AlwI.

Non-limiting examples of appropriate nucleases encoded by a nucleic acid in an expression vector according to aspects of the present invention are FokI and genetically engineered cleavage monomers of FokI that form obligate heterodimers such as those mutated from E to K at position 490 and from I to K at 538, designated FokI "E490K:I538K" and those mutated from Q to E at position 486 and from I to L at position 499, designated FokI "Q486E:I499L.

Kits for correction of a mouse Crb1<rd8>mutation are provided according to aspects of the present invention which include: an expression vector comprising one or more nucleic acids encoding TAL Left Arm Sequence, TAL Right Arm Sequence and an appropriate nuclease, together encoding a TALEN specific for mouse Crb1 and functional to specifically introduce a double stranded break at a target sequence in the chromosome so as to allow for introduction of at least one donor oligonucleotide including a nucleotide sequence to correct the mouse Crb1<rd8>mutation in the genomic DNA of a fertilized oocyte, an embryo or a cell.

Optionally, TAL Left Arm has amino acid sequence SEQ ID NO:33 or a variant thereof and TAL Left Arm has amino acid sequence SEQ ID NO:62 or a variant thereof Optionally, the TALEN includes TAL Left Arm+FokI monomer of SEQ ID NO:59 or a variant thereof and the TALEN includes TAL Right Arm+FokI monomer of SEQ ID NO:60 or a variant thereof.

Kits for correction of a mouse Crb1<rd8>mutation are provided according to aspects of the present invention which include: at least one donor oligonucleotide, an expression vector comprising one or more nucleic acids encoding TAL Left Arm Sequence, TAL Right Arm Sequence and an appropriate nuclease, together encoding a TALEN specific for mouse Crb1 and functional to specifically introduce a double stranded break at a target sequence in the chromosome so as to allow for introduction of the at least one donor oligonucleotide including a nucleotide sequence to correct the mouse Crb1<rd8>mutation in the genomic DNA of a fertilized oocyte, an embryo or a cell.

Kits for correction of a mouse Crb1<rd8>mutation are provided according to aspects of the present invention which include: at least one donor oligonucleotide selected from the donor oligonucleotides of SEQ ID NOs: 1, 2, 3 and 4, an expression vector comprising one or more nucleic acids encoding TAL Left Arm Sequence, TAL Right Arm Sequence and an appropriate nuclease, together encoding a TALEN specific for mouse Crb1 and functional to specifically introduce a double stranded break at a target sequence in the chromosome so as to allow for introduction of the at least one donor oligonucleotide including a nucleotide sequence to correct the mouse Crb1<rd8>mutation in the genomic DNA of a fertilized oocyte, an embryo Or a cell.

Kits for correction of a mouse Crb1<rd8>mutation are provided according to aspects of the present invention which include: in combination, polyadenylated capped RNA encoding TAL Left Arm Sequence and TAL Right Arm Sequence and an appropriate nuclease; and donor oligonucleotide; as a ready-to-microinject solution for microinjection of fertilized oocytes, embryos and/or cells.

Kits for correction of a mouse Crb1<rd8>mutation are provided according to aspects of the present invention which include: in combination, polyadenylated capped RNA encoding TAL Left Arm Sequence and TAL Right Arm Sequence, an appropriate nuclease; a donor oligonucleotide and a compatible carrier; as a ready-to-microinject solution for microinjection of fertilized oocytes, embryos and/or cells.

Kits for correction of a mouse Crb1<rd8>mutation are provided according to aspects of the present invention which include: one or more PCR primers for screening to detect presence of a donor oligonucleotide in the genome of a fertilized oocyte, embryo and/or cell; and a ready-to-microinject solution for microinjection of fertilized oocytes, embryos and/or cells comprising, in combination, polyadenylated capped RNA encoding TAL Left Arm Sequence and TAL Right Arm Sequence, an appropriate nuclease, a donor oligonucleotide and a compatible carrier.

Methods for correction of a mouse Crb1<rd8>mutation are provided according to aspects of the present invention which include introducing an expression vector including a nucleic acid encoding TAL Left Arm Sequence and TAL Right Arm Sequence and an appropriate nuclease into a fertilized mouse oocyte, embryo and/or cell having a Crb1<rd8> mutation to produce a TALEN functional to specifically introduce a double stranded break at a target sequence in the chromosome so as to allow for introduction of at least one donor oligonucleotide including a nucleotide sequence to correct the mouse Crb1 rd8 mutation in the genomic DNA of a fertilized oocyte, an embryo or a cell; and introducing a donor nucleotide selected from SEQ ID NOs:

1-4 into a fertilized mouse oocyte, embryo and/or cell having a Crb1<rd8>mutation.

Methods for correction of a mouse Crb1<rd8>mutation are provided according to aspects of the present invention which include introducing an expression vector comprising a nucleic acid encoding at least two TALs and an appropriate nuclease into a fertilized mouse oocyte, embryo and/or cell having a Crb1<rd8>mutation to produce a TALEN functional to specifically introduce a double stranded break at a target sequence in the chromosome so as to allow for introduction of at least one donor oligonucleotide including a nucleotide sequence to correct the mouse Crb1<rd8>mutation in the genomic DNA of a fertilized oocyte, an embryo or a cell; and introducing a donor nucleotide selected from SEQ ID NOs: 1-4 into a fertilized mouse oocyte, embryo and/or cell having a Crb1<rd8>mutation.

Methods for correction of a mouse Crb1<rd8>mutation are provided according to aspects of the present invention which include introducing a mRNA encoding at least two TALs and an appropriate nuclease into a fertilized mouse oocyte, embryo and/or cell having a Crb1<rd8>mutation to produce a TALEN functional to specifically introduce a double stranded break at a target sequence in the Crb1 gene to allow for introduction of at least one donor oligonucleotide including a nucleotide sequence to correct the mouse Crb1<rd8>mutation in the genomic DNA of a fertilized oocyte, an embryo or a cell; and introducing a donor nucleotide selected from SEQ ID NO:1, SEQ ID NO:2, SEQ ID NO:3, SEQ ID NO:4, a variant of any thereof having at least 85%, at least 86%, at least 87%, at least 88%, at least 89%, at least 90%, at least 91%, at least 92%, at least 93%, at least 94% at least 95%, at least 96%, at least 97%, at least 98%, at least 99% identity, or greater identity, to any of SEQ ID NO:1, SEQ ID NO:2, SEQ ID NO:3, SEQ ID NO:4, wherein the variant encodes an amino acid sequence identical to the amino acid sequence encoded by SEQ ID NO:1, SEQ ID NO:2, SEQ ID NO:3 or SEQ ID NO:4, into a fertilized mouse oocyte, embryo and/or cell having a Crb1<rd8>mutation.

Expression vectors are provided according to aspects of the present invention which encode a fusion protein of a TAL and a nuclease monomer, the TAL selected from SEQ ID NO: 33 and 62, or a variant thereof.

Expression vectors are provided according to aspects of the present invention which encode a fusion protein of a TAL and a nuclease monomer, the fusion protein selected from SEQ ID NO: 59 and 60 or a variant thereof.

Expression vectors are provided according to aspects of the present invention which encode a fusion protein of a TAL and a nuclease monomer selected, the TAL selected from SEQ ID NO: 33 and 62, wherein the TAL of SEQ ID NOs: 33 and 62 is encoded by SEQ ID NOs:32 and 61, respectively, or a variant thereof.

Expression vectors are provided according to aspects of the present invention which encode a fusion protein of a TAL and a nuclease monomer selected, the fusion protein selected from SEQ ID NO: 59 and 60, wherein the fusion protein of SEQ ID NOs: 59 and 60 is encoded by SEQ ID NOs:54 and 58, respectively, or a variant thereof.

TALENs including at least two TALs and an appropriate nuclease are provided according to aspects of the present invention, the TALENs functional to specifically introduce a double stranded break at a target sequence in the chromosome so as to allow for introduction of at least one donor oligonucleotide including a nucleotide sequence to correct the mouse Crb1<rd8>mutation in the genomic DNA of a fertilized oocyte, an embryo or a cell.

TALENs including at least two TALs and an appropriate nuclease are provided according to aspects of the present invention, the TALENs including the TALs and FokI nuclease monomer fusion proteins of SEQ ID NOs: 33 and 62 and functional to specifically introduce a double stranded break at a target sequence in the chromosome so as to allow for introduction of at least one donor oligonucleotide including a nucleotide sequence to correct the mouse Crb1<rd8>mutation in the genomic DNA of a fertilized oocyte, an embryo or a cell.

TALENs including at least two TALs and an appropriate nuclease are provided according to aspects of the present invention, the TALENs including the TALs and FokI nuclease monomer fusion proteins of SEQ ID NOs: 59 and 60 and functional to specifically introduce a double stranded break at a target sequence in the chromosome so as to allow for introduction of at least one donor oligonucleotide including a nucleotide sequence to correct the mouse Crb1<rd8>mutation in the genomic DNA of a fertilized oocyte, an embryo or a cell.

BRIEF DESCRIPTION OF THE DRAWINGS

FIG. 1A is a schematic illustration of the Crb1rd8 allele which results from a single base deletion (arrow) causing a frame shift and functional null mutation (putative translation product in lighter lettering); aligned below the Crb1rd8 nucleotide sequence is the central core sequence of the ssODNs (shown 5' to 3') used to facilitate gene correction (200mer and 52mer sequences in Table 2), homology is indicated by periods, while base changes in the oligo are shown in text; the base repairing the point mutation is boxed;

FIG. 1B is a schematic illustration of the corrected CRB1 gene product predicted to be identical to the wild type CRB1 protein, along with the final repaired gene sequence (COR) which closely matches the wild type (WT) version of the Crb1 gene at the nucleotide level, except for the five synonymous base substitutions;

FIG. 2 shows a sequencing example with the insertion of C to correct the Crb1$^{rd8}$ mutation;

FIG. 5 is a table showing the number and percentages of animals born, showing evidence of TALEN-mediated events, as well as HDR events, and illegitimate recombination events for 200mer ssODNs across all conditions, varying ssODN concentration, and TALEN mRNA concentrations;

FIG. 6 is a table showing the number and percentages of animals born, showing evidence of TALEN-mediated events, as well as HDR events, and illegitimate recombination events for 52mer ssODNs across all conditions, varying ssODN concentration, and TALEN mRNA concentrations;

DETAILED DESCRIPTION OF THE INVENTION

Figure 3:
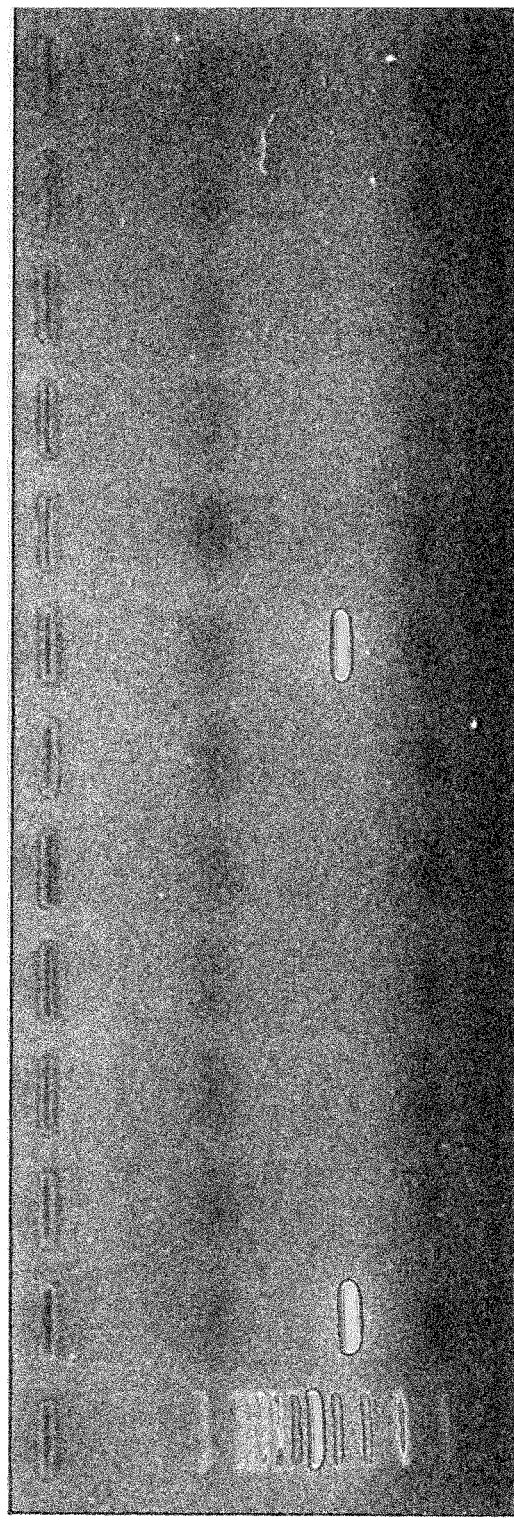
FIG. 3 is an image of a gel showing PCR products with primer pair specific for integration of the oligonucleotide into the Crb1$^{rd8}$ locus. Successful integration yields a 330 bp PCR product, while unsuccessful integration results in no PCR product. Mice #1144 and #1507 (lanes 2, 8)=positive for integration, all others failed to integrate. MWL=100 bp molecular weight ladder (Promega) showing 100 bp increments from 100-1000 bp (higher intensity band=500 bp) as well as 1500 bp (top)
Figure 3:
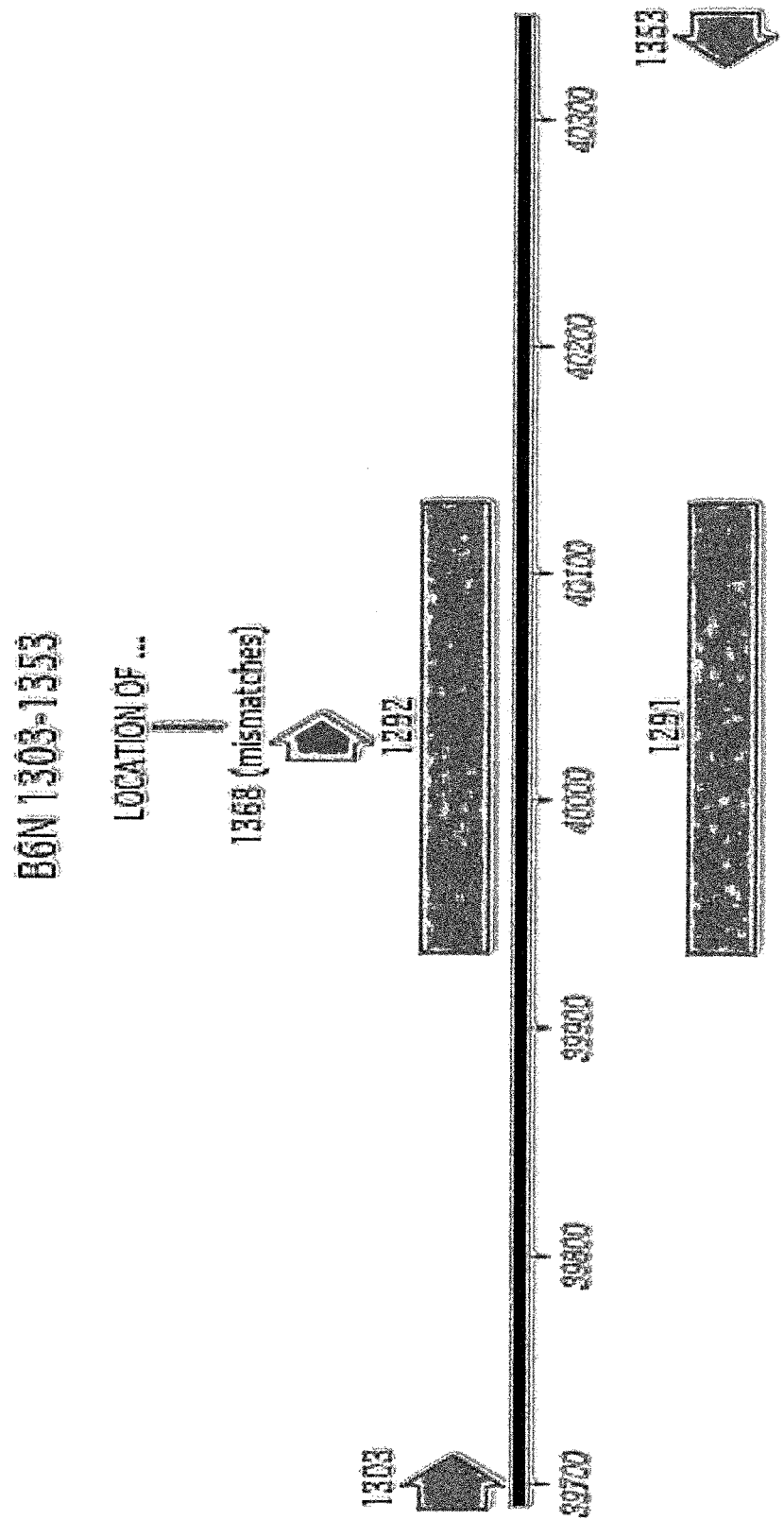

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Engelke, D. R., RNA Interference (RNAi): Nuts and Bolts of RNAi Technology, DNA Press LLC, Eagleville, Pa., 2003; Herdewijn, P. (Ed.), Oligonucleotide Synthesis: Methods and Applications, Methods in Molecular Biology, Humana Press, 2004; A. Nagy, M. Gertsenstein, K. Vintersten, R. Behringer, Manipulating the Mouse Embryo: A Laboratory Manual, 3rd edition, Cold Spring Harbor Laboratory Press; Dec. 15, 2002, ISBN-10: 0879695919; Kursad Turksen (Ed.), Embryonic stem cells: methods and protocols in Methods Mol Biol. 2002; 185, Humana Press; Current Protocols in Stem Cell Biology, ISBN: 9780470151808.

The singular terms "a," "an," and "the" are not intended to be limiting and include plural referents unless explicitly stated otherwise or the context clearly indicates otherwise.

The term "nucleic acid" as used herein refers to RNA or DNA molecules having more than one nucleotide in any form including single-stranded, double-stranded, oligonucleotide or polynucleotide. The term "nucleotide sequence" is used to refer to the ordering of nucleotides in an oligonucleotide or polynucleotide in a single-stranded form of nucleic acid.

The terms "duplex" and "double-stranded" are used to refer to nucleic acids characterized by binding interaction of complementary nucleotide sequences. A duplex includes a "sense" strand and an "antisense" strand. Such duplexes include RNA/RNA, DNA/DNA or RNA/DNA types of duplexes.

The terms "oligonucleotide" and "oligo" are used interchangeably, and are used herein to describe a nucleotide sequence having from 2-1000 linked nucleotides, while the term "polynucleotide" is used to describe a nucleotide sequence having more than 1000 nucleotides.

The term "nucleotide" is used herein as a noun to refer to individual nucleotides or varieties of nucleotides as opposed to a nucleotide sequence.

The term "genetically engineered mouse" refers to a mouse that contains heterologous DNA introduced into the individual mouse genome or mouse strain genome by means of molecular biological techniques, i.e., recombinant DNA technology.

The terms "inbred mouse" and "inbred mouse strain" refers to mice that are as genetically alike as possible, being homozygous at virtually all of their loci, except for the sex difference. An inbred strain is one that is produced using at least about 20 consecutive generations of sister x brother or parent x offspring matings or is traceable to a single ancestral pair in about the 20th or subsequent generation. An inbred strain has a unique set of characteristics that sets it apart from all other inbred strains.

In particular aspects, the invention relates to the use of genome editing approaches to correct defective mouse chromosomal sequences encoding non-functional Crb1 associated with retinal degeneration.

In particular aspects, the invention relates to the use of genome editing approaches to correct defective mouse chromosomal sequences encoding non-functional Crb1 associated with retinal degeneration in a C57BL/6N mouse strain.

In particular aspects, the invention relates to the use of genome editing approaches to correct defective mouse chromosomal sequences having the rd8 mutation and encoding non-functional Crb1 associated with retinal degeneration in a C57BL/6N mouse strain.

C57BL/6N Mouse Strain

C57BL/6N is a substrain of C57BL/6 (Mekada et al. 2009, Exp Anim 58(2):141-9). The C57BL/6N is characterized by at least 5 single-nucleotide polymorphisms (SNP): C57BL/6NJ type as follows: 08-015199792-M (rs3709624) is C; 11-004367508-M (rs3659787) is A; 13-041017317-M (rs3722313) is C; 15-057561875-M (rs3702158) is G; 19-049914266-M (rs3724876) is T. Useful SNPs are known in the art and described for example in Mekada et al, 2009; Petkov et al, 2004; and Zurita et al, 2011. The C57BL/6N strains do not have the exon 7-11 deletion in the gene nicotinamide nucleotide transhydrogenase (NM), which has been documented for C57BL/6J, Mekada et al, 2009; and Toye et al, 2005.

TABLE 1A

C57BL/6N strains with rd8 mutation in Crb1
Strain Name

C57BL/6NJ (The Jackson Laboratory stock no. 005304)
C57BL/6NJcl
C57BL/6NTac
C57BL/6NCr
C57BL/6NCrl
C57BL/6NCrlCrlj
C57BL/6NHsd

TABLE 1B

Additional mouse strains with rd8 mutation in Crb1
Strain Name

B6(129S4)-Crb1<rd8>/Boc (The Jackson Laboratory stock no. 5558)
B6.129P2-Prkcq$^{tm1Litt}$/J (The Jackson Laboratory stock: 005711)
STOCK Crb1$^{rd8}$/J (The Jackson Laboratory stock: 003392)
B6;129-Crb1$^{rd8}$/J (The Jackson Laboratory stock: 004852)
CXB12/HiAJ (The Jackson Laboratory stock: 001633)
CXB9/HiAJ (The Jackson Laboratory stock: 001630)
CXB2/ByJ (The Jackson Laboratory stock: 000352)
CXB3/ByJ (The Jackson Laboratory stock: 000353)
CXB5/ByJ (The Jackson Laboratory stock: 000355)
HPG/BmJ (The Jackson Laboratory stock: 000804)

The rd8 mutation of the Crb1 gene in mouse is defined by SNP rs219888696 [*Mus musculus*], for C57BL/6N with the sequence TGACCATCCCGAGAGACAGGCACAC-CATAAGAACTGTAGCTGTCTTCACAG (SEQ ID NO: 5). In the case of C57BL/6J, the corresponding sequence is TGACCATCCCGAGAGACAGGCACACCGA-TAAGAACTGTAGCTGTCTTCACAG (SEQ ID NO: 6).

TABLE 2

SNPs to distinguish C57BL/6NJ from C57BL/6J

| Reference SNP ID | Difference N vs. J | C57BL/6NJ | C57BL/6J |
|---|---|---|---|
| 08-015199792-M (rs3709624) | C/T | AACGAGAAGCcCAGAGTCACC (SEQ ID NO: 7) | AACGAGAAGCtCAGAGTCACC (SEQ ID NO: 13) |
| 11-004367508-M (rs3659787) | A/G | AACTTACTAAaCAAACCCACT (SEQ ID NO: 8) | AACTTACTAAgCAAACCCACT (SEQ ID NO: 14) |
| 13-041017317-M (rs3722313) | C/T | AGCTCCTTCCcAGCCTGATCT (SEQ ID NO: 9) | AGCTCCTTCCtAGCCTGATCT (SEQ ID NO: 15) |
| 15-057561875-M (rs3702158) | G/A | GGCCCAGTGTgAACAAAGGAA (SEQ ID NO: 10) | GGCCCAGTGTaAACAAAGGAA (SEQ ID NO: 16) |
| 19-049914266-M (rs3724876) | T/G | TCACCAGAGCtGCCCTGAGGC (SEQ ID NO: 11) | TCACCAGAGCgGCCCTGAGGC (SEQ ID NO: 17) |
| rs219888696 (Crb1) | -/G | TGACCATCCCGAGAGACAGGCA CACCATAAGAACTGTAGCTGTC TTCACAG (SEQ ID NO: 12) | TGACCATCCCGAGAGACAGGCA CACCGATAAGAACTGTAGCTGTC TTCACAG (SEQ ID NO: 6) |

Genetic Engineering Methods

Methods of the present invention to correct a mutation in the C57BL/6N gene, particularly the rd8 mutation of Crb1, also defined by the SNP rs219888696, are described according to the present invention. This type of gene repair is the first time this has been achieved in an inbred mouse strain.

A method provided by the present invention to correct a mutation in the C57BL/6N gene is to isolate embryonic stem (ES) cells or induced pluripotent stem (iPS) cells or a cell from the mouse strain and use a knock in strategy to correct the defect. For this method, homology recombination gene replacement strategies can be used, such as homing endonucleases, integrases, meganucleases, transposons, nuclease-mediated processes using a zinc finger nuclease (ZFN), a Transcription Activator-Like (TAL), a Clustered Regularly Interspaced Short Palindromic Repeats (CRISPR)-Cas, or a Drosophila Recombination-Associated Protein (DRAP) approach. Briefly, the process includes introducing into ES or iPS cells RNA molecules encoding a targeted TALEN or ZFN or CRISPR or DRAP and at least one oligonucleotide, then selecting for an ES or iPS cell with the corrected gene.

A further method of the present invention to correct a mutation in the C57BL/6N gene is to correct the gene directly in the fertilized oocyte (zygotes) or embryo. For this, homing endonucleases, integrases, meganucleases, transposons, nuclease-mediated processes, such as zinc finger nuclease, TALEN, CRISPR-Cas or DRAP can be applied. Preferred approaches are TALEN, ZFN, CRISPR-Cas or DRAP. Briefly, the method includes introducing into a fertilized oocyte or an embryo or a cell at least one nucleic acid molecule encoding a targeted TALEN, ZFN, CRISPR-Cas or DRAP and, at least one oligonucleotide. The method further includes incubating the fertilized oocyte, embryo or cell to allow expression of the TALEN, ZFN, CRISPR-Cas or DRAP, wherein a double-stranded break introduced into the targeted chromosomal sequence by the TALEN, ZFN, CRISPR-Cas or DRAP is repaired by a homology-directed DNA repair process. The nucleic acid encoding TALEN, ZFN, CRISPR-Cas or DRAP can be DNA, as an expression vector, or RNA. Instead of nucleic acid encoding TALEN, ZFN, CRISPR-Cas or DRAP, a TALEN, ZFN, CRISPR-Cas or DRAP protein may be delivered to the fertilized oocyte or an embryo or a cell. The DRAP technology has been described in U.S. Pat. Nos. 6,534,643, 6,858,716 and 6,830,910 and Watt et al, 2006.

According to aspects of the invention, an additional five nucleotides in the Crb1 gene are altered using Transcription Activator-Like Effector Nuclease (TALEN) methods, allowing the corrected Crb1 gene to be easily distinguished from the original mutation and the natural wild type of the gene.

As used herein, the term "target site" or "target sequence" refer to a nucleic acid sequence that defines a portion of a chromosomal sequence to be edited and to which a nuclease is engineered to recognize and bind, provided sufficient conditions for binding exist.

Nucleases

Recently, nucleases, including TALEN, ZFN, and horning endonucleases such as I-SceI, that are engineered to specifically bind to target sites have been successfully used for genome modification in a variety of different species.

TAL (Transcription Activator-Like) Effectors

The plant pathogenic bacteria of the genus Xanthomonas are known to cause many diseases in important crop plants. Pathogenicity of Xanthomonas depends on a conserved type III secretion (T3S) system which injects more than 25 different effector proteins into the plant cell. Among these injected proteins are transcription activator-like (TAL) effectors or TALE (transcription activator-like effector) which mimic plant transcriptional activators and manipulate the plant transcript, see Kay et al 2007, Science, 318:648-651. These proteins contain a DNA binding domain and a transcriptional activation domain. One of the most well characterized TAL-effectors is AvrBs3 from Xanthomonas campestris pv. vesicatoria, (see Bonas et al 1989, Mol Gen Genet 218: 127-136 and WO2010079430). TAL effectors contain a centralized domain of tandem repeats, each repeat containing approximately 34 amino acids, which are key to the DNA binding specificity of these proteins. In addition, they contain a nuclear localization sequence and an acidic transcriptional activation domain, for a review see Schornack et al 2006, J Plant Physiol 163(3): 256-272; Scholze and Boch 2011, Curr Opin Microbiol, 14:47-53. In addition, in the phytopathogenic bacteria Ralstonia solanacearum two genes, designated brg11 and hpx17 have been found that are homologous to the AvrBs3 family of Xanthomonas in the

*R. solanacearum* biovar 1 strain GMI 1000 and in the biovar 4 strain RS1000, see Heuer et al. 2007, Appl and Envir Micro 73(13): 4379-4384. These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

Specificity of these TAL effectors depends on the sequences found in the tandem repeats. The repeated sequence includes approximately 102 bp and the repeats are typically 91-100% homologous with each other (Bonas et al, 1989, Mal Gen. Genet 218: 127-136). Polymorphism of the repeats is usually located at positions 12 and 13 and there appears to be a one-to-one correspondence between the identity of the hypervariable diresidues at positions 12 and 13 with the identity of the contiguous nucleotides in the TAL-effector's target sequence, see Moscou and Bogdanove 2009, Science 326: 1501; and Boch et al 2009, Science 326:1509-1512. The two hypervariable residues are known as repeat variable diresidues (RVDs), whereby one RVD recognizes one nucleotide of DNA sequence and ensures that the DNA binding domain of each TAL-effector can target large recognition sites with high precision (15-30 nt). Experimentally, the code for DNA recognition of these TAL-effectors has been determined such that an HD sequence at positions 12 and 13 leads to a binding to cytosine (C), NG binds to T, NI to A, C, G or T, NN binds to A or G, and IG binds to T. These DNA binding repeats have been assembled into proteins with new combinations and numbers of repeats, to make artificial transcription factors that are able to interact with new sequences and activate the expression of a reporter gene in plant cells (Boch et al 2009, Science 326:1509-1512). These DNA binding domains have now been shown to have general applicability in the field of targeted genomic editing or targeted gene regulation in all cell types (Gaj et al, 2013). Moreover, engineered TAL effectors have been shown to function in association with exogenous functional protein effector domains such as a nuclease, not naturally found in natural *Xanthomonas* TAL-effect or proteins in mammalian cells. TAL nucleases (TALNs or TALENs) can be constructed by combining TALs with a nuclease, e.g. FokI nuclease domain at the N-terminus or C-terminus, Kim et al. 1996, PNAS 93:1156-1160; Christian et al 2010, Genetics 186:757-761; Li et al, 2011; and Miller et al, 2011. The functionality of TALENs to cause deletions by NHEJ has been shown in rat, mouse, zebrafish, *Xenopus*, medaka, rat and human cells, Ansai et al, 2013; Carlson et al, 2012; Hockemeyer et al, 2011; Lei et al, 2012; Moore et al, 2012; Stroud et al, 2013; Sung et al, 2013; Wefers et al, 2013.

For TALEN, methods of making such are further described in the US patents U.S. Pat. Nos. 8,420,782, 8,450,471, 8,450,107, 8,440,432, 8,440,431 and US patent applications US20130137161, US20130137174.

Other useful endonucleases may include, for example, HhaI, HindIII, NotI, BbvCI, EcoRI, Bg/I, and AlwI. The fact that some endonucleases (e.g., FokI) only function as dimers can be capitalized upon to enhance the target specificity of the TAL effector. For example, in some cases each FokI monomer can be fused to a TAL effector sequence that recognizes a different DNA target sequence, and only when the two recognition sites are in close proximity do the inactive monomers come together to create a functional enzyme. By requiring DNA binding to activate the nuclease, a highly site-specific restriction enzyme can be created.

In some embodiments, the TALEN may further include a nuclear localization signal or sequence (NLS). A NLS is an amino acid sequence that facilitates targeting the TALEN nuclease protein into the nucleus to introduce a double stranded break at the target sequence in the chromosome.

Nuclear localization signals are known in the art, see, for example, Makkerh et al. 1996, Curr Biol. 6:1025-1027. NLS include the sequence PKKKRKV (SEQ ID NO: 18) from SV40 Large T-antigen, Kalderon 1984, Cell 39: 499-509; RPAATKKAGQAKKK (SEQ ID NO: 19) from nucleoplasmin, Dingwall et al., 1988, J Cell Biol. 107, 841-9. Further examples are described in McLane and Corbett 2009, IUBMB Life 61, 697-70; Dopie et al. 2012, PNAS 109, E544-E552.

The cleavage domain may be obtained from any endonuclease or exonuclease. Non-limiting examples of endonucleases from which a cleavage domain may be derived include, but are not limited to, restriction endonucleases and homing endonucleases. See, for example, 2002-2003 Catalog, New England Biolabs, Beverly, Mass.; and Belfort et al. (1997) Nucleic Acids Res. 25:3379-3388. Additional enzymes that cleave DNA are known, e.g., SI Nuclease; mung bean nuclease; pancreatic DNase I; micrococcal nuclease; yeast HO endonuclease. See also Linn et al. (eds.) Nucleases, Cold Spring Harbor Laboratory Press, 1993. One or more of these enzymes, or functional fragments thereof, may be used as a source of cleavage domains.

Zinc Finger-Mediated Genome Editing

The use of zinc finger nucleases (ZFN) for gene editing, especially for creating deletions has been well established. For example see Carbery et al, 2010; Cui et al, 2011; Hauschild et al, 2011; Orlando et al, 2010; and Porteus & Carroll, 2005. ZFNs can be used to generate knockouts by introducing non-homologous end joining (NHEJ)-mediated deletions or for targeted insertion via a homology-directed repair process.

Components of the zinc finger nuclease-mediated process include a zinc finger nuclease with a DNA binding domain and a cleavage domain. Such are described for example in Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr Opin. Biotechnol. 12:632-637; and Chao et al. (2000) Curr Opin. Struct. Biol. 10:411-416; and U.S. Pat. Nos. 6,453,242 and 6,534,261. Methods to design and select a zinc finger binding domain to a target sequence are known in the art, see for example Biochemistry 2002, 41, 7074-7081; U.S. Pat. Nos. 6,607,882; 6,534,261 and 6,453,242. In some embodiments, the zinc finger nuclease may further include a nuclear localization signal or sequence (NLS). A NLS is an amino acid sequence that facilitates targeting the zinc finger nuclease protein into the nucleus to introduce a double stranded break at the target sequence in the chromosome. Nuclear localization signals are known in the art. See, for example, Makkerh et al. (1996) Current Biology 6:1025-1027. The cleavage domain may be obtained from any endonuclease or exonuclease. Non-limiting examples of endonucleases from which a cleavage domain may be derived include, but are not limited to, restriction endonucleases and homing endonucleases. See, for example, 2002-2003 Catalog, New England Biolabs, Beverly, Mass.; and Belfort et al. (1997) Nucleic Acids Res. 25:3379-3388. Additional enzymes that cleave DNA are known (e.g., SI Nuclease; mung bean nuclease; pancreatic DNase I; micrococcal nuclease; yeast HO endonuclease). See also Linn et al. (eds.) Nucleases, Cold Spring Harbor Laboratory Press, 1993. One or more of these enzymes (or functional fragments thereof) may be used as a source of cleavage domains. A cleavage domain also may be derived from an enzyme or portion thereof, as described above, that requires dimerization for cleavage activity. Two zinc finger nucleases may be required for cleavage, as each nuclease includes a monomer of the active enzyme dimer. Alternatively, a single zinc finger nuclease may include both monomers to create an active enzyme dimer. Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) PNAS 89:4275-4279; Li et al. (1993) PNAS 90:2764-2768; Kim et al. (1994) PNAS 91:883-887; Kim et al. (1994) J. Biol. Chem. 269:31, 978-31, 982. Thus, a zinc finger nuclease may include the cleavage domain from at least one Type IIS restriction enzyme and one or more zinc finger binding domains, which may or may not be engineered. Exemplary Type IIS restriction enzymes are described for example in International Publication WO 07/014,275, the disclosure of which is incorporated by reference herein in its entirety. Additional restriction enzymes also contain separable binding and cleavage domains, and these also are contemplated by the present disclosure. See, for example, Roberts et al. (2003) Nucleic Acids Res. 31: 418-420. An exemplary Type IIS restriction enzyme, whose cleavage domain is separable from the binding domain, is FokI. This particular enzyme is active as a dimer (Bitinaite et al. 1998, PNAS 95: 10,570-10,575). Accordingly, for the purposes of the present disclosure, the portion of the FokI enzyme used in a zinc finger nuclease is considered a cleavage monomer. Thus, for targeted double stranded cleavage using a FokI cleavage domain, two zinc finger nucleases, each including a FokI cleavage monomer, may be used to reconstitute an active enzyme dimer. Alternatively, a single polypeptide molecule containing a zinc finger binding domain and two FokI cleavage monomers may also be used. In certain embodiments, the cleavage domain may include one or more engineered cleavage monomers that minimize or prevent homodimerization, as described, for example, in U.S. Patent Publication Nos. 20050064474, 20060188987, and 20080131962, each of which is incorporated by reference herein in its entirety. By way of non-limiting example, amino acid residues at positions 446, 447, 479, 483, 484, 486, 487, 490, 491, 496, 498, 499, 500, 531, 534, 537 and 538 of FokI are all targets for influencing dimerization of the FokI cleavage half-domains. Exemplary engineered cleavage monomers of FokI that form obligate heterodimers include a pair in which a first cleavage monomer includes mutations at amino acid residue positions 490 and 538 of FokI and a second cleavage monomer that includes mutations at amino-acid residue positions 486 and 499. Thus, in one embodiment, a mutation at amino acid position 490 replaces Glu (E) with Lys (K); a mutation at amino acid residue 538 replaces Ile (I) with Lys (K); a mutation at amino acid residue 486 replaces Gln (Q) with Glu (E); and a mutation at position 499 replaces Ile (I) with Lys (K). Specifically, the engineered cleavage monomers may be prepared by mutating positions 490 from E to K and 538 from I to K in one cleavage monomer to produce an engineered cleavage monomer designated "E490K:I538K" and by mutating positions 486 from Q to E and 499 from I to L in another cleavage monomer to produce an engineered cleavage monomer designated "Q486E:I499L." The above described engineered cleavage monomers are obligate heterodimer mutants in which aberrant cleavage is minimized or abolished. Engineered cleavage monomers may be prepared using a suitable method, for example, by site-directed mutagenesis of wild-type cleavage monomers (FokI) as described in U.S. Patent Publication No. 20050064474.

The zinc finger nuclease described above may be engineered to introduce a double stranded break at the targeted site of integration. The double stranded break may be at the targeted site of integration, or it may be up to 1, 2, 3, 4, 5, 10, 15, 20, 25, 30, 35, 40, 45, 50, 100 or 1000 nucleotides away from the site of integration. In some embodiments, the double stranded break may be up to 1, 2, 3, 4, 5, 10, 15, or 20 nucleotides away from the site of integration. In other embodiments, the double stranded break may be up to 10, 15, 20, 25, 30, 35, 40, 45 or 50 nucleotides away from the site of integration. In yet other embodiments, the double stranded break may be up to 50, 100 or 1000 nucleotides away from the site of integration.

CRISPR-Cas System

CRISPRs (Clustered Regularly Interspaced Short Palindromic Repeats) are loci containing multiple short direct repeats that are found in the genomes of approximately 40% of sequenced bacteria and 90% of sequenced archaea and confer resistance to foreign DNA elements, see Horvath, 2010, Science 327: 167-170; Barrangou et al, 2007; and Makarova et al, 2011. CRISPR repeats range in size from 24 to 48 base pairs. They usually show some dyad symmetry, implying the formation of a secondary structure such as a hairpin, but are not truly palindromic. CRISPR repeats are separated by spacers of similar length.

The CRISPR-associated (cas) genes are often associated with CRISPR repeat-spacer arrays. More than forty different Cas protein families have been described (Haft et al. 2005, PLoS Comput Biol. 1 (6): e60). Particular combinations of cas genes and repeat structures have been used to define 8 CRISPR subtypes, some of which are associated with an additional gene module encoding repeat-associated mysterious proteins (RAMPs).

There are diverse CRISPR systems in different organisms, and one of the simplest is the type II CRISPR system from *Streptococcus pyogenes*: only a single gene encoding the Cas9 protein and two RNAs, a mature CRISPR RNA (crRNA) and a partially complementary trans-acting RNA (tracrRNA), are necessary and sufficient for RNA-guided silencing of foreign DNAs (Gasiunas et al, 2012; Jinek et al, 2012). Maturation of crRNA requires tracrRNA and RNase III (Deltcheva et al, 2011). However, this requirement can be bypassed by using an engineered small guide RNA (sgRNA) containing a designed hairpin that mimics the tracrRNA-crRNA complex (Jinek et al., 2012). Base pairing between the sgRNA and target DNA causes double-strand breaks (DSBs) due to the endonuclease activity of Cas9. Binding specificity is determined by both sgRNA-DNA base pairing and a short DNA motif (protospacer adjacent motif [PAM] sequence: NGG) juxtaposed to the DNA complementary region (Marraffini & Sontheimer, 2010). For example, the CRISPR system requires a minimal set of two molecules, the Cas9 protein and the sgRNA, and therefore can be used as a host-independent gene-targeting platform. Recently, it has been demonstrated that the Cas9/CRISPR can be harnessed for site-selective RNA-guided genome editing (Carroll, 2012; Chang et al, 2013; Cho et al, 2013; Cong et al, 2013; Hwang et al, 2013; Jiang et al, 2013; Mali et al, 2013; Qi et al, 2013; Shen et al, 2013; Wang et al, 2013). Wang et al.

2013 have shown that a targeted insertion is possible with the CRISPR/Cas9system when combining it with oligonucleotides.

Expression Vectors

A nucleic acid encoding one or more nucleases and/or one or more other peptides or proteins, such as TALs, can be cloned into an expression vector for transformation into prokaryotic or eukaryotic cells and expression of the encoded peptides and/or protein(s). As used herein, "expression vectors" are defined as polynucleotides which, when introduced into an appropriate host cell, e.g. an expression system, can be transcribed and translated into a polypeptide(s). An in vivo "expression system" is a suitable host cell containing an expression vector that can function to yield a desired expression product. Expression vectors may also be used to produce the encoded proteins in vitro, such as in in vitro expression systems.

Expression vectors can be prokaryotic vectors, e.g., plasmids, or shuttle vectors, insect vectors, or eukaryotic vectors.

Nuclease expression constructs can be readily designed using methods known in the art. See, e.g., US Patent Publications 20030232410; 20050208489; 20050026157; 20050064474; 20060188987; 20060063231; 20080182332; 2009011188 and International Publication WO 07/014,275. Expression of the nuclease may be under the control of a constitutive promoter or an inducible promoter. Additional suitable bacterial and eukaryotic promoters are well known in the art and described, e.g., in Sambrook et al., Molecular Cloning, A Laboratory Manual (2nd ed. 1989; 3rd ed., 2001); Kriegler, Gene Transfer and Expression: A Laboratory Manual (1990); and Ausubel et al., Current Protocols in Molecular Biology. Bacterial expression systems for expressing the protein are available in, e.g., *E. coli, Bacillus* sp., and *Salmonella*, Palva et al. (1983) Gene 22:229-235.

In addition to the promoter, the expression vector typically contains a transcription unit or expression cassette that contains all the additional elements required for the expression of the nucleic acid in host cells, either prokaryotic or eukaryotic, for example signal sequences, enhancer elements, and transcription termination sequences. A typical expression cassette thus contains a promoter operably linked, e.g., to a nucleic acid sequence encoding the nuclease, and signals required, e.g., for efficient polyadenylation of the transcript, transcriptional termination, ribosome binding sites, or translation termination. Additional elements of the cassette may include, e.g., enhancers, heterologous splicing signals, and/or a nuclear localization signal (NLS).

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, cytomegalovirus immediate early promoter; herpes simplex virus thymidine kinase promoter; early and late SV40 promoters; phosphoglycerate kinase (PGK) promoter; promoter present in long terminal repeats from a retrovirus; mouse metallothionein-I promoter; and various art-known tissue specific promoters.

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL 10 promoter, an ADH2 promoter, a PH05 promoter, a CUP1 promoter, a GAL7 promoter, a MET25 promoter, a MET3 promoter, a CYC1 promoter, a HIS 3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1, e.g., for use in *Pichia*. Selection of the appropriate vector and promoter is well within the level of ordinary skill in the art.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter, see e.g., U.S. Patent Publication No. 20040131637; a pagC promoter, see Pulkkinen and Miller, J. Bacteriol, 1991: 173(1): 86-93; Alpuche-Aranda et al., PNAS, 1992; 89(21): 10079-83; a nirB promoter, see Harborne et al. (1992) Mol. Micro. 6:2805-2813; and the like, see, e.g., Dunstan et al. (1999) Infect. Immun. 67:5133-5141; McKelvie et al. (2004) Vaccine 22:3243-3255; and Chatfield et al. (1992) Biotechnol. 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2; see, e.g., WO96/17951); an actA promoter, see, e.g., Shetron-Rama et al. (2002) Infect. Immun. 70: 1087-1096; an rps M promoter; see, e.g., Valdivia and Falkow (1996). Mol. Microbiol. 22:367); a Tet (Tetracycline) promoter, see, e.g., Hillen, W. and Wissmann, A. (1989) in Saenger, W. and Heinemann, U. (eds), Topics in Molecular and Structural Biology, Protein-Nucleic Acid Interaction. Macmillan, London, UK, Vol. 10, pp. 143-162; an SP6 promoter, see, e.g., Melton et al. (1984) Nucl. Acids Res. 12:7035; and the like. Suitable strong promoters for use in prokaryotes such as *Escherichia coli* include, but are not limited to Trc, Tac, T5, T7, and pLambda. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator, see for example deBoer et al. (1983) PNAS 80:21-25.

Kits for such expression systems are commercially available. Eukaryotic expression systems for mammalian cells, are well known by those of skill in the art and are also commercially available.

Any of the well-known procedures for introducing foreign nucleotide sequences into host cells may be used. These include the use of calcium phosphate transfection, polybrene, protoplast fusion, electroporation, ultrasonic methods (e.g., sonoporation), liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

For example, Cas9 and dCas9 genes are cloned from the vectors pMJ806 and pMJ841 as described in Jinek et al., 2012. The genes are PCR amplified and inserted into a vector containing a Tc-inducible promoter PLtetO-1, (Lutz and Bujard, 1997, Nucleic Acids Res. 25:1203-10), a chloramphenicol-selectable marker, and a p15A replication origin. The sgRNA template is cloned into a vector containing a minimal synthetic promoter (J23119) with an annotated transcription start site, an ampicillin-selectable marker, and a ColE1 replication origin. Inverse PCR is used to generate sgRNA cassettes with new 20 bp complementary regions. Expression systems are described for example in Cong et al, 2013; and Jinek et al, 2012.

Donor oligonucleotides are used in combination with gene editing systems including TAL, ZFN, CRISPR, and DRAP according to aspects of the present invention.

The method for editing chromosomal sequences at the Crb1 locus includes introducing at least one donor oligonucleotide including a sequence to correct the Crb1 mutation into a fertilized oocyte, an embryo or cell. A donor oligonucleotide includes at least three components: the sequence coding the sequence to correct the Crb1 mutation, an upstream sequence, and a downstream sequence. The sequence encoding the protein is flanked by the upstream and downstream sequence, wherein the upstream and downstream sequences share sequence similarity with either side of the site of integration in the chromosome.

Typically, the donor oligonucleotide will be DNA. The donor oligonucleotide may be a DNA plasmid, a linear piece of DNA, a PCR fragment, a naked nucleic acid, a single strand nucleic acid, a synthetic oligonucleotide or a nucleic acid complexed with a delivery vehicle such as a liposome or poloxamer. In a preferred embodiment, the donor oligonucleotide is single stranded.

Particular oligonucleotides useful to repair the Crb1$^{rd8}$ locus are provided by the present invention as described herein.

According to aspects of the present invention, the donor oligonucleotide includes any of the sequences in Table 3.

TABLE 3

| Donor oligonucleotides | | |
|---|---|---|
| | Single stranded donor oligonucleotide sequence (5' to 3') | SEQ ID No. |
| SEQ ID No. 1 | TTCTACAAATATGGTACTTACTGGCTGTTTGC CATCAAATGCCTGCCACTCCAGCCCCTGTTTG CATGGAGGAAACTGTGAAGACAGTTACAGCAG TTATCGGTGTGCCTGTCTGTCGGGATGGTCAG GGACACACTGTGAAATCAACATTGATGAGTGC TTTTCTAGCCCCTGTATCCATGGCAACTGCTC TGATGGAG | 200 mer Sense |
| SEQ ID No. 2 | CTCCATCAGAGCAGTTGCCATGGATACAGGGG CTAGAAAAGCACTCATCAATGTTGATTTCACA GTGTGTCCCTGACCATCCCGACAGACAGGCAC ACCGATAACTGCTGTAACTGTCTTCACAGTTT CCTCCATGCAAACAGGGGCTGGAGTGGCAGGC ATTTGATGGCAAACAGCCAGTAAGTACCATAT TTGTAGAA | 200 mer Antisense |
| SEQ ID No. 3 | TGAAGACAGTTACAGCAGTTATCGGTGTGCCT GTCTGTCGGGATGGTCAGGG | 52 mer Sense |
| SEQ ID No. 4 | CCCTGACCATCCCGACAGACAGGCACACCGAT AACTGCTGTAACTGTCTTCA | 52 mer Antisense |

In one embodiment of the present invention, the upstream and downstream sequences in the donor oligonucleotide may share about 80%, 85%, 90%, 95%, 96%, 97%, 98%, 99% or 100% sequence identity with the targeted chromosomal sequence. In an exemplary embodiment, the upstream and downstream sequences in the donor oligonucleotide may share about 98%, 99% or 100% sequence identity with the targeted chromosomal sequence.

An upstream or downstream sequence may include from about 15 bp to about 1000 bp. In one embodiment, an upstream or downstream sequence may include about 15, 20, 30, 40, 45, 50, 55, 60, 70, 80, 90, 100, 125, 150, 170, 200, 300, 400, 500, 600, 700, 800, 900 or 1000 bp.

For the design of the donor oligonucleotide according to the present invention, additional specific mutations are introduced into the binding site (e.g. TAL binding site) that after integration the DNA strand will not be efficiently recognized by the gene editing tools, and hence not cleaved by the nuclease. Thus, in a region of 1-100 nucleotides on each side flanking the mutation to be corrected, at least one nucleotide differs from the genomic sequence such that the sequence is different but the amino acid code is not affected so that the encoded protein is identical to the wild-type protein. Further, the at least one nucleotide which differs from the genomic sequence is chosen such that the translation rate is not significantly affected, i.e. it is similar to the original code.

The donor oligonucleotide as described herein was synthesized using well-known standard recombinant techniques, see, for example, Sambrook et al., 2001 and Ausubel et al., 1996, or synthesis methods, see for example Herdewijn 2010, Oligonucleotide Synthesis: Methods and Applications, Humana Press.

In the method detailed above for integrating donor oligonucleotide into the Crb1 locus, a double stranded break introduced into the chromosomal sequence by a endonuclease is repaired, via homologous recombination with the donor oligonucleotide, such that the donor oligonucleotide is integrated into the chromosome. The presence of a double-stranded break facilitates integration of the sequence into the chromosome. A donor oligonucleotide may be physically integrated or, alternatively, the donor oligonucleotide may be used as a template for repair of the break, resulting in the introduction of the chromosomal sequence as well as all or part of the upstream and downstream sequences of the donor oligonucleotide into the chromosome. Thus, endogenous chromosomal sequence may be converted to the sequence of the donor oligonucleotide.

Delivery of Nucleic Acids

To mediate genomic editing, at least one nucleic acid molecule encoding a nuclease or DRAP, and at least one donor oligonucleotide is delivered to a fertilized oocyte, embryo or the cell of interest. Typically, the embryo is a preimplantation stage embryo. A mouse preimplantation stage embryo is either a fertilized oocyte, a 2-cell stage embryo, a 4-cell stage embryo, a 8-cell stage embryo, a 16-cell stage embryo, a morula or a blastocyst. A mouse preimplantation stage embryo is an embryo after fertilization until implantation. For mouse this stage is up to 4 days after fertilization.

As used herein the terms "fertilized oocyte" and "zygote" are used interchangeably, and means the stage of a single cell embryo.

Suitable methods of introducing the nucleic acids to a fertilized oocyte, an embryo or cell include microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, and delivery via liposomes, immunoliposomes, virosomes, or artificial virions. In one embodiment, the nucleic acids may be introduced into an embryo by microinjection.

The nucleic acids may be microinjected into the nucleus or the cytoplasm of the fertilized oocyte or embryo. In another embodiment the nucleic acids may be introduced into a cell by nucleofection. In another embodiment DRAP protein is introduced together with at least one oligonucleotide.

In embodiments of the present invention in which both a nucleic acid encoding a nuclease and a donor oligonucleotide are introduced into a fertilized oocyte or an embryo or cell, the ratio of donor (or exchange) oligonucleotide to nucleic acid encoding a nuclease may range from about 1:10 to about 10:1. In various embodiments, the ratio of donor oligonucleotide to nucleic acid encoding a nuclease may be about 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1. In one embodiment, the ratio of donor oligonucleotide to nucleic acid encoding a nuclease may be about 5:1.

In embodiments of the present invention in which more than one nucleic acid encoding a nuclease and, and more than one donor oligonucleotide are introduced into a fertilized oocyte, an embryo or cell, the nucleic acids may be introduced simultaneously or sequentially. For example, nucleic acids encoding a nuclease, each specific for a distinct recognition sequence, as well as the optional donor oligonucleotides, may be introduced at the same time. Alternatively, each nucleic acid encoding a nuclease, as well as the donor oligonucleotides, may be introduced sequentially.

Culturing the Fertilized Oocyte, Embryo or Cell

The method of inducing genomic editing with a nuclease further includes culturing the fertilized oocyte, embryo or cell including the introduced nucleic acid(s) to allow expression of the nuclease. A fertilized oocyte or embryo may be cultured in vitro or in vivo. For in vitro culture, the fertilized oocyte or embryo is cultured at an appropriate temperature and in appropriate media with the necessary $CO_2$ ratio to allow the expression of the nuclease. Suitable non-limiting examples of media include M2, M16, KSOM, BMOC, and RTF media. A skilled artisan will appreciate that culture conditions can and will vary depending on the strain of fertilized oocyte or embryo. Routine optimization may be used, in all cases, to determine the best culture conditions for a particular strain of fertilized oocyte or embryo. In some cases, a cell line may be derived from an in vitro-cultured embryo (e.g., an embryonic stem cell line or induced pluripotent stem (iPS) or spermatogonial stem cell line). The in vitro cultured fertilized oocyte or embryo can be transferred into a female host for development to term, i.e. to obtain live offspring.

Alternatively, a fertilized oocyte or embryo may be cultured in vivo by transferring the embryo into the uterus of a female host. Generally speaking, the female host is from the same or similar species as the embryo. Preferably, the female host is pseudo-pregnant. Methods of preparing pseudo-pregnant female hosts are known in the art. Additionally, methods of transferring an embryo into a female host are known. Culturing an embryo in vivo permits the embryo to develop and may result in a live birth of an animal derived from the embryo. Such an animal would include the edited chromosomal sequence in Crb1 in every cell of the body.

Similarly, cells including the introduced nucleic acids may be cultured using standard procedures to allow expression of a nuclease. Standard cell culture techniques are described, for example, in Santiago et al. (2008) PNAS 105:5809-5814; Moehle et al. (2007) PNAS 104:3055-3060; Urnov et al. (2005) Nature 435:646-651; and Lombardo et al (2007) Nat. Biotechnol 25: 1298-1306. Those of skill in the art appreciate that methods for culturing cells are known in the art and can and will vary depending on the cell type. Routine optimization may be used, in all cases, to determine the best techniques for a particular cell type.

Upon expression of the nuclease, the chromosomal sequence may be edited. In cases in which the embryo or cell includes an expressed nuclease and a donor oligonucleotide, the nuclease recognizes, binds, and cleaves the target sequence in the chromosomal sequence of interest. The double-stranded break introduced by the nuclease is repaired, via homologous recombination with the donor oligonucleotide, such that the sequence in the donor oligonucleotide is integrated into the chromosomal sequence.

Genetically Modified Animals

Several new mouse strains expressing the corrected Crb1 protein are provided by the present invention.

One aspect of the present invention provides a genetically modified animal in which at least one nucleotide sequence in exon 9 of the Crb1 gene has been edited, i.e. one nucleotide has been inserted, i.e. the addition of a C, or A or reverse complement. In a preferred embodiment, the addition of a C. In addition to the insertion of one C or one A to correct the rd8 mutation in Crb1, the genetically modified mouse may have 1, 2, 3, 4, or 5 nucleotides in exon 9 of the Crb1 gene which differ compared to the wild-type.

The genetically engineered mouse carries one of the sequences or reverse complement thereof, listed below:

```
                                           (SEQ ID NO: 20)
GACAGTTACAGCAGTTATCGGTGTGCCTGTCTGTC
or
                                           (SEQ ID NO: 21)
GACAGTTACAGCAGTTATAGGTGTGCCTGTCTGTC
or
                                           (SEQ ID NO: 22)
GACAGCTACAGTTCTTATCGGTGTGCCTGTCTGTC
or
                                           (SEQ ID NO: 23)
GACAGCTACAGTTCTTATCGGTGTGCCTGTCTCTC
or
                                           (SEQ ID NO: 24)
GACAGTTACAGCAGTTATCGGTGTGCCTGTCTCTC
or
                                           (SEQ ID NO: 25)
GACAGCTACAGCAGTTATCGGTGTGCCTGTCTCTC
or
                                           (SEQ ID NO: 26)
GACAGCTACAGTTCTTATAGGTGTGCCTGTCTGTC
or
                                           (SEQ ID NO: 27)
GACAGCTACAGTTCTTATCGGTGTGCCTGTCTCTC
or
                                           (SEQ ID NO: 28)
GACAGTTACAGTTCTTATCGGTGTGCCTGTCTGTC
or
                                           (SEQ ID NO: 29)
GACAGTTACAGTAGTTATCGGTGTGCCTGTCTGTC.
```

The correction of the rd8 mutation in Crb1 according to aspects of methods of the present invention occurs in 2-cell, 4-cell, 8-cell or 16-cell stage embryos. Thus, the founder mice resulting from introduction of at least one donor oligonucleotide including a nucleotide sequence to correct the mouse Crb1<rd8>mutation in the genomic DNA of a fertilized oocyte, an embryo or a cell will have the corrected Crb1 gene in many, but not all, cells. Breeding of founder mice having the corrected Crb1 gene in germ cells is performed to provide offspring having the corrected Crb1 gene in all cells.

Thus, a genetically engineered mouse comprising a corrected Crb1$^{rd8}$ mutation in all cells is provided by the present invention.

According to aspects, a genetically engineered C57BL/6N mouse comprising a corrected Crb1$^{rd8}$ mutation in all cells is provided by the present invention.

According to aspects, a genetically engineered C57BL/6NJ; C57BL/6NJcl; C57BL/6NTac; C57BL/6NCr; C57BL/6NCrl; or C57BL/6NHsd C57BL/6NCrlCrlj mouse comprising a corrected Crb1$^{rd8}$ mutation in all cells is provided by the present invention.

According to aspects, a genetically engineered C57BL/6N mouse comprising a corrected Crb1$^{rd8}$ mutation in all cells is provided by the present invention, wherein the C57BL/6N strain is characterized by at least 5 single-nucleotide polymorphisms (SNPs), where: 08-015199792-M (rs3709624) is C; 11-004367508-M (rs3659787) is A; 13-041017317-M (rs3722313) is C; 15-057561875-M (rs3702158) is G; 19-049914266-M (rs3724876) is T.

According to aspects, a genetically engineered C57BL/6N mouse comprising a corrected Crb1$^{rd8}$ mutation in all cells is provided by the present invention, wherein the mouse strain is selected from the group consisting of: 5558/B6 (129S4)-Crb1<rd8>/Boc; B6.129P2-Prkcq$^{tm1Litt}$/J; STOCK Crb1$^{rd8}$/J; B6/129-Crb1$^{rd8}$/J; CXB12/HiAJ; CXB9/HiAJ; CXB2/ByJ; CXB3/ByJ; CXB5/ByJ; and HPG/BmJ.

According to aspects, a genetically engineered C57BL/6N mouse comprising a corrected Crb1$^{rd8}$ mutation in all cells is provided by the present invention, wherein the inbred mouse includes a genomic DNA sequence selected from:
GACAGTTACAGCAGTTATCGGTGTGCCTGTCTGTC (SEQ ID NO: 20) and/or the reverse complement thereof;
GACAGTTACAGCAGTTATAGGTGTGCCTGTCTGTC (SEQ ID NO: 21) and/or the reverse complement thereof;
GACAGCTACAGTTCTTATCGGTGTGCCTGTCTGTC (SEQ ID NO: 22) and/or the reverse complement thereof;
GACAGCTACAGTTCTTATCGGTGTGCCTGTCTCTC (SEQ ID NO: 23) and/or the reverse complement thereof;
GACAGTTACAGCAGTTATCGGTGTGCCTGTCTCTC (SEQ ID NO: 24) and/or the reverse complement thereof;
GACAGCTACAGCAGTTATCGGTGTGCCTGTCTCTC (SEQ ID NO: 25) and/or the reverse complement thereof;
GACAGCTACAGTTCTTATAGGTGTGCCTGTCTGTC (SEQ ID NO: 26) and/or the reverse complement thereof;
GACAGCTACAGTTCTTATCGGTGTGCCTGTCTCTC (SEQ ID NO: 27) and/or the reverse complement thereof;
GACAGTTACAGTTCTTATCGGTGTGCCTGTCTGTC (SEQ ID NO: 28) and/or the reverse complement thereof;
and GACAGTTACAGTAGTTATCGGTGTGCCTGTCTGTC (SEQ ID NO: 29) and/or the reverse complement thereof.

According to aspects, a genetically engineered C57BL/6N mouse comprising a corrected Crb1$^{rd8}$ mutation in all cells is provided by the present invention, wherein the inbred mouse comprises a repaired genomic DNA sequence encoding a portion of mouse Crb1 comprising the Crb1<rd8> locus and comprising one or more nucleotide differences compared to mouse Crb1 gene of a reference inbred mouse of the same strain, wherein the one or more nucleotide differences do not result in a difference in the amino acid sequence of Crb1 encoded by the repaired genomic DNA sequence.

The genetically modified animals disclosed herein may be crossbred to create animals including more than one edited chromosomal sequence or to create animals that are homozygous for one or more edited chromosomal sequences. For example, two animals including the same edited chromosomal sequence may be crossbred to create an animal homozygous for the edited chromosomal sequence In other embodiments, an animal including an edited chromosomal sequence in Crb1 disclosed herein may be crossbred to combine the edited chromosomal sequence with in Crb1 other genetic backgrounds. By way of non-limiting example, other genetic backgrounds may include wild-type genetic backgrounds, genetic backgrounds with deletion mutations, genetic backgrounds with another targeted integration, and genetic backgrounds with non-targeted integrations.

A genetically modified animal or cell as described above can be generated using a TALEN- or ZFN-mediated genome editing process. The process for editing a chromosomal sequence includes: (a) introducing into an embryo or cell at least one nucleic acid encoding a TALEN- or ZEN that recognizes a target sequence in the chromosomal sequence and is able to cleave a site in the chromosomal sequence, and at least one donor oligonucleotide including a sequence for integration flanked by an upstream sequence and a downstream sequence that share substantial sequence identity with either side of the cleavage site, and the at least one oligonucleotide may include a sequence that is substantially identical to a portion of the chromosomal sequence at the cleavage site and which further includes at least one nucleotide change; and (b) culturing the fertilized oocyte, embryo or cell to allow expression of the TALEN or ZFN such that the TALEN or ZFN introduces a double-stranded break into the chromosomal sequence, and wherein the double-stranded break is repaired by a homology-directed repair process such that the sequence in the donor oligonucleotide is integrated into the chromosomal sequence.

Kits for Correcting the Mouse Crb1<Rd8> Mutation

Mouse Crb1<rd8>mutation repair kits according to aspects of the present invention include a TALEN specific for mouse Crb1 including two TALs linked to a nuclease, the combination constituting a TALEN specific for mouse Crb1 and functional to specifically introduce a double stranded break at a target sequence in the chromosome so as to allow for introduction of at least one donor oligonucleotide including a nucleotide sequence to correct the mouse Crb1<rd8>mutation in the genomic DNA of a fertilized oocyte, an embryo or a cell.

TALs included according to aspects of the present invention are those encoded by the nucleic acid sequences shown and described herein as TAL Left Arm Sequence and TAL Right Arm Sequence.

Nucleic acids encoding the TALs are optionally provided in isolation in kits of the present invention for cloning into an expression vector encoding an appropriate nuclease, to achieve expression of a TALEN specific for mouse Crb1 and functional to specifically introduce a double stranded break at a target sequence in the chromosome so as to allow for introduction of at least one donor oligonucleotide including a nucleotide sequence to correct the mouse Crb1<rd8>mutation in the genomic DNA of a fertilized oocyte, an embryo or a cell.

Alternatively, nucleic acids encoding the TALs are provided in an expression vector also containing a nucleic acid sequence encoding an appropriate nuclease, to achieve expression of a TALEN specific for mouse Crb1 and functional to specifically introduce a double stranded break at a target sequence in the chromosome so as to allow for introduction of at least one donor oligonucleotide including a nucleotide sequence to correct the mouse Crb1<rd8>mutation in the genomic DNA of a fertilized oocyte, an embryo or a cell.

According to aspects, polyadenylated capped RNA encoding the TALs encoded by the nucleic acid sequences shown and described herein as TAL Left Arm Sequence and TAL Right Arm Sequence and an appropriate nuclease, to achieve expression of a TALEN specific for mouse Crb1 and functional to specifically introduce a double stranded break at a target sequence in the chromosome so as to allow for introduction of at least one donor oligonucleotide including a nucleotide sequence to correct the mouse Crb1 rd8 mutation in the genomic DNA of a fertilized oocyte, an embryo or a cell, are included in kits of the present invention.

Mouse Crb1<rd8>mutation repair kits according to aspects of the present invention further include at least one donor oligonucleotide including a nucleotide sequence to correct the mouse Crb1<rd8>mutation in the genomic DNA of a fertilized oocyte, an embryo or a cell.

Mouse Crb1<rd8>mutation repair kits according to aspects of the present invention optionally include at least one donor oligonucleotide including a nucleotide sequence to correct the mouse Crb1<rd8>mutation in the genomic DNA of a fertilized oocyte, an embryo or a cell selected from those shown in Table 3, SEQ ID NOs: 1-4.

The polyadenylated capped RNA encoding TAL Left Arm Sequence and TAL Right Arm Sequence and an appropriate nuclease; and donor oligonucleotide are optionally included in kits of the present invention as a ready-to-microinject solution for microinjection of fertilized oocytes, embryos and/or cells. A ready-to-microinject solution includes a compatible carrier, exemplified by, but not limited to, 10 mM Tris 7.5, 1 mM EDTA. The ready-to-microinject solution may be provided as a frozen composition, preferably kept frozen at −20° C. or lower, such as −80° C.

Crb1<rd8>mutation repair kits according to aspects of the present invention include a ready-to-microinject solution consisting of:
i) polyadenylated capped RNA encoding the two TALEN at 25 ng/microliter (range 0.5-100 ng/microliter), see TAL Left Arm Sequence and TAL Left Arm Sequence cloned into a nuclease expression vector, e.g. FokI
ii) donor oligonucleotide DNA as a 200mer (either antisense or sense strand) at 1 ng/microliter (range 0.1 to 10 ng/microliter) or 52mer (either antisense or sense strand) at 1 ng/microliter (range 0.1 to 10 ng/microliter), see Table 3 (SEQ ID NOs: 1-4)
iii) dissolved in TE (10 mM Tris 7.5, 1 mM EDTA)
iv) frozen at −20° C. or lower.

Optionally, a Crb1<rd8>mutation repair kit according to aspects of the present invention also contains PCR primers allowing the rapid screening of the resulting offspring or cells.

Transcription Activator-Like Effectors (TALs)

Particular TALs used for targeting the Crb1$^{rd8}$ locus are provided by the present invention, as described herein.

TAL Sequences for Crb1:

Sequence encoding TAL Left Arm, T7 RNA binding site, start codon and nuclear localization signal:

(SEQ ID NO: 30)
ATGCATCTAGAGAAGACAAGAACCTGACCCCAGACCAGGTAGTCGCAAT

CGCGAACAATAATGGGGGAAAGCAAGCCCTGGAAACCGTGCAAAGGTTG

TTGCCGGTCCTTTGTCAAGACCACGGCCTTACACCGGAGCAAGTCGTGG

CCATTGCAAGCAACATCGGTGGCAAACAGGCTCTTGAGACGGTTCAGAG

ACTTCTCCCAGTTCTCTGTCAAGCCCACGGGCTGACTCCCGATCAAGTT

GTAGCGATTGCGTCGAACATTGGAGGGAAACAAGCATTGGAGACTGTCC

AACGGCTCCTTCCCGTGTTGTGTCAAGCCCACGGTTTGACGCCTGCACA

AGTGGTCGCCATCGCCAACAACAACGGCGGTAAGCAGGCGCTGGAAACA

GTACAGCGCCTGCTGCCTGTACTGTGCCAGGATCATGGACTGACCCCAG

ACCAGGTAGTCGCAATCGCGTCGAACATTGGGGGAAAGCAAGCCCTGGA

AACCGTGCAAAGGTTGTTGCCGGTCCTTTGTCAAGACCACGGCCTTACA

CCGGAGCAAGTCGTGGCCATTGCATCCCACGACGGTGGCAAACAGGCTC

TTGAGACGGTTCAGAGACTTCTCCCAGTTCTCTGTCAAGCCCACGGGCT

GACTCCCGATCAAGTTGTAGCGATTGCGTCGAACATTGGAGGGAAACAA

GCATTGGAGACTGTCCAACGGCTCCTTCCCGTGTTGTGTCAAGCCCACG

GTTTGACGCCTGCACAAGTGGTCGCCATCGCCAACAACAACGGCGGTAA

GCAGGCGCTGGAAACAGTACAGCGCCTGCTGCCTGTACTGTGCCAGGAT

CATGGACTGACCCCAGACCAGGTAGTCGCAATCGCGTCACATGACGGGG

GAAAGCAAGCCCTGGAAACCGTGCAAAGGTTGTTGCCGGTCCTTTGTCA

AGACCACGGCCTTACACCGGAGCAAGTCGTGGCCATTGCAAGCAATGGG

GGTGGCAAACAGGCTCTTGAGACGGTTCAGAGACTTCTCCCAGTTCTCT

GTCAAGCCCACGGGCTGACTCCCGATCAAGTTGTAGCGATTGCGTCGAA

CATTGGAGGGAAACAAGCATTGGAGACTGTCCAACGGCTCCTTCCCGTG

TTGTGTCAAGCCCACGGTTTGACGCCTGCACAAGTGGTCGCCATCGCCA

GCCATGATGGCGGTAAGCAGGCGCTGGAAACAGTACAGCGCCTGCTGCC

TGTACTGTGCCAGGATCATGGACTGACCCCAGACCAGGTAGTCGCAATC

GCGTCGAACATTGGGGGAAAGCAAGCCCTGGAAACCGTGCAAAGGTTGT

TGCCGGTCCTTTGTCAAGACCACGGCCTTACACCGGAGCAAGTCGTGGC

CATTGCAAATAATAACGGTGGCAAACAGGCTCTTGAGACGGTTCAGAGA

CTTCTCCCAGTTCTCTGTCAAGCCCACGGGCTGACTCCCGATCAAGTTG

TAGCGATTGCGTCCAACGGTGGAGGGAAACAAGCATTGGAGACTGTCCA

ACGGCTCCTTCCCGTGTTGTGTCAAGCCCACGGTTTGACGCCTGCACAA

GTGGTCGCCATCGCCTCGAATGGCGGCGGTAAGCAGGCGCTGGAAACAG

TACAGCGCCTGCTGCCTGTACTGTGCCAGGATCATGGACTGAAGAGACC

GGATCCCGGGCCCGTCGACTGCAGAGG.

Sequence encoding TAL Right Arm, T7 RNA binding site, start codon and nuclear localization signal:

(SEQ ID NO: 31)
ATGCATCTAGAGAAGACAAGAACCTGACCCCAGACCAGGTAGTCGCAAT

CGCGTCACATGACGGGGGAAAGCAAGCCCTGGAAACCGTGCAAAGGTTG

-continued

TTGCCGGTCCTTTGTCAAGACCACGGCCTTACACCGGAGCAAGTCGTGG

CCATTGCATCCCACGACGGTGGCAAACAGGCTCTTGAGACGGTTCAGAG

ACTTCTCCCAGTTCTCTGTCAAGCCCACGGGCTGACTCCCGATCAAGTT

GTAGCGATTGCGTCGCATGACGGAGGGAAACAAGCATTGGAGACTGTCC

AACGGCTCCTTCCCGTGTTGTGTCAAGCCCACGGTTTGACGCCTGCACA

AGTGGTCGCCATCGCCTCGAATGGCGGCGGTAAGCAGGCGCTGGAAACA

GTACAGCGCCTGCTGCCTGTACTGTGCCAGGATCATGGACTGACCCCAG

ACCAGGTAGTCGCAATCGCGAACAATAATGGGGGAAAGCAAGCCCTGGA

AACCGTGCAAAGGTTGTTGCCGGTCCTTTGTCAAGACCACGGCCTTACA

CCGGAGCAAGTCGTGGCCATTGCAAGCAACATCGGTGGCAAACAGGCTC

TTGAGACGGTTCAGAGACTTCTCCCAGTTCTCTGTCAAGCCCACGGGCT

GACTCCCGATCAAGTTGTAGCGATTGCGTCGCATGACGGAGGGAAACAA

GCATTGGAGACTGTCCAACGGCTCCTTCCCGTGTTGTGTCAAGCCCACG

GTTTGACGCCTGCACAAGTGGTCGCCATCGCCAGCCATGATGGCGGTAA

GCAGGCGCTGGAAACAGTACAGCGCCTGCTGCCTGTACTGTGCCAGGAT

CATGGACTGACCCCAGACCAGGTAGTCGCAATCGCGTCGAACATTGGGG

GAAAGCAAGCCCTGGAAACCGTGCAAAGGTTGTTGCCGGTCCTTTGTCA

AGACCACGGCCTTACACCGGAGCAAGTCGTGGCCATTGCAAGCAATGGG

GGTGGCAAACAGGCTCTTGAGACGGTTCAGAGACTTCTCCCAGTTCTCT

GTCAAGCCCACGGGCTGACTCCCGATCAAGTTGTAGCGATTGCGTCGCA

TGACGGAGGGAAACAAGCATTGGAGACTGTCCAACGGCTCCTTCCCGTG

TTGTGTCAAGCCCACGGTTTGACGCCTGCACAAGTGGTCGCCATCGCCA

GCCATGATGGCGGTAAGCAGGCGCTGGAAACAGTACAGCGCCTGCTGCC

TGTACTGTGCCAGGATCATGGACTGACCCCAGACCAGGTAGTCGCAATC

GCGTCACATGACGGGGAAAGCAAGCCCTGGAAACCGTGCAAAGGTTGT

TGCCGGTCCTTTGTCAAGACCACGGCCTTACACCGGAGCAAGTCGTGGC

CATTGCAAATAATAACGGTGGCAAACAGGCTCTTGAGACGGTTCAGAGA

CTTCTCCCAGTTCTCTGTCAAGCCCACGGGCTGACTCCCGATCAAGTTG

TAGCGATTGCGTCGAACATTGGAGGGAAACAAGCATTGGAGACTGTCCA

ACGGCTCCTTCCCGTGTTGTGTCAAGCCCACGGTTTGACGCCTGCACAA

GTGGTCGCCATCGCCAACAACAACGGCGGTAAGCAGGCGCTGGAAACAG

TACAGCGCCTGCTGCCTGTACTGTGCCAGGATCATGGACTGAAGAGACC

GGATCCCGGGCCCGTCGACTGCAGAGG.

Sequence encoding full-length TAL Left Arm (SEQ ID NO:32):

AACCTGACCCCAGACCAGGTAGTCGCAATCGCGAACAATAATGGGGGAA

AGCAAGCCCTGGAAACCGTGCAAAGGTTGTTGCCGGTCCTTTGTCAAGA

CCACGGCCTTACACCGGAGCAAGTCGTGGCCATTGCAAGCAACATCGGT

GGCAAACAGGCTCTTGAGACGGTTCAGAGACTTCTCCCAGTTCTCTGTC

AAGCCCACGGGCTGACTCCCGATCAAGTTGTAGCGATTGCGTCGAACAT

TGGAGGGAAACAAGCATTGGAGACTGTCCAACGGCTCCTTCCCGTGTTG

TGTCAAGCCCACGGTTTGACGCCTGCACAAGTGGTCGCCATCGCCAACA

ACAACGGCGGTAAGCAGGCGCTGGAAACAGTACAGCGCCTGCTGCCTGT

ACTGTGCCAGGATCATGGACTGACCCCAGACCAGGTAGTCGCAATCGCG

TCGAACATTGGGGAAAGCAAGCCCTGGAAACCGTGCAAAGGTTGTTGC

CGGTCCTTTGTCAAGACCACGGCCTTACACCGGAGCAAGTCGTGGCCAT

TGCATCCCACGACGGTGGCAAACAGGCTCTTGAGACGGTTCAGAGACTT

CTCCCAGTTCTCTGTCAAGCCCACGGGCTGACTCCCGATCAAGTTGTAG

CGATTGCGTCGAACATTGGAGGGAAACAAGCATTGGAGACTGTCCAACG

GCTCCTTCCCGTGTTGTGTCAAGCCCACGGTTTGACGCCTGCACAAGTG

GTCGCCATCGCCAACAACAACGGCGGTAAGCAGGCGCTGGAAACAGTAC

AGCGCCTGCTGCCTGTACTGTGCCAGGATCATGGACTGACCCCAGACCA

GGTAGTCGCAATCGCGTCACATGACGGGGAAAGCAAGCCCTGGAAACC

GTGCAAAGGTTGTTGCCGGTCCTTTGTCAAGACCACGGCCTTACACCGG

AGCAAGTCGTGGCCATTGCAAGCAATGGGGGTGGCAAACAGGCTCTTGA

GACGGTTCAGAGACTTCTCCCAGTTCTCTGTCAAGCCCACGGGCTGACT

CCCGATCAAGTTGTAGCGATTGCGTCGAACATTGGAGGGAAACAAGCAT

TGGAGACTGTCCAACGGCTCCTTCCCGTGTTGTGTCAAGCCCACGGTTT

GACGCCTGCACAAGTGGTCGCCATCGCCAGCCATGATGGCGGTAAGCAG

GCGCTGGAAACAGTACAGCGCCTGCTGCCTGTACTGTGCCAGGATCATG

GACTGACCCCAGACCAGGTAGTCGCAATCGCGTCGAACATTGGGGAAA

GCAAGCCCTGGAAACCGTGCAAAGGTTGTTGCCGGTCCTTTGTCAAGAC

CACGGCCTTACACCGGAGCAAGTCGTGGCCATTGCAAATAATAACGGTG

GCAAACAGGCTCTTGAGACGGTTCAGAGACTTCTCCCAGTTCTCTGTCA

AGCCCACGGGCTGACTCCCGATCAAGTTGTAGCGATTGCGTCCAACGGT

GGAGGGAAACAAGCATTGGAGACTGTCCAACGGCTCCTTCCCGTGTTGT

GTCAAGCCCACGGTTTGACGCCTGCACAAGTGGTCGCCATCGCCTCGAA

TGGCGGCGGTAAGCAGGCGCTGGAAACAGTACAGCGCCTGCTGCCTGTA

CTGTGCCAGGATCATGGACTGACACCCGAACAGGTGGTCGCCATTGCTT

CCCACGACGGAGGACGGCCAGCCTTGGAGTCC

Full-length TAL Left Arm (SEQ ID NO:33):

NLTPDQVVAIAN NN GGKQALETVQRLLPVLCQDHGLTPEQVVAIAS NI G

GKQALETVQRLLPVLCQAHGLTPDQVVAIAS NI GGKQALETVQRLLPVL

CQAHGLTPAQVVAIAN NN GGKQALETVQRLLPVLCQDHGLTPDQVVAIA

S NI GGKQALETVQRLLPVLCQDHGLTPEQVVAIAS HD GGKQALETVQRL

LPVLCQAHGLTPDQVVAIAS NI GGKQALETVQRLLPVLCQAHGLTPAQV

VAIAN NN GGKQALETVQRLLPVLCQDHGLTPDQVVAIAS HD GGKQALET

VQRLLPVLCQDHGLTPEQVVAIAS NG GGKQALETVQRLLPVLCQAHGLT

PDQVVAIAS NI GGKQALETVQRLLPVLCQAHGLTPAQVVAIAS HD GGKQ

-continued

ALETVQRLLPVLCQDHGLTPDQVVAIAS[NI]GGKQALETVQRLLPVLCQD

HGLTPEQVVAIAN[NN]GGKQALETVQRLLPVLCQAHGLTPDQVVAIAS[NG]

GGKQALETVQRLLPVLCQAHGLTPAQVVAIAS[NG]GGKQALETVQRLLPV

LCQDHGLTPEQVVAIAS[HD]GGRPALES

Sequence encoding full-length TAL Right Arm (SEQ ID NO:61):

AACCTGACCCCAGACCAGGTAGTCGCAATCGCGAACAATAATGGGGGAA

AGCAAGCCCTGGAAACCGTGCAAAGGTTGTTGCCGGTCCTTTGTCAAGA

CCACGGCCTTACACCGGAGCAAGTCGTGGCCATTGCAAGCAACATCGGT

GGCAAACAGGCTCTTGAGACGGTTCAGAGACTTCTCCCAGTTCTCTGTC

AAGCCCACGGGCTGACTCCCGATCAAGTTGTAGCGATTGCGTCGAACAT

TGGAGGGAAACAAGCATTGGAGACTGTCCAACGGCTCCTTCCCGTGTTG

TGTCAAGCCCACGGTTTGACGCCTGCACAAGTGGTCGCCATCGCCAACA

ACAACGGCGGTAAGCAGGCGCTGGAAACAGTACAGCGCCTGCTGCCTGT

ACTGTGCCAGGATCATGGACTGACCCCAGACCAGGTAGTCGCAATCGCG

TCGAACATTGGGGGAAAGCAAGCCCTGGAAACCGTGCAAAGGTTGTTGC

CGGTCCTTTGTCAAGACCACGGCCTTACACCGGAGCAAGTCGTGGCCAT

TGCATCCCACGACGGTGGCAAACAGGCTCTTGAGACGGTTCAGAGACTT

CTCCCAGTTCTCTGTCAAGCCCACGGGCTGACTCCCGATCAAGTTGTAG

CGATTGCGTCGAACATTGGAGGGAAACAAGCATTGGAGACTGTCCAACG

GCTCCTTCCCGTGTTGTGTCAAGCCCACGGTTTGACGCCTGCACAAGTG

GTCGCCATCGCCAACAACAACGGCGGTAAGCAGGCGCTGGAAACAGTAC

AGCGCCTGCTGCCTGTACTGTGCCAGGATCATGGACTGACCCCAGACCA

GGTAGTCGCAATCGCGTCACATGACGGGGAAAGCAAGCCCTGGAAACC

GTGCAAAGGTTGTTGCCGGTCCTTTGTCAAGACCACGGCCTTACACCGG

AGCAAGTCGTGGCCATTGCAAGCAATGGGGGTGGCAAACAGGCTCTTGA

GACGGTTCAGAGACTTCTCCCAGTTCTCTGTCAAGCCCACGGGCTGACT

CCCGATCAAGTTGTAGCGATTGCGTCGAACATTGGAGGGAAACAAGCTT

GGAGACTGTCCAACGGCTCCTTCCCGTGTTGTGTCAAGCCCACGGTTTG

ACGCCTGCACAAGTGGTCGCCATCGCCAGCCATGATGGCGGTAAGCAGG

CGCTGGAAACAGTACAGCGCCTGCTGCCTGTACTGTGCCAGGATCATGG

ACTGACCCCAGACCAGGTAGTCGCAATCGCGTCGAACATTGGGGAAAG

CAAGCCCTGGAAACCGTGCAAAGGTTGTTGCCGGTCCTTTGTCAAGACC

ACGGCCTTACACCGGAGCAAGTCGTGGCCATTGCAAATAATAACGGTGG

CAAACAGGCTCTTGAGACGGTTCAGAGACTTCTCCCAGTTCTCTGTCAA

GCCCACGGGCTGACTCCCGATCAAGTTGTAGCGATTGCGTCCAACGGTG

GAGGGAAACAAGCATTGGAGACTGTCCAACGGCTCCTTCCCGTGTTGTG

TCAAGCCCACGGTTTGACGCCTGCACAAGTGGTCGCCATCGCCTCGAAT

GGCGGCGGTAAGCAGGCGCTGGAAACAGTACAGCGCCTGCTGCCTGTAC

TGTGCCAGGATCATGGACTGACACCCGAACAGGTGGTCGCCATTGCTTC

CCACGACGGAGGACGGCCAGCCTTGGAGTCC

Full-length TAL Right Arm (SEQ ID NO:62):

NLTPDQVVAIAS[HD]GGKQALETVQRLLPVLCQDHGLTPEQVVAIAS[HD]G

GKQALETVQRLLPVLCQAHGLTPDQVVAIAS[HD]GGKQALETVQRLLPVL

CQAHGLTPAQVVAIAS[NG]GGKQALETVQRLLPVLCQDHGLTPDQVVAIA

N[NN]GGKQALETVQRLLPVLCQDHGLTPEQVVAIAS[NI]GGKQALETVQRL

LPVLCQAHGLTPDQVVAIAS[HD]GGKQALETVQRLLPVLCQAHGLTPAQV

VAIAS[HD]GGKQALETVQRLLPVLCQDHGLTPDQVVAIAS[NI]GGKQALET

VQRLLPVLCQDHGLTPEQVVAIAS[NG]GGKQALETVQRLLPVLCQAHGLT

PDQVVAIAS[HD]GGKQALETVQRLLPVLCQAHGLTPAQVVAIAS[HD]GGKQ

ALETVQRLLPVLCQDHGLTPDQVVAIAS[HD]GGKQALETVQRLLPVLCQD

HGLTPEQVVAIAN[NN]GGKQALETVQRLLPVLCQAHGLTPDQVVAIAS[NI]

GGKQALETVQRLLPVLCQAHGLTPAQVVAIAN[NN]GGKQALETVQRLLPV

LCQDHGLTPEQVVAIAS[NI]GGRPALES

Sequence encoding TAL Left Arm+FokI monomer (SEQ ID NO: 54)

ATGGACTACAAAGACCATGACGGTGATTATAAAGATCATGACATCGATT

ACAAGGATGACGATGACAAGATGGCCCCCAAGAAGAAGAGGAAGGTGGG

CATTCACCGCGGGGTACCTATGGTGGACTTGAGGACACTCGGTTATTCG

CAACAGCAACAGGAGAAAATCAAGCCTAAGGTCAGGAGCACCGTCGCGC

AACACCACGAGGCGCTTGTGGGGCATGGCTTCACTCATGCGCATATTGT

CGCGCTTTCACAGCACCCTGCGGCGCTTGGGACGGTGGCTGTCAAATAC

CAAGATATGATTGCGGCCCTGCCCGAAGCCACGCACGAGGCAATTGTAG

GGGTCGGTAAACAGTGGTCGGGAGCGCGAGCACTTGAGGCGCTGCTGAC

TGTGGCGGGTGAGCTTAGGGGGCCTCCGCTCCAGCTCGACACCGGGCAG

CTGCTGAAGATCGCGAAGAGAGGGGGAGTAACAGCGGTAGAGGCAGTGC

ACGCCTGGCGCAATGCGCTCACCGGGGCCCCCTTGAACCTGACCCCAGA

CCAGGTAGTCGCAATCGCGAACAATAATGGGGGAAAGCAAGCCCTGGAA

ACCGTGCAAAGGTTGTTGCCGGTCCTTTGTCAAGACCACGGCCTTACAC

CGGAGCAAGTCGTGGCCATTGCAAGCAACATCGGTGGCAAACAGGCTCT

TGAGACGGTTCAGAGACTTCTCCCAGTTCTCTGTCAAGCCCACGGGCTG

ACTCCCGATCAAGTTGTAGCGATTGCGTCGAACATTGGAGGGAAACAAG

CATTGGAGACTGTCCAACGGCTCCTTCCCGTGTTGTGTCAAGCCCACGG

TTTGACGCCTGCACAAGTGGTCGCCATCGCCAACAACAACGGCGGTAAG

CAGGCGCTGGAAACAGTACAGCGCCTGCTGCCTGTACTGTGCCAGGATC

ATGGACTGACCCCAGACCAGGTAGTCGCAATCGCGTCGAACATTGGGG

AAAGCAAGCCCTGGAAACCGTGCAAAGGTTGTTGCCGGTCCTTTGTCAA

```
-continued
GACCACGGCCTTACACCGGAGCAAGTCGTGGCCATTGCATCCCACGACG
GTGGCAAACAGGCTCTTGAGACGGTTCAGAGACTTCTCCCAGTTCTCTG
TCAAGCCCACGGGCTGACTCCCGATCAAGTTGTAGCGATTGCGTCGAAC
ATTGGAGGGAAACAAGCATTGGAGACTGTCCAACGGCTCCTTCCCGTGT
TGTGTCAAGCCCACGGTTTGACGCCTGCACAAGTGGTCGCCATCGCCAA
CAACAACGGCGGTAAGCAGGCGCTGGAAACAGTACAGCGCCTGCTGCCT
GTACTGTGCCAGGATCATGGACTGACCCCAGACCAGGTAGTCGCAATCG
CGTCACATGACGGGGAAAGCAAGCCCTGGAAACCGTGCAAAGGTTGTT
GCCGGTCCTTTGTCAAGACCACGGCCTTACACCGGAGCAAGTCGTGGCC
ATTGCAAGCAATGGGGTGGCAAACAGGCTCTTGAGACGGTTCAGAGAC
TTCTCCCAGTTCTCTGTCAAGCCCACGGGCTGACTCCCGATCAAGTTGT
AGCGATTGCGTCGAACATTGGAGGGAAACAAGCATTGGAGACTGTCCAA
CGGCTCCTTCCCGTGTTGTGTCAAGCCCACGGTTTGACGCCTGCACAAG
TGGTCGCCATCGCCAGCCATGATGGCGGTAAGCAGGCGCTGGAAACAGT
ACAGCGCCTGCTGCCTGTACTGTGCCAGGATCATGGACTGACCCCAGAC
CAGGTAGTCGCAATCGCGTCGAACATTGGGGAAAGCAAGCCCTGGAAA
CCGTGCAAAGGTTGTTGCCGGTCCTTTGTCAAGACCACGGCCTTACACC
GGAGCAAGTCGTGGCCATTGCAAATAATAACGGTGGCAAACAGGCTCTT
GAGACGGTTCAGAGACTTCTCCCAGTTCTCTGTCAAGCCCACGGGCTGA
CTCCCGATCAAGTTGTAGCGATTGCGTCCAACGGTGGAGGGAAACAAGC
ATTGGAGACTGTCCAACGGCTCCTTCCCGTGTTGTGTCAAGCCCACGGT
TTGACGCCTGCACAAGTGGTCGCCATCGCCTCGAATGGCGGCGGTAAGC
AGGCGCTGGAAACAGTACAGCGCCTGCTGCCTGTACTGTGCCAGGATCA
TGGACTGACACCCGAACAGGTGGTCGCCATTGCTTCCCACGACGGAGGA
TCGGCCAGCCTTGGAGTCCATCGTAGCCCAATTGTCCAGGCCCGATCCC
GCGTTGGCTGCGTTAACGAATGACCATCTGGTGGCGTTGGCATGTCTTG
GTGGACGACCCGCGCTCGATGCAGTCAAAAAGGGTCTGCCTCATGCTCC
CGCATTGATCAAAAGAACCAACCGGCGGATTCCCGAGAGAACTTCCCAT
CGAGTCGCGGGATCCCAACTAGTCAAAAGTGAACTGGAGGAGAAGAAAT
CTGAACTTCGTCATAAATTGAAATATGTGCCTCATGAATATATTGAATT
AATTGAAATTGCCAGAAATTCCACTCAGGATAGAATTCTGAAATGAAGG
TAATGGAATTTTTTATGAAAGTTTATGGATATAGAGGTAAACATTTGGG
TGGATCAAGGAAACCGGACGGAGCAATTTATACTGTCGGATCTCCTATT
GATTACGGTGTGATCGTGGATACTAAAGCTTATAGCGGAGGTTATAATC
TGCCAATTGGCCAAGCAGATGAAATGCAACGATATGTCGAAGAAAATCA
AACACGAAACAAACATATCAACCCTAATGAATGGTGGAAAGTCTATCCA
TCTTCTGTAACGGAATTTAAGTTTTTATTTGTGAGTGGTCACTTTAAAG
GAAACTACAAAGCTCAGCTTACACGATTAAATCATATCACTAATTGTAA
TGGAGCTGTTCTTAGTGTAGAAGAGCTTTTAATTGGTGGAGAAATGATT
AAAGCCGGCACATTAACCTTAGAGGAAGTCAGACGGAAATTTAATAACG
GCGAGATAAACTTTTAA
```

Sequence encoding TAL Right Arm+FokI monomer (SEQ ID NO: 58)

```
ATGGACTACAAAGACCATGACGGTGATTATAAAGATCATGACATCGATT
ACAAGGATGACGATGACAAGATGGCCCCCAAGAAGAAGAGGAAGGTGGG
CATTCACCGCGGGGTACCTATGGTGGACTTGAGGACACTCGGTTATTCG
CCAACAGCAACAGGAGAAAATAAGCCTAAGGTCAGGAGCACCGTCGCGC
AACACCACGAGGCGCTTGTGGGGCATGGCTTCACTCATGCGCATATTGT
CGCGCTTTCACAGCACCCTGCGGCGCTTGGGACGGTGGCTGTCAAATAC
CAAGATATGATTGCGGCCCTGCCCGAAGCCACGCACGAGGCAATTGTAG
GGGTCGGTAAACAGTGGTCGGAGCGCGAGCACTTGAGGCGCTGCTGAC
TGTGGCGGGTGAGCTTAGGGGGCCTCCGCTCCAGCTCGACACCGGGCAG
CTGCTGAAGATCGCGAAGAGAGGGGGAGTAACAGCGGTAGAGGCAGTGC
ACGCCTGGCGCAATGCGCTCACCGGGGCCCCCTTGAACCTGACCCCAGA
CCAGGTAGTCGCAATCGCGTCACATGACGGGGGAAAGCAAGCCCTGGAA
ACCGTGCAAAGGTTGTTGCCGGTCCTTTGTCAAGACCACGGCCTTACAC
CGGAGCAAGTCGTGGCCATTGCATCCCACGACGGTGGCAAACAGGCTCT
TGAGACGGTTCAGAGACTTCTCCCAGTTCTCTGTCAAGCCCACGGGCTG
ACTCCCGATCAAGTTGTAGCGATTGCGTCGCATGACGGAGGGAAACAAG
CATTGGAGACTGTCCAACGGCTCCTTCCCGTGTTGTGTCAAGCCCACGG
TTTGACGCCTGCACAAGTGGTCGCCATCGCCTCGAATGGCGGCGGTAAG
CAGGCGCTGGAAACAGTACAGCGCCTGCTGCCTGTACTGTGCCAGGATC
ATGGACTGACCCCAGACCAGGTAGTCGCAATCGCGAACAATAATGGGGG
AAAGCAAGCCCTGGAAACCGTGCAAAGGTTGTTGCCGGTCCTTTGTCAA
GACCACGGCCTTACACCGGAGCAAGTCGTGGCCATTGCAAGCAACATCG
GTGGCAAACAGGCTCTTGAGACGGTTCAGAGACTTCTCCCAGTTCTCTG
TCAAGCCCACGGGCTGACTCCCGATCAAGTTGTAGCGATTGCGTCGCAT
GACGGAGGGAAACAAGCATTGGAGACTGTCCAACGGCTCCTTCCCGTGT
TGTGTCAAGCCCACGGTTTGACGCCTGCACAAGTGGTCGCCATCGCCAG
CCATGATGGCGGTAAGCAGGCGCTGGAAACAGTACAGCGCCTGCTGCCT
GTACTGTGCCAGGATCATGGACTGACCCCAGACCAGGTAGTCGCAATCG
CGTCGAACATTGGGGAAAGCAAGCCCTGGAAACCGTGCAAAGGTTGTT
GCCGGTCCTTTGTCAAGACCACGGCCTTACACCGGAGCAAGTCGTGGCC
ATTGCAAGCAATGGGGTGGCAAACAGGCTCTTGAGACGGTTCAGAGAC
TTCTCCCAGTTCTCTGTCAAGCCCACGGGCTGACTCCCGATCAAGTTGT
AGCGATTGCGTCGCATGACGGAGGGAAACAAGCATTGGAGACTGTCCAA
CGGCTCCTTCCCGTGTTGTGTCAAGCCCACGGTTTGACGCCTGCACAAG
TGGTCGCCATCGCCAGCCATGATGGCGGTAAGCAGGCGCTGGAAACAGT
ACAGCGCCTGCTGCCTGTACTGTGCCAGGATCATGGACTGACCCCAGAC
CAGGTAGTCGCAATCGCGTCACATGACGGGGAAAGCAAGCCCTGGAAA
CCGTGCAAAGGTTGTTGCCGGTCCTTTGTCAAGACCACGGCCTTACACC
GGAGCAAGTCGTGGCCATTGCAAATAATAACGGTGGCAAACAGGCTCTT
```

```
GAGACGGTTCAGAGACTTCTCCCAGTTCTCTGTCAAGCCCACGGGCTGA
CTCCCGATCAAGTTGTAGCGATTGCGTCGAACATTGGAGGGAAACAAGC
ATTGGAGACTGTCCAACGGCTCCTTCCCGTGTTGTGTCAAGCCCACGGT
TTGACGCCTGCACAAGTGGTCGCCATCGCCAACAACAACGGCGGTAAGC
AGGCGCTGGAAACAGTACAGCGCCTGCTGCCTGTACTGTGCCAGGATCA
TGGACTGACACCCGAACAGGTGGTCGCCATTGCTTCTAACATCGGAGGA
CGGCCAGCCTTGGAGTCCATCGTAGCCCAATTGTCCAGGCCCGATCCCG
CGTTGGCTGCGTTAACGAATGACCATCTGGTGGCGTTGGCATGTCTTGG
TGGACGACCCGCGCTCGATGCAGTCAAAAAGGGTCTGCCTCATGCTCCC
GCATTGATCAAAAGAACCAACCGGCGGATTCCCGAGAGAACTTCCCATC
GAGTCGCGGGATCCCAACTAGTCAAAAGTGAACTGGAGGAGAAGAAATC
TGAACTTCGTCATAAATTGAAATATGTGCCTCATGAATATATTGAATTA
ATTGAAATTGCCAGAAATTCCACTCAGGATAGAATTCTTGAAATGAAGG
TAATGGAATTTTTTATGAAAGTTTATGGATATAGAGGTAAACATTTGGG
TGGATCAAGGAAACCGGACGGAGCAATTTATACTGTCGGATCTCCTATT
GATTACGGTGTGATCGTGGATACTAAAGCTTATAGCGGAGGTTATAATC
TGCCAATTGGCCAAGCAGATGAAATGCAACGATATGTCGAAGAAATCA
AACACGAAACAAACATATCAACCCTAATGAATGGTGGAAAGTCTATCCA
TCTTCTGTAACGGAATTTAAGTTTTTATTTGTGAGTGGTCACTTTAAAG
GAAACTACAAAGCTCAGCTTACACGATTAAATCATATCACTAATTGTAA
TGGAGCTGTTCTTAGTGTAGAAGAGCTTTTAATTGGTGGAGAAATGATT
AAAGCCGGCACATTAACCTTAGAGGAAGTCAGACGGAAATTTAATAACG
GCGAGATAAACTTTTAA
```

TAL Left Arm+FokI monomer amino acid sequence (SEQ ID NO:59) encoded by SEQ ID NO: 54, RVDs boxed, FokI Domain underlined:

```
MDYKDHDGDYKDHDIDYKDDDDKMAPKKKRKVGIHRGVPMVDLRTLGYS
QQQQEKIKPKVRSTVAQHHEALVGHGFTHAHIVALSQHPAALGTVAVKY
QDMIAALPEATHEAIVGVGKQWSGARALEALLTVAGELRGPPLQLDTGQ
LLKIAKRGGVTAVEAVHAWRNALTGAPLNLTPDQVVAIAS[NN]GGKQALE
TVQRLLPVLCQDHGLTPEQVVAIAS[NI]GGKQALETVQRLLPVLCQAHGL
TPDQVVAIAS[NI]GGKQALETVQRLLPVLCQAHGLTPAQVVAIAN[NN]GGK
QALETVQRLLPVLCQDHGLTPDQVVAIAS[NI]GGKQALETVQRLLPVLCQ
DHGLTPEQVVAIAS[HD]GGKQALETVQRLLPVLCQAHGLTPDQVVAIAS[NI]
GGKQALETVQRLLPVLCQAHGLTPAQVVAIAN[NN]GGKQALETVQRLLP
VLCQDHGLTPDQVVAIAS[HD]GGKQALETVQRLLPVLCQDHGLTPEQVVA
IAS[NG]GGKQALETVQRLLPVLCQAHGLTPDQVVAIAS[NI]GGKQALETVQ
RLLPVLCQAHGLTPAQVVAIAS[HD]GGKQALETVQRLLPVLCQDHGLTPD
QVVAIAS[NI]GGKQALETVQRLLPVLCQDHGLTPEQVVAIAN[NN]GGKQAL
ETVQRLLPVLCQAHGLTPDQVVAIAS[NG]GGKQALETVQRLLPVLCQAHG
LTPAQVVAIAS[NG]GGKQALETVQRLLPVLCQDHGLTPEQVVAIAS[HD]GG
RPALESIVAQLSRPDPALAALTNDHLVALACLGGRPALDAVKKGLPHAP
ALIKRTNRRIPERTSHRVAGSQLVKSELEEKKSELRHKLKYVPHEYIEL
IEIARNSTQDRILEMKVMEFFMKVYGYRGKHLGGSRKPDGAIYTVGSPI
DYGVIVDTKAYSGGYNLPIGQADEMQRYVEENQTRNKHINPNEWWKVYP
SSVTEFKFLFVSGHFKGNYKAQLTRLNHITNCNGAVLSVEELLIGGEMI
KAGTLTLEEVRRKFNNGEINF
```

TAL Right Arm+FokI monomer amino acid sequence (SEQ ID NO:60) encoded by SEQ ID NO: 58, RVDs boxed, FokI Domain underlined:

```
MDYKDHDGDYKDHDIDYKDDDDKMAPKKKRKVGIHRGVPMVDLRTLGYS
QQQQEKIKPKVRSTVAQHHEALVGHGFTHAHIVALSQHPAALGTVAVKY
QDMIAALPEATHEAIVGVGKQWSGARALEALLTVAGELRGPPLQLDTGQ
LLKIAKRGGVTAVEAVHAWRNALTGAPLNLTPDQVVAIAS[HD]GGKQALE
TVQRLLPVLCQDHGLTPEQVVAIAS[HD]GGKQALETVQRLLPVLCQAHGL
TPDQVVAIAS[HD]GGKQALETVQRLLPVLCQAHGLTPAQVVAIAS[NG]GGK
QALETVQRLLPVLCQDHGLTPDQVVAIAN[NN]GGKQALETVQRLLPVLCQ
DHGLTPEQVVAIAS[NI]GGKQALETVQRLLPVLCQAHGLTPDQVVAIAS[H
D]GGKQALETVQRLLPVLCQAHGLTPAQVVAIAS[HD]GGKQALETVQRLLP
VLCQDHGLTPDQVVAIAS[NI]GGKQALETVQRLLPVLCQDHGLTPEQVVA
IAS[NG]GGKQALETVQRLLPVLCQAHGLTPDQVVAIAS[HD]GGKQALETVQ
RLLPVLCQAHGLTPAQVVAIAS[HD]GGKQALETVQRLLPVLCQDHGLTPD
QVVAIAS[HD]GGKQALETVQRLLPVLCQDHGLTPEQVVAIAN[NN]GGKQAL
ETVQRLLPVLCQAHGLTPDQVVAIAS[NI]GGKQALETVQRLLPVLCQAHG
LTPAQVVAIAN[NN]GGKQALETVQRLLPVLCQDHGLTPEQVVAIAS[NI]GG
RPALESIVAQLSRPDPALAALTNDHLVALACLGGRPALDAVKKGLPHAP
ALIKRTNRRIPERTSHRVAGSQLVKSELEEKKSELRHKLKYVPHEYIEL
IEIARNSTQDRILEMKVMEFFMKVYGYRGKHLGGSRKPDGAIYIYTVGS
PIDYGVIVDTKAYSGGYNLPIGQADEMQRYVEENQTRNKHINPNEWWKV
YPSSVTEFKFLFVSGHFKGNYKAQLTRLNHITNCNGAVLSVEELLIGGE
MIKAGTLTLEEVRRKFNNGEINF
```

The TAL Left Arm Sequence (SEQ ID NO: 30) and TAL Right Arm Sequence (SEQ ID NO:31) were initially cloned into pUC57. These were digested using restriction endonucleases (BbsI/BsaI) to create specific overhangs that allowed them to be cloned into the matching backbones (from Addgene; #32285, #32287-digested with BsmBI). They were then transferred to FokI expression vectors JDS70 (SNI/A 0.5 Domain) and JDS71 (SHD/C 0.5 Domain) (FokI) plasmids (Addgene 32285, 32287). Each backbone contained ½ of the domain for the last RVD, as well as the FokI domain, at the 3' end. At the 5' end, the backbone contains the T7 RNA binding site (necessary for making the mRNA) as well as the start codon and nuclear localization signal.

The TAL repeat variable diresidue (RVD) effector binding sites for the rd8 region were designed such that they scored for high specificity in silico using a scoring function developed by Moscou and Bogdanove, described in supplementary script S1 of the paper Moscou, M. J. and Bogdanove, A. J. (2009) Science. 326(5959):1501. The scoring function is based on RVD-nucleotide association frequencies for known TAL-effector target pairs. Each RVD-nucleotide pair in the TAL effector/target alignment is assigned a probability score based on these association frequencies. Scores for all RVD-nucleotide pairs are summed to score the entire alignment.

The amino acids of the TAL Left Arm RVDs are: NN, NI, NI, NN, NI, HD, NI, NN, HD, NG, NI, HD, NI, NN, NG, NG, HD, sequentially listed as present in the Tal Left Arm protein, where NI=A, HD=C, NG=T, NN=R (G or A), and NS=N (A, C, G, or T) in the target DNA.

The amino acids of the TAL Right Arm RVDs are: HD, HD, HD, NG, NN, NI, HD, HD, NI, NG, HD, HD, HD, NN, NI, NN, NI, sequentially listed as present in the Tal Right Arm protein, where NI=A, HD=C, NG=T, NN=R (G or A), and NS=N (A, C, G, or T) in the target DNA. In Table 4 and Table 5 the top four scores are summarized. The first locus [139237058, 139237108] is the Crb1 gene, flanking the rd8 region. Table 5 shows that the score rises rapidly indicating the lack of specificity for other loci as alternative (less frequent) binding, i.e. it is highly unlikely that the TALE will bind other sites and create undesired deletions. Further, the spacer length between TALENs increases, again reducing the probability of a successful cut in DNA loci outside Crb1 gene. In summary, the developed TALEN for Crb1 correction are believed to be highly specific for mouse.

nucleic acid sequence or protein. Variants of a nucleic acid sequence or protein described herein are characterized by conserved functional properties compared to the corresponding nucleic acid sequence or protein.

Mutations can be introduced using standard molecular biology techniques, such as chemical synthesis, site-directed mutagenesis and PCR-mediated mutagenesis.

One of skill in the art will recognize that one or more amino acid mutations can be introduced without altering the functional properties of nucleases, TALEN proteins or TAL proteins. For example, one or more amino acid substitutions, additions, or deletions can be made without altering the functional properties of nucleases, TALEN proteins or TAL proteins.

When comparing a reference protein to a putative homologue, amino acid similarity may be considered in addition to identity of amino acids at corresponding positions in an amino acid sequence. "Amino acid similarity" refers to amino acid identity and conservative amino acid substitutions in a putative homologue compared to the corresponding amino acid positions in a reference protein.

Conservative amino acid substitutions can be made in reference proteins to produce variants.

Conservative amino acid substitutions are art recognized substitutions of one amino acid for another amino acid having similar characteristics. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include

TABLE 4

| Mouse Chromosome Locus | TAL1 | TAL2 | TAL1 Target | TAL2 Target |
|---|---|---|---|---|
| 1 [139237058, 139237108] | RVD2 | RVD1 | T CCCTGACCATCCCGAGA (SEQ ID NO: 34) | T GAAGACAGCTACAGTTC (SEQ ID NO: 38) |
| 2 [10578886, 10578946] | RVD2 | RVD1 | T CCCTGCCCACCCCGAGA (SEQ ID NO: 35) | T ACAAACAGCTCCTAATC (SEQ ID NO: 39) |
| 1 [64814572, 64814625] | RVD2 | RVD1 | T CCCTCCCCAGCCCAAAA (SEQ ID NO: 36) | T AAAAACAGCAACAGCAA (SEQ ID NO: 40) |
| 10 [19148423, 19148486] | RVD1 | RVD1 | T TAAAACAACTACAGTTT (SEQ ID NO: 37) | T GCCAACACCCACATCTC (SEQ ID NO: 41) |

TABLE 5

| Mouse Chromosome Locus | TAL1 | TAL2 | TAL1 Score | TAL2 Score | TAL1 + TAL2 Score | Spacer Length |
|---|---|---|---|---|---|---|
| 1 [139237058, 139237108] | RVD2 | RVD1 | 4.97 | 5.81 | 10.78 | 17 |
| 2 [10578886, 10578946] | RVD2 | RVD1 | 9.01 | 16.01 | 25.02 | 27 |
| 1 [64814572, 64814625] | RVD2 | RVD1 | 11.46 | 14.55 | 26.01 | 20 |
| 10 [19148423, 19148486] | RVD1 | RVD1 | 11.5 | 17.2 | 28.7 | 30 |

Variants

As used herein, the term "variant" refers a variation of a nucleic acid sequence or protein described herein which one or more nucleotides or amino acid residues have been modified by nucleotide or amino acid substitution, addition, or deletion while retaining the function of the reference isoleucine, leucine and valine; aromatic amino acids include phenylalanine, glycine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size, alanine, cysteine, aspartate, glycine, asparagine, proline, threonine, serine, valine, all typically considered to be small.

A variant can include synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, 3-methylhistidine, and ornithine.

With regard to nucleic acids, it will be appreciated by those of skill in the art that due to the degenerate nature of the genetic code, multiple nucleic acid sequences can encode a particular protein, and that such alternate nucleic acids may be used in compositions and methods of the present invention.

Percent identity is determined by comparison of amino acid or nucleic acid sequences, including a reference amino acid or nucleic acid sequence and a putative homologue amino acid or nucleic acid sequence. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). The two sequences compared are generally the same length or nearly the same length.

The determination of percent identity between two sequences can also be accomplished using a mathematical algorithm. Algorithms used for determination of percent identity illustratively include the algorithms of S. Karlin and S. Altshul, PNAS, 90:5873-5877, 1993; T. Smith and M. Waterman, Adv. Appl. Math. 2:482-489, 1981, S. Needleman and C. Wunsch, J. Mol. Biol., 48:443-453, 1970, W. Pearson and D. Lipman, PNAS, 85:2444-2448, 1988 and others incorporated into computerized implementations such as, but not limited to, GAP, BESTFIT, FASTA, TFASTA; and BLAST, for example incorporated in the Wisconsin Genetics Software Package, Genetics Computer Group, 575 Science Drive, Madison, Wis.) and publicly available from the National Center for Biotechnology Information.

A non-limiting example of a mathematical algorithm utilized for the comparison of two sequences is the algorithm of Karlin and Altschul, 1990, PNAS 87:2264-2268, modified as in Karlin and Altschul, 1993, PNAS. 90:5873-5877. Such an algorithm is incorporated into the NBLAST and XBLAST programs of Altschul et al., 1990, J. Mol. Biol. 215:403. BLAST nucleotide searches are performed with the NBLAST nucleotide program parameters set, e.g., for score=100, word length=12 to obtain nucleotide sequences homologous to a nucleic acid molecules of the present invention. BLAST protein searches are performed with the XBLAST program parameters set, e.g., to score 50, word length=3 to obtain amino acid sequences homologous to a protein molecule of the present invention. To obtain gapped alignments for comparison purposes, Gapped BLAST are utilized as described in Altschul et al., 1997, Nucleic Acids Res. 25:3389-3402. Alternatively, PSI BLAST is used to perform an iterated search which detects distant relationships between molecules. When utilizing BLAST, Gapped BLAST, and PSI Blast programs, the default parameters of the respective programs (e.g., of XBLAST and NBLAST) are used. Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used.

The percent identity between two sequences is determined using techniques similar to those described above, with or without allowing gaps. In calculating percent identity, typically only exact matches are counted.

One of skill in the art will recognize that one or more nucleic acid or amino acid mutations can be introduced without altering the functional properties of a given nucleic acid or protein, respectively.

It is appreciated that due to the degenerate nature of the genetic code, alternate nucleic acid sequences encode nucleases, TALEN proteins or TAL proteins and variants thereof, and that such alternate nucleic acids may be included in an expression vector and, expressed to produce nucleases, TALEN proteins or TAL proteins of the present invention.

TAL Left Arm (SEQ ID NO:33) is encoded by SEQ ID NO:32. Due to the degenerate nature of the genetic code, alternate nucleic acid sequences encode the TAL Left Arm of SEQ ID NO:33 and variants thereof, and that such alternate nucleic acids may be included in an expression vector and expressed to produce the TAL Left Arm of SEQ ID NO:33 and variants thereof of the present invention.

According to aspects of the present invention a variant of TAL Left Arm has at least 85%, at least 86%, at least 87% at least 88%, at least 89%, at least 90%, at least 91%, at least 92%, at least 93%, at least 94%, at least 95%, at least 96%, at least 97%, at least 98%, at least 99% identity, or greater identity, to SEQ ID NO:33, wherein the variant binds the desired target.

TAL Right Arm (SEQ ID NO:62) is encoded by SEQ ID NO:61. Due to the degenerate nature of the genetic code, alternate nucleic acid sequences encode the TAL Right Arm of SEQ ID NO:62 and variants thereof, and that such alternate nucleic acids may be included in an expression vector and expressed to produce the TAL Right Arm of SEQ ID NO:62 and variants thereof of the present invention.

According to aspects of the present invention a variant of TAL Right Arm has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identity, or greater identity, to SEQ ID NO:62, wherein the variant binds the desired target.

TAL Left Arm+FokI monomer (SEQ ID NO:59) is encoded by SEQ ID NO:54. Due to the degenerate nature of the genetic code, alternate nucleic acid sequences encode the TAL Left Arm+FokI monomer of SEQ ID NO:59 and variants thereof, and that such alternate nucleic acids may be included in an expression vector and expressed to produce the TAL Left Arm+FokI monomer of SEQ ID NO:59 and variants thereof of the present invention.

According to aspects of the present invention a variant of TAL Left Arm+FokI monomer has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identity, or greater identity, to SEQ ID NO:59, wherein the variant binds the desired target.

TAL Right Arm+FokI monomer (SEQ ID NO:60) is encoded by SEQ ID NO:58. Due to the degenerate nature of the genetic code, alternate nucleic acid sequences encode the TAL Right Arm+FokI monomer of SEQ ID NO:60 and variants thereof, and that such alternate nucleic acids may be included in an expression vector and expressed to produce the TAL Right Arm+FokI monomer of SEQ ID NO:60 and variants thereof of the present invention.

According to aspects of the present invention a variant of TAL Right Arm+FokI monomer has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identity, or greater identity, to SEQ ID NO:60, wherein the variant binds the desired target.

Variants of donor oligonucleotides disclosed herein may be used to correct Crb1<rd8>. For example, donor oligonucleotide variants may correct the Crb1<rd8> to produce a variant Crb1 protein, as long as the variant Crb1 protein functions normally in the mouse.

According to aspects of the present invention a donor oligonucleotide has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identity, or greater identity, to any of SEQ ID NO:1, SEQ ID NO:2, SEQ ID NO:3, SEQ ID NO:4, wherein the variant encodes an amino acid sequence identical to the amino acid sequence encoded by SEQ ID NO:1, SEQ ID NO:2, SEQ ID NO:3 or SEQ ID NO:4.

Donor nucleotide variants include those which are not identical to those disclosed herein but which, due to the degeneracy of the genetic code, encode the desired portion of wild-type Crb1.

The term "nucleic acid" refers to RNA or DNA molecules having more than one nucleotide in any form including single-stranded, double-stranded, oligonucleotide or polynucleotide. The term "nucleotide sequence" refers to the ordering of nucleotides in an oligonucleotide or polynucleotide in a single-stranded form of nucleic acid.

The term "complementary" refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA- is 100% complementary to a region of the nucleotide sequence 5'-TTAGCTGG-3'.

The terms "hybridization" and "hybridizes" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term "stringency of hybridization conditions" refers to conditions of temperature, ionic strength, and composition of a hybridization medium with respect to particular common additives such as formamide and Denhardt's solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize.

The terms "specific hybridization" and "specifically hybridizes" refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

An example of high stringency hybridization conditions is hybridization of nucleic acids over about 100 nucleotides in length in a solution containing 6×SSC, 5× Denhardt's solution, 30% formamide, and 100 micrograms/ml denatured salmon sperm at 37° C. overnight followed by washing in a solution of 0.1×SSC and 0.1% SDS at 60° C. for 15 minutes. SSC is 0.15M NaCl/0.015M Na citrate. Denhardt's solution is 0.02% bovine serum albumin/0.02% FICOLL/0.02% polyvinylpyrrolidone.

Embodiments of inventive compositions and methods are illustrated in the following examples. These examples are provided for illustrative purposes and are not considered limitations on the scope of inventive compositions and methods.

EXAMPLES

Example 1

Correction Of Crb1rd8 Mutation in C57BL/6NJ Mice

FIGS. 1A and 1B show schematic illustrations of a method for correction of Crb1rd8 mutation in C57BL/6NJ mice of the present invention including introducing a double-strand break near the point mutation found in Crb1rd8, using mRNAs encoding TALEN microinjected into zygotes. To promote homology-directed repair (HDR) at the site of the Crb1rd8 mutation, single-stranded oligodeoxynucleotides (ssODNs) were designed with homology to the region mediating a precise HDR at the TALEN-induced double-stranded break. Single-stranded DNA was used in this method as it is 100-fold less likely to integrate by illegitimate recombination compared with double-stranded DNA.

Example 2

TALEN Design and Making

The TALENs used here were designed using the "ZiFiT" program, zifit.partners.org/ZiFiT/ChoiceMenu.aspx described in Sander et al, 2011; Sander et al, 2010; Sander et al, 2007. The two TAL coding regions were synthesized by GenScript USA Inc., and cloned into nuclease expression vectors JDS70 (SNI/A 0.5 Domain) and JDS71 (SHD/C 0.5 Domain) (FokI) plasmids (Addgene 32285, 32287, Sander et al, 2011) encoding FokI monomers and leading to functional TALENs following transcription and translation. The left side TAL was designed to bind 5'TGAAGACAGCTACA-GTTC (SEQ ID NO: 38); with an intervening sequence 5'TTATGGTGTGCCTGTC (SEQ ID NO: 47); the right side TAL was designed to bind 5'TCTCGGGATGGTCAGGGA (SEQ ID NO: 48). These sequences correspond to the native condition of the rd8 mutation of the Crb1 gene in C57BL/6N mouse strain.

To make capped mRNA the AmpliCap-Max™ T 7 High Yield Message Maker Kit was used (Cellscript Cat. No. C-ACM04037) and A-Plus™ Poly(A) Polymerase Tailing Kit (Cellscript Cat No. C-PAP5104H). The template for the mRNA transcription was the TALEN-containing plasmids (using endogenous T7 promoters in JDS70 and JDS71), linearized using PmeI endonuclease (NEB Cat No. R0560S), and purified using phenol-chloroform extraction. The mRNA was purified using ammonium acetate precipitation (protocol outlined in the Cellscript kits).

Example 3

Oligonucleotide Design for Crb1 Correction

A series of four single-stranded Crb1rd8 correction ssODNs (200mer and 52mer, in sense and antisense directions) with homology centered to the targeted region was synthesized with the aim to achieve homology-directed repair (HDR). In addition to the replacement of the deleted nucleotide ("C/G") in the Crb1rd8 mutation, these ssODNs were designed to incorporate five synonymous base substitutions inside the TALEN binding regions as shown in FIGS. 1A and 1B. These substitutions, selected to maintain amino acid usage and codon usage frequency, were designed to prevent further modification by the TALENs post-repair, and also to differentiate the repaired locus from the C57BL/6J wild-type allele. They are further used here in a single-nucleotide polymorphism (SNP) assay to identify illegitimate recombination, i.e. off-target effects of the oligonucleotides.

Sense strands and their complement (anti-sense) strands were prepared, see Table 3 which shows the sequences for the ssODNs, SEQ ID NO:1, SEQ ID NO:2, SEQ ID NO:3 and SEQ ID NO:4.

For all four oligonucleotides, the sequences were chosen to be homologous to the targeted region in the Crb1 gene with the exceptions that one nucleotide has been added, either C or in the case of the reverse complement G. The 200mer nucleotide oligonucleotide used was TTCTA-CAAATATGGTACTTACTGGCTGTTTGCCATCAAAT-GCCTGCCACTCCAGCCCC TGTTTGCATGGAG-GAAACTGTGAAGACAGTTACAGCAGTTATCGGTGT GCCTGTCTG TCGGGATGGTCAGGGACACACTGT-GAAATCAACATTGATGAGTGCTTTTCTAGCCCC TGTATCCATGGCAACTGCTCTGATGGAG (SEQ ID NO: 1) and for the reverse complement CTCCATCA-GAGCAGTTGCCATGGATACAGGGGCTA-GAAAAGCACTCATCAATGTTG ATTTCACAGTGT-GTCCCTGACCATCCCGACAGACAGGCACACCGATA ACTGCTGTAA CTGTCTTCACAGTTTCCTCCATG-CAAACAGGGGCTGGAGTGGCAGGCATTTGATGGC AAACAGCCAGTAAGTACCATATTTGTAGAA (SEQ ID NO: 2). The 52mer nucleotide oligonucleotide used was TGAAGACAGTTACAGCAGTTATCGGTGTGCCT-GTCTGTCGGGATGGTCAGGG (SEQ ID NO: 3) and for the reverse complement CCCTGACCATCCCGACA-GACAGGCACACCGATAACTGCTGTAACTGTCTTCA (SEQ ID NO: 4).

As noted above, five other base substitutions were made to differentiate the rd8 mutation correction from the C57BL/6J wild type sequence. These additional substitutions were incorporated into all oligonucleotides (200-mer or 52-mers, sense and antisense strands), and are highlighted by underlining, and the additional G is shown in bold and underlined, for the sense strand: GACAG<u>T</u>TACAG <u>C</u>AG<u>T</u>TATCGGTGTGCCTGTCT<u>G</u>TC (SEQ ID NO: 20). The antisense strand included complementary exchanges.

Example 4

Pronuclear Injection of TALEN Plus 200mer Oligonucleotides

Fertilized C57BL/6NJ oocytes, which carry the rd8 mutation, were isolated from superovulated, mated females for microinjections. TALEN mRNAs at 10, 25, or 50 ng/ul plus 1 ng/ul of 200mer (sense or complementary strand separately) oligonucleotides (synthesized by Integrated DNA Technologies, Inc) were prepared in TE buffer (10 mM Tris, pH 7.5, 1 mM EDTA) and microinjected into the pronuclei of oocytes, using approximately 2-5 picoliters into one pronucleus/oocyte. The TALEN RNAs were capped and polyadenylated. The oligonucleotides were co-injected with the TALEN mRNA to instigate homology-directed repair of the genomic DNA.

Post microinjection, about 20 embryos were introduced into one pseudopregnant female and carried to term. Pups were born after about three weeks. About three weeks after birth, mice were weaned, and 25% of oocytes using the 200mer sense strand oligonucleotide and 29% of oocytes using the 200mer complementary strand oligonucleotide had survived the microinjection and embryo transfer procedure giving rise to live born. DNA was isolated by alkaline lysis from samples of tail tissue obtained from the live born mice for further analysis.

Example 5

Pronuclear Injection of TALEN Plus 52mer Oligonucleotides

Fertilized C57BL/6NJ oocytes, which carry the rd8 mutation, were isolated from superovulated, mated females for microinjections. TALEN mRNAs at 50 ng/ul plus 0.3 ng/ul, 2 ng/ul or 6 ng/ul of 52mer (sense or complementary strand) oligonucleotides (synthesized by Integrated DNA Technologies, Inc.) were prepared in TE buffer and microinjected into the pronuclei of oocytes, at approximately 2-5 picoliters into one pronucleus/oocyte. The TALEN RNAs were capped and polyadenylated. The oligonucleotides were co-injected with the TALEN mRNA to instigate homology-directed repair of the genomic DNA.

Microinjected embryos (~20/female) were introduced into pseudopregnant females and carried to term. At wean 16% of oocytes using the 52mer sense strand oligonucleotide and 26% of oocytes using the 52mer complementary strand oligonucleotide had survived the microinjection and embryo transfer procedure to live born. DNA was isolated by alkaline lysis from samples of tail tissue obtained from the live born mice for further analysis.

Example 6

PCR Analysis of Putative Rd8 Homology-Directed Repair

PCR primers were designed to detect the presence of the six changed bases which included the corrected gene base, in the Crb1 region. This was done by designing a multiplex PCR. This used PCR primers #1303 FWD WT PRIMER 5'GGGAAAGCTTCCCAGACTGACAAT (SEQ ID NO: 49) and #1353 REV WT PRIMER 5'CGACCAGACAC-CCTTTGTGATAAG (SEQ ID NO: 50) which provide a visible single band of 659 bp for the wild type Crb1<rd8>mutation. Using primers #1353 REV WT PRIMER and 1368 FWD WT PRIMER 5'CAGACAGGCA-CACCGATAACTG (SEQ ID NO: 51) will visualize a single band only when a correct targeting event in the Crb1<rd8> locus has occurred, and where an oligonucleotide (200mer or 52mer, sense or complementary antisense) has been incorporated with a band size of 330 bp. The PCR can also be performed using all three primers in the reaction, and the 330 bp is only detectable if the corrected allele is present.

When non-homologous end joining (NHEJ) occurs, leading to large deletions (>25 bp to <611 bp), the band size is visibly reduced. Smaller NHEJ events are detected by sequencing using primers #1303 and #1353. All PCR products produced were sequenced to verify NHEJ events.

PCR was performed using primers 1303 and 1353 and analyzed following approaches well established in the art. The cycles used were one heat step at 95° C. for 30 s, followed by 30 cycles of 95° C. for 15 s, 64° C. for 30 s, followed by 1 min at 68° C.; and after the 30 cycles finished with one 5 min step at 68° C., followed by a 4° C. to hold until further use.

To confirm the alleles by sequencing the primers 1303 and 1353 were used. Sequencing was done as known in the art. See FIG. 2 for a sample.

Example 7

Analysis from TALEN Plus ssODN Pronuclear Injection

Mice obtained as described hereinabove were analyzed by PCR genotyping as described.

Figure 4:
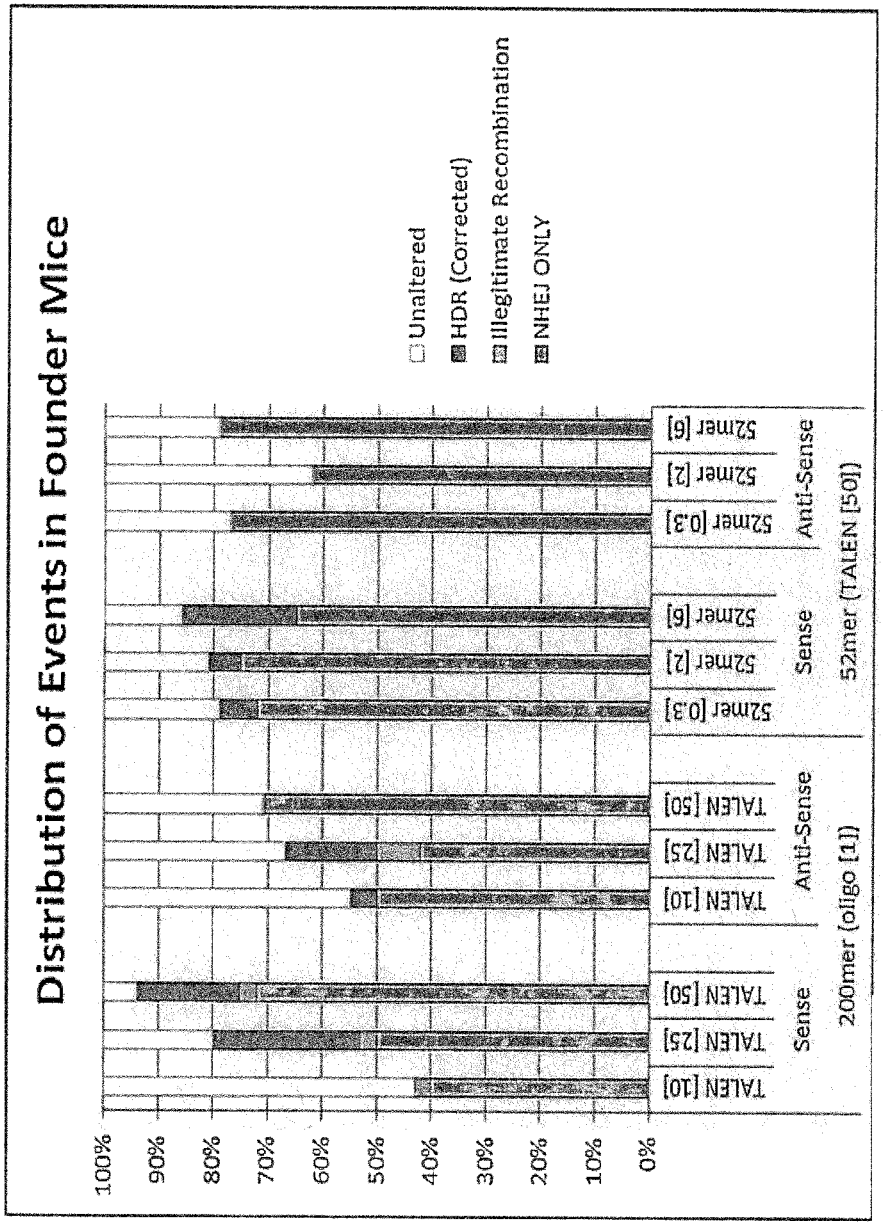
FIG. 4 is a bar graph showing the percent of TALEN-mediated events in live born founders for each indicated condition.

FIG. 4 is a bar graph showing the percent TALEN mediated events in live born founders for each experimental condition, square brackets for the variable in ng/µl.

As FIG. 4 illustrates, the TALEN pair used in this example (plus donor ssODN) provided detectable events in 43%-94% of founder animals under all various conditions used. homology-directed repair (HDR) was variable and detected only under some conditions used. While increasing TALEN mRNAs concentrations microinjected clearly increases the number of TALEN-mediated events, it does not appear to have the same effect on HDR.

Complete data are shown in FIGS. 5 and 6. Note: illegitimate recombination values were not determined for the 52mer-derived mice, nor in any mouse that had a correct ssODN-meditated repair.

FIG. 5 shows the number and percentages of animals born, evidence of TALEN-mediated events, as well as HDR events, and illegitimate recombination events for the 200mer ssODN across all conditions, varying ssODN concentration, and TALEN mRNA concentrations. Results from the subsequently determined optimal condition of 25 ng/µl of TALEN mRNA and 1 ng/µl of the 200mer ssODN are shown in the shaded boxes. Note that the illegitimate recombination values cannot be determined in any mouse that had a correct ssODN-mediated repair.

DNA from the founder mice produced according to methods of the present invention was isolated from tail tips and interrogated using PCR followed by amplicon sequencing. This was used to identify NHEJ indels and the presence of HDR corrected alleles; these data are summarized in FIGS. 5 and 6. Across all treatment groups for the 200mers, the rate of all TALEN-mediated events detected in the founders was 72% and included two apparent biallelic events. Parsing these data to compare the level of HDR between the sense and anti-sense 200mers ssODNs, the sense 200mer resulted in higher HDR rates (18%, 14 of 76 animals) compared with 8% (7 of 86 animals) from the anti-sense 200mer.

FIG. 6 shows the number and percentages of animals born, evidence of TALEN-mediated events, as well as HDR events, and illegitimate recombination events for the 52mer ssODN across all conditions, varying ssODN concentration, and TALEN mRNA concentrations. Note that the illegitimate recombination values cannot be determined for the 52mer-derived mice, nor in any mouse that had a correct ssODN-mediated repair.

Examination of the results from the shorter 52mer Crb1rd8 correction ssODNs showed that the sense strand gave 11% HDR (5 of 44 animals) and the antisense gave 0% (0 of 59 animals); i.e. a combined HDR rate of 5% for the 52mer ssODN in contrast to that of the 13% (21 of 162 animals) with the 200mers.

The optimal condition for HDR using this TALEN/ssODN combination was 25 ng/µl of each TALEN, combined with 1 ng/µl of the sense 200mer, resulting in 27% HDR (8 of 30 animals born). The identical condition using the anti-sense 200mer gives a similar result (17% HDR, 6/36 animals), as does the sense 52mer at 6 ng/µl co-injected with 50 ng/µl TALEN (3 of 14 animals, 21% HDR). No HDR was detected resulting from the anti-sense 52mer experiments.

Example 8

Breeding of HDR Crb1 Founder Mice

A total of 26 founder mice were identified to contain the HDR Crb1 allele events by PCR amplicon sequencing of tail derived DNA. In order to determine if the HDR corrected allele was germline transmissible, HDR founders generated according to methods of the present invention were bred to C57BL/6NJ mice. From this group one mouse was euthanized prior to sexual maturity due to onset of hydrocephaly. Using the remaining 25 animals, breeding was performed to determine heritability for the modified allele and to segregate and detect founder gamete mosaicism. "Perfect" oligonucleotide oligo-mediated repair as judged by the presence of all the synonymous substitutions was evident in litters from 11 of the 23 tested HDR mouse lines. Three founder lines failed to produce any offspring by natural mating. Two lines resulted in offspring that contained the corrected allele, but lacked one of the five synonymous substitutions (upstream from the correcting base), showing evidence of oligonucleotide truncation at the 5' end. Four lines carried the corrected allele but had also a secondary nearby mutation in Crb1 nullifying the functional rd8 correction. Five lines failed to produce carriers in their first litters. Partial insertions of the ssODN were identified in the offspring of some of the founder animals. Mice from two lines contained the correction and 4 bp downstream substitution, lacking the G to C substitution upstream of the correction, see FIGS. 1A and 1B. This truncation has no impact on the predicted functional correction of Crb1. However, four lines produced offspring that contained an upstream G to C substitution as well as the base insertion, but had a secondary indels downstream nullifying the correction. One of these lines also had littermates with the complete insertion, resulting in predicted functional correction, again clearly demonstrating the potentially confounding effects of germline mosaicism. Two founder animals which showed clear biallelic (i.e. homozygous) Crb1rd8 allele correction based on their tail-derived DNA and sequencing proved to be germline mosaic animals, resulting in both unaltered and corrected offspring.

Example 9

Screening for Illegitimate Recombination

To monitor for illegitimate recombination, SNP assays were designed to specifically and differentially recognize the unmodified allele and the central altered sequences of the oligonucleotides within the 200mer. This enables the detection of the 200mer correction ssODN at off-target sites. The 52mer could not be detected by this assay as the SNP primers extend outside its core sequence. These SNP assays were carried out by LGC Genomics LCC, USA (or UK) using a common primer 5'CAGCCCCTGTTTGCATG-GAGGAA (SEQ ID NO: 55), paired with labeled primers distinguishing the Crb1rd8 wild type sequence 5'CCCGASAGACAGGCACACCA (SEQ ID NO: 56) and ssODN modified sequence 5'CCGASAGACAGGCA-CACCG (SEQ ID NO: 57). Overall, the frequency of detectable off-target ssODN sequences for all experiments combined was only 4%, 6 of 141 animals. By way of comparison, the TALEN NHEJ event efficiency was 74%, 196 of 265 animals, and the cumulative rate of HDR was 9.8%, resulting in 26 total potential founder animals.

An example of a corrected C57BL/6N mouse strain characterized by at least 5 single-nucleotide polymorphisms (SNPs), where: 08-015199792-M (rs3709624) is C; 11-004367508-M (rs3659787) is A; 13-041017317-M (rs3722313) is C; 15-057561875-M (rs3702158) is G; 19-049914266-M (rs3724876) is T produced according to methods of the present invention and including a corrected rd8 mutation present in all cells of the mouse is formally called C57BL/6NJ-Crb1em1Mvw/Mvw(JR#022521), abbreviated to Rd8cor.

Example 10

Phenotypic Analysis of C57BL/6N Mice with Corrected Crb1 Gene

Confocal Fluorescence Microscopy of Retinal Flatmounts

The primary Crb1rd8 phenotype is characterized by fragmentation of the external limiting membrane (ELM), a retinal structure formed by adherens junctions between photoreceptor and Müller cells and is recessive.

To examine ELM fragmentation in mice produced according to methods of the present invention and in control mice, the mice were sacrificed by $CO_2$ asphyxiation followed by cervical dislocation and retinal flatmounts were prepared as described in Krebs et al., Invest. Ophthal. Vis. Sci., 2009, 50(6):2956-2965. Briefly, eyes were removed from euthanized mice and immediately fixed on ice in 0.75x phosphate-buffered saline (PBS) containing 4% w/v paraformaldehyde. Eyecups were prepared by dissection below the limbus within 1 h of enucleation and cut radially. The retina was separated from the RPE/choroid/sclera and incubated overnight in the same fixative at 4° C. Retinas were then rinsed twice in PBS and stained for four days at 4° C. in PBS containing 0.5% Triton X-100, rhodamine phalloidin (1 U/ml; Life Technologies, Grand Island, N.Y.) and 4',6-diamidino-2-phenylindole (DAPI; 10 µg/ml; Life Technologies). After staining, samples were rinsed twice with PBS and mounted in Vectashield (Vector Laboratories, Burlingame, Calif.). Confocal microscopy was performed at 63x with an SP5 laser confocal microscope (Leica Microsystems, Buffalo Grove, Ill.). Laser power in each fluorescence channel was adjusted by attenuation compensation to yield similar object intensities through the ELM. Confocal images were analyzed and processed in Imaris 7.6.4 (Bitplane, South Windsor, Conn.) to highlight the external limiting membrane.

Figure 7A:
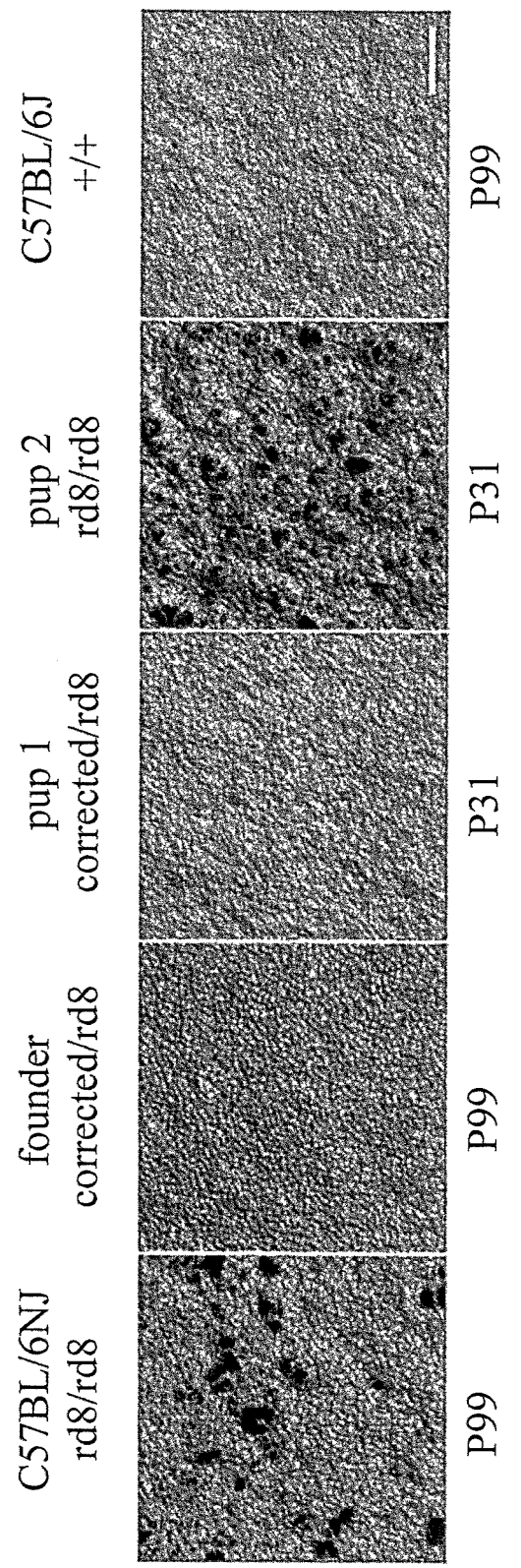
FIG. 7A shows images illustrating correction of Crb1rd8-associated phenotypes by methods of the present invention as evidenced by differences in ELM fragmentation revealed by confocal microscopy of retinal flatmounts stained with rhodamine phalloidin.

Correction of Crb1rd8-associated phenotypes was found as evidenced by differences in ELM fragmentation revealed by confocal microscopy of retinal flatmounts stained with rhodamine phalloidin, FIG. 7A. A founder heterozygous for the corrected allele and its progeny (pups 1 and 2) from a cross with C57BL/6NJ were compared with C57BL/6J and C57BL/6NJ control mice (Crb1 genotype is indicated). The thresholded surface highlights F-actin structures at the ELM. Heterozygous Crb1rd8 offspring and the founder are normal, while homozygous animals show ELM fragmentation. Postnatal age (P) is given in days. Control samples at P31 were similar to those at P99. Bar, 50 µm.

Fundus Imaging and Optical Coherence Tomography

The Crb1rd8 allele is also associated with outer retinal dysplasia, which is correlated with a progressive degeneration of photoreceptor cells. This phenotype varies with strain background and is substantially diminished in all C57BL/6 substrains. Therefore, to test whether the dysplastic phenotype is corrected, offspring of a mating between a corrected founder produced according to methods of the present invention and STOCK-Crb1rd8/J mice which exhibit robust dysplasia were examined.

Following pupil dilation with atropine, right eyes were examined with a Micron III retinal camera (Phoenix Research Laboratories, Pleasanton, Calif.). Video images (100 frames) were acquired at ~30 fps, saved as image stacks in tiff format, and processed in Fiji/ImageJ. Image stacks were first registered in translation and affine modes by using the Image Stabilizer plugin (default settings) on a subset of the image centered on the optic nerve head. Registration coefficients generated in each mode were applied to the full size image stack with the Image Stabilizer Log Applier plugin. Registered image stacks were averaged with Z Project, sharpened in two rounds with Unsharp Mask with a 3.0 pixel radius and Mask Weights of 0.7 and 0.5, respectively, and adjusted for contrast/brightness. Fundus images were oriented in Fiji/Image with the superior and nasal fundus at the top and right, respectively. The degree of rotation required for orientation was determined from the angle of a line drawn from the pupil center to the nose in an image of the mouse head taken with the Micron III camera immediately prior to fundus imaging.

Figure 7B:
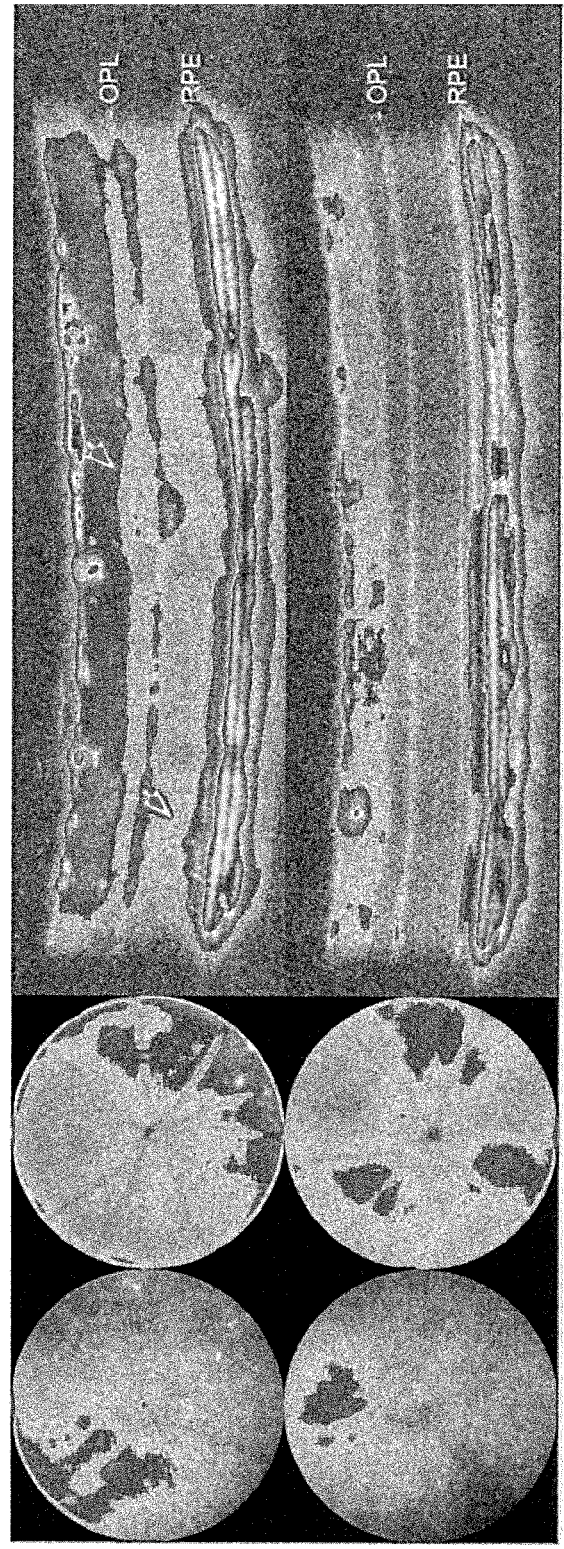
FIG. 7B shows images illustrating correction of Crb1rd8-associated phenotypes by methods of the present invention as evidenced by differences in retinal dysplasia in offspring from a cross between a founder heterozygous for the corrected Crb1 allele and STOCK-Crb1rd8/J.

On the same day as fundus imaging, the same mice were anesthetized with a ketamine/xylazine mixture (0.8 ml ketamine (ketamine KCL injection USP, 100 mg/ml, Butler Animal Health Supply, Dublin, Ohio), 0.8 ml xylazine (xylazine sterile solution, 20 mg/ml, Lloyd, Shenandoah, Iowa) and 3.4 ml 0.9% sodium chloride) and examined with a spectral domain optical coherence tomography (OCT) instrument (Bioptigen, Morrisville, N.C.). Ten volume scans (1000 A-scans per B-scan, 100 B-scans, 1.4 mm rectangular volume generated in enhanced depth imaging mode) were acquired from each animal. Fiji/ImageJ was used to register, average and align neighboring B-scans of the ten image volumes with a custom macro that generates both en face and B-scan stacks of the dataset. The en face image corresponds to a view of the outer nuclear layer obtained by averaging a 40-slice subset of the en face image volume with Z Project. En face views were rotated manually to correspond to the orientation of the fundus image using the shadows of superficial blood vessels as a guide. OCT B-scan images were obtained taken from the same relative position of the image volume in both mice examined. Fundus imaging and optical coherence tomography (OCT) revealed retinal dysplasia in a homozygous Crb1rd8 offspring, but no detectable dysplasia in a heterozygous corrected littermate. FIG. 7B shows the correction of Crb1rd8-associated phenotypes due to use of methods of the present invention as evidenced by differences in retinal dysplasia in offspring from a cross between a founder heterozygous for the corrected Crb1 allele and STOCK-Crb1rd8/J. Pup 3 was homozygous for the uncorrected Crb1rd8 allele (top panels) and showed bright spots in the inferior retina by fundus imaging and in an averaged en face projection of the outer nuclear layer as imaged by OCT. These spots correspond to dysplastic lesions in the outer retina as shown in the OCT B-scan. Dysplasia was not detected in pup 4, a littermate heterozygous for the corrected Crb1 allele, FIG. 7B, bottom panels).

Alternatively, eyes can be stained with hematoxylin and eosin (H&E) for histological analysis. Further retina sections can be analyzed with anti-adherens markers (e.g. anti-beta-catenin; anti-pan-cadherin) to examine the external limiting membrane.

Example 11

Correction of Crb1 in Mouse Strain 5558

Fertilized oocytes from the mouse strain 5558 (B6 (129S4)-Crb1<rd8>/Boc), which carry the rd8 mutation, were isolated from superovulated, mated females for microinjections. TALEN mRNAs at 25 ng/ul plus 1 ng/ul of 200mer (sense strand) oligonucleotide (synthesized by Integrated DNA Technologies, Inc.) were prepared in TB buffer and microinjected into the pronuclei of oocytes, at approximately 2-5 picoliters into one pronucleus/oocyte. The TALEN RNAs were capped and polyadenylated. The oligonucleotides were co-injected with the TALEN mRNA to instigate homology-directed repair of the genomic DNA.

141 microinjected embryos (~20/female) were introduced into pseudopregnant females and carried to term. 42 pups were born and are being analyzed. DNA will be isolated by alkaline lysis from samples of tail tissue obtained from the live born mice for further analysis and mice with the correct Crb1 gene will be used to generate a new substrain.

References

Ansai S, Sakuma T, Yamamoto T, Ariga H, Uemura N, Takahashi R, Kinoshita M (2013) Efficient targeted mutagenesis in medaka using custom-designed transcription activator-like effector nucleases. Genetics 193: 739-749

Barrangou R, Fremaux C, Deveau H, Richards M, Boyaval P, Moineau S. Romero D A, Horvath P (2007) CRISPR provides acquired resistance against viruses in prokaryotes. Science 315: 1709-1712

Bulgakova N A, Knust E (2009) The Crumbs complex: From epithelial-cell polarity to retinal degeneration. Journal of Cell Science 122: 2587-2596

Carbery I D, Ji D, Harrington A, Brown V, Weinstein E J, Liaw L, Cui X (2010) Targeted genome modification in mice using zinc-finger nucleases. Genetics 186: 451-459

Carlson D F, Tan W, Lillico S G, Stverakova D, Proudfoot C, Christian M, Voytas D F, Long C R, Whitelaw C B, Fahrenkrug S C (2012) Efficient TALEN-mediated gene knockout in livestock. PNAS 109: 17382-17387

Carroll D (2012) A CRISPR approach to gene targeting. Molecular Therapy 20: 1658-1660

Chang N, Sun C, Gao L, Zhu D, Xu X, Zhu X, Xiong J W, Xi J J (2013) Genome editing with RNA-guided Cas9 nuclease in Zebrafish embryos. Cell Research 23: 465-472

Cho S W, Kim S, Kim J M, Kim J S (2013) Targeted genome engineering in human cells with the Cas9 RNA-guided endonuclease. Nature Biotechnol 31: 230-232

Cong L, Ran F A, Cox D, Lin S, Barretto R, Habib N, Hsu P D, Wu X, Jiang W, Marraffini L A, Zhang F (2013) Multiplex genome engineering using CRISPR/Cas systems. Science 339: 819-823

Cui X, Ji D, Fisher D A, Wu Y, Briner D M, Weinstein E J (2011) Targeted integration in rat and mouse embryos with zinc-finger nucleases. Nature Biotechnol 29: 64-68

Deltcheva E, Chylinski K, Sharma C M, Gonzales K, Chao Y, Pirzada Z A, Eckert M R, Vogel J, Charpentier E (2011) CRISPR RNA maturation by trans-encoded small RNA and host factor RNase III. Nature 471: 602-607

Gaj T, Gersbach C A, Barbas Iii C F (2013) ZFN, TALEN, and CRISPR/Cas-based methods for genome engineering. Trends in Biotechnol Gasiunas G, Barrangou R, Horvath P. Siksnys V (2012) Cas9-crRNA ribonucleoprotein complex mediates specific DNA cleavage for adaptive immunity in bacteria. PNAS 109: E2579-E2586

Hauschild J, Petersen B, Santiago Y, Queisser A L, Carnwath J W, Lucas-Hahn A, Zhang L, Meng X, Gregory P D, Schwinzer R, Cost G J, Niemann H (2011) Efficient generation of a biallelic knockout in pigs using zinc-finger nucleases. PNAS 108: 12013-12017

Hockemeyer D, Wang H, Kiani S, Lai C S, Gao Q, Cassady J P, Cost G J, Zhang L, Santiago Y, Miller J C, Zeitler B, Cherone J M, Meng X, Hinkley S J, Rebar E J, Gregory P D, Urnov F D, Jaenisch R (2011) Genetic engineering of human pluripotent cells using TALE nucleases. Nat Biotechnol 29: 731-734

Hwang W Y, Fu Y, Reyon D, Maeder M L, Tsai S Q, Sander J D, Peterson R T, Yeh J R J, Joung J K (2013)

Efficient genome editing in zebrafish using a CRISPR-Cas system. Nature Biotechnol 31: 227-229

Jiang W, Bikard D, Cox D, Zhang F, Marraffini L A (2013) RNA-guided editing of bacterial genomes using CRISPR-Cas systems. Nature Biotechnol 31: 233-239

Jinek M, Chylinski K, Fonfara L Hauer M, Doudna J A, Charpentier E (2012) A programmable dual-RNA-guided DNA endonuclease in adaptive bacterial immunity. Science 337: 816-821

Laprise P (2011) Emerging role for epithelial polarity proteins of the crumbs family as potential tumor suppressors. J Biomed Biotechnol 2011; 2011:868217. doi: 10.1155/2011/868217

Lei Y, Guo X, Liu Y, Cao Y, Deng Y. Chen X, Cheng H, Dawid I B, Chen Y, Zhao H (2012) Efficient targeted gene disruption in *Xenopus* embryos using engineered transcription activator-like effector nucleases (TALENs). PNAS 109: 17484-17489

Li T, Huang S, Zhao X, Wright D A, Carpenter S, Spalding M H, Weeks D P, Yang B (2011) Modularly assembled designer TAL effector nucleases for targeted gene knockout and gene replacement in eukaryotes. Nucleic Acids Res 39: 6315-6325

Makarova K S, Haft D H, Barrangou R, Brouns S J J, Charpentier E, Horvath P, Moineau S, Mojica F J M, Wolf Y I, Yakunin A F, Van Der Oost J, Koonin E V (2011) Evolution and classification of the CRISPR-Cas systems. Nature Reviews Microbiology 9: 467-477

Mali P, Yang L, Esvelt K M, Aach J, Guell M, DiCarlo J E, Norville J E, Church G M (2013) RNA-guided human genome engineering via Cas9. Science 339: 823-826

Marraffini L A, Sontheimer E J (2010) CRISPR interference: RNA-directed adaptive immunity in bacteria and archaea. Nature Reviews Genetics 11: 181-190

Mekada K, Abe K, Murakami A, Nakamura S, Nakata H, Moriwaki K, Obata Y, Yoshiki A (2009) Genetic differences among C57BL/6 substrains. Exp Anim 58: 141-149

Miller J C, Tan S, Qiao G, Barlow K A, Wang J, Xia D F, Meng X, Paschon D E, Leung E, Hinkley S J, Dulay G P, Hua K L, Ankoudinova I, Cost G J, Urnov F D, Zhang H S, Holmes M C, Zhang L, Gregory P D, Rebar E J (2011) A TALE nuclease architecture for efficient genome editing. Nat Biotechnol 29: 143-148

Moore F E, Reyon D, Sander J D, Martinez S A, Blackburn J S, Khayter C, Ramirez C L, Joung J K, Langenau D M (2012) Improved somatic mutagenesis in zebrafish using transcription activator-like effector nucleases (TALENs). PLoS ONE 7: e37877

Orlando S J, Santiago Y, DeKelver R C, Freyvert Y, Boydston E A, Moehle E A, Choi V M, Gopalan S M, Lou J F, Li J, Miller J C, Holmes M C, Gregory P D, Umov F D, Cost G J (2010) Zinc-finger nuclease-driven targeted integration into mammalian genomes using donors with limited chromosomal homology. Nucleic Acids Res 38: e152-e152

Petkov P M, Ding Y, Cassell M A, Zhang W, Wagner G, Sargent E E, Asquith S, Crew V, Johnson K A, Robinson P, Scott V E, Wiles M V (2004) An efficient SNP system for mouse genome scanning and elucidating strain relationships. Genome Res 14: 1806-1811

Pieczynski J, Margolis B (2011) Protein complexes that control renal epithelial polarity. American Journal of Physiology—Renal Physiology 300: F589-F601

Porteus M H, Carroll D (2005) Gene targeting using zinc finger nucleases. Nature Biotechnology 23: 967-973

Qi L S, Larson M H, Gilbert L A, Doudna J A, Weissman J S, Arkin A P, Lim W A (2013) Repurposing CRISPR as an RNA-guided platform for sequence-specific control of gene expression. Cell 152: 1173-1183

Sander J D, Cade L, Khayter C, Reyon D, Peterson R T, Joung J K, Yeh J R J (2011) Targeted gene disruption in somatic zebrafish cells using engineered TALENs. Nature Biotechnology 29: 697-698

Sander J D, Reyon D, Maeder M L, Foley J E, Thibodeau-Beganny S, Li X, Regan M R, Dahlborg E J, Goodwin M J, Fu F, Voytas D F, Joung J K, Dobbs D (2010) Predicting success of oligomerized pool engineering (OPEN) for zinc finger target site sequences. BMC Bioinformatics 11: 543

Sander J D, Zaback P, Joung J K, Voytas D F, Dobbs D (2007) Zinc Finger Targeter (ZiFiT): An engineered zinc finger/target site design tool. Nucleic Acids Res 35: W599-W605

Shen B, Zhang J, Wu H, Wang J, Ma K, Li Z, Zhang X, Zhang P, Huang X (2013) Generation of gene-modified mice via Cas9/RNA-mediated gene targeting. Cell Research 23: 720-723

Stroud D A, Formosa L E, Wijeyeratne X W, Nguyen T N, Ryan M T (2013) Gene knockout using transcription activator-like effector nucleases (TALENs) reveals that human NDUFA9 protein is essential for stabilizing the junction between membrane and matrix arms of complex I. J BiolChem 288: 1685-1690

Sung Y H, Baek I J, Kim D H, Jeon J, Lee J, Lee K, Jeong D, Kim J S, Lee H W (2013) Knockout mice created by TALEN-mediated gene targeting. Nature Biotechnol 31: 23-24

Toye A A, Lippiat J D, Proks P, Shimomura K, Bentley L, Hugill A, Mijat V, Goldsworthy M, Moir L, Haynes A, Quarterman J, Freeman H C, Ashcroft F M, Cox R D (2005) A genetic and physiological study of impaired glucose homeostasis control in C57BL/6J mice. Diabetologia 48: 675-686

Wang H, Yang H, Shivalila C S, Dawlaty M M, Cheng A W, Zhang F, Jaenisch R (2013) One-step generation of mice carrying mutations in multiple genes by CRISPR/cas-mediated genome engineering. Cell 153: 910-918

Watt S R, Betthauser J M, Augenstein M L, Childs L A, Mell G D, Forsberg E J, Eisen A (2006) Direct and rapid modification of a porcine xenoantigen gene (GGTA1). Transplantation 82: 975-978

Wefers B, Meyer M, Ortiz O, De Angelis M H, Hansen J, Wurst W, Kuhn R (2013) Direct production of mouse disease models by embryo microinjection of TALENs and oligodeoxynucleotides. PNAS 110: 3782-3787

Zurita E, Chagoyen M, Cantero M, Alonso R, Gonzalez-Neira A, Lopez-Jimenez A, Lopez-Moreno J A, Landel C P, Benitez J, Pazos F, Montoliu L (2011) Genetic polymorphisms among C57BL/6 mouse inbred strains. Transgenic Res 20: 481-489

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A genetically engineered mouse comprising a corrected Crb1$^{rd8}$ mutation, wherein the mouse is a mouse strain selected from the group consisting of: 5558/B6(129S4)-Crb1<rd8>/Boc; B6.129P2-Prkcq$^{tm1Litt}$/J; STOCK Crb1$^{rd8}$/J; and B6/129-Crb1$^{rd8}$/J.

2. A genetically engineered mouse comprising a corrected Crb1$^{rd8}$ mutation, wherein the mouse comprises a genomic DNA sequence selected from:
GACAGTTACAGCAGTTATCGGTGTGCCTGTCTGTC (SEQ ID NO: 20) and/or the reverse complement thereof;
GACAGTTACAGCAGTTATAGGTGTGCCTGTCTGTC (SEQ ID NO: 21) and/or the reverse complement thereof;
GACAGCTACAGTTCTTATCGGTGTGCCTGTCTGTC (SEQ ID NO: 22) and/or the reverse complement thereof;
GACAGCTACAGTTCTTATCGGTGTGCCTGTCTCTC (SEQ ID NO: 23) and/or the reverse complement thereof;
GACAGTTACAGCAGTTATCGGTGTGCCTGTCTCTC (SEQ ID NO: 24) and/or the reverse complement thereof;
GACAGCTACAGCAGTTATCGGTGTGCCTGTCTCTC (SEQ ID NO: 25) and/or the reverse complement thereof;
GACAGCTACAGTTCTTATAGGTGTGCCTGTCTGTC (SEQ ID NO: 26) and/or the reverse complement thereof;
GACAGCTACAGTTCTTATCGGTGTGCCTGTCTCTC (SEQ ID NO: 27) and/or the reverse complement thereof;
GACAGTTACAGTTCTTATCGGTGTGCCTGTCTGTC (SEQ ID NO: 28) and/or the reverse complement thereof; and
GACAGTTACAGTAGTTATCGGTGTGCCTGTCTGTC (SEQ ID NO: 29) and/or the reverse complement thereof.

3. A genetically engineered mouse comprising a corrected Crb1$^{rd8}$ mutation, wherein the genetically engineered mouse comprises a repaired genomic DNA sequence encoding a portion of mouse Crb1 comprising the Crb1<rd8> locus and comprising one or more nucleotide differences compared to mouse Crb1 gene of a reference mouse of the same strain, wherein the one or more nucleotide differences do not result in a difference in the amino acid sequence of Crb1 encoded by the repaired genomic DNA sequence.

4. The genetically engineered mouse of claim 3, wherein the mouse is a C57BL/6N strain.

5. The genetically engineered mouse of claim 4, wherein the C57BL/6N strain is selected from the group consisting of: C57BL/6NJ; C57BL/6NJcl; C57BL/6NTac; C57BL/6NCr; C57BL/6NCrl; C57BL/6NHsd; and C57BL/6NCrlCrlj.

6. The genetically engineered mouse of claim 4, wherein the C57BL/6N strain is characterized by at least 5 single-nucleotide polymorphisms (SNPs), where: 08-015199792-M (r53709624) is C; 11-004367508-M (rs3659787) is A; 13-041017317-M (r53722313) is C; 15-057561875-M (rs3702158) is G; 19-049914266-M (rs3724876) is T.

7. The genetically engineered mouse of claim 3, wherein the mouse is a mouse strain selected from the group consisting of: 5558/B6(129S4)-Crb1<rd8>/Boc; B6.129P2-Prkcq$^{tm1Litt}$/J; STOCK Crb1$^{rd8}$/J; B6/129-Crb1$^{rd8}$/J, CXB12/HiAJ; CXB9/HiAJ; CXB2/ByJ; CXB3/ByJ; CXB5/ByJ; and HPG/BmJ/.

8. The genetically engineered mouse of claim 3, wherein the mouse comprises a genomic DNA sequence selected from:
GACAGTTACAGCAGTTATCGGTGTGCCTGTCTGTC (SEQ ID NO: 20) and/or the reverse complement thereof;
GACAGTTACAGCAGTTATAGGTGTGCCTGTCTGTC (SEQ ID NO: 21) and/or the reverse complement thereof;
GACAGCTACAGTTCTTATCGGTGTGCCTGTCTGTC (SEQ ID NO: 22) and/or the reverse complement thereof
GACAGCTACAGTTCTTATCGGTGTGCCTGTCTCTC (SEQ ID NO: 23) and/or the reverse complement thereof;
GACAGTTACAGCAGTTATCGGTGTGCCTGTCTCTC (SEQ ID NO: 24) and/or the reverse complement thereof;
GACAGCTACAGCAGTTATCGGTGTGCCTGTCTCTC (SEQ ID NO: 25) and/or the reverse complement thereof;
GACAGCTACAGTTCTTATAGGTGTGCCTGTCTGTC (SEQ ID NO: 26) and/or the reverse complement thereof;
GACAGCTACAGTTCTTATCGGTGTGCCTGTCTCTC (SEQ ID NO: 27) and/or the reverse complement thereof;
GACAGTTACAGTTCTTATCGGTGTGCCTGTCTGTC (SEQ ID NO: 28) and/or the reverse complement thereof; and
GACAGTTACAGTAGTTATCGGTGTGCCTGTCTGTC (SEQ ID NO: 29) and/or the reverse complement thereof.

* * * * *